US008399251B2

(12) United States Patent
Hald et al.

(10) Patent No.: US 8,399,251 B2
(45) Date of Patent: Mar. 19, 2013

(54) USE OF THE EXTRACELLULAR MARKER DNER FOR IDENTIFICATION AND SELECTION OF SPECIFIC PANCREATIC CELLS

(75) Inventors: Jacob Hald, Birkerød (DK); Ole Dragsbæk Madsen, Søborg (DK); Gérard Gradwohl, Plobsheim (FR); Georg Mellitzer, Andlau (FR)

(73) Assignee: Novo Nordisk A/S, Bagsvaerd (DK)

( * ) Notice: Subject to any disclaimer, the term of this patent is extended or adjusted under 35 U.S.C. 154(b) by 149 days.

(21) Appl. No.: 12/934,373

(22) PCT Filed: Apr. 3, 2009

(86) PCT No.: PCT/EP2009/054015
§ 371 (c)(1),
(2), (4) Date: Oct. 14, 2010

(87) PCT Pub. No.: WO2009/121958
PCT Pub. Date: Oct. 8, 2009

(65) Prior Publication Data
US 2011/0020297 A1    Jan. 27, 2011

Related U.S. Application Data

(60) Provisional application No. 61/123,490, filed on Apr. 9, 2008.

(30) Foreign Application Priority Data

Apr. 3, 2008  (EP) ..................................... 08103360

(51) Int. Cl.
*C12N 5/00* (2006.01)
(52) U.S. Cl. ........................................ 435/377; 435/384
(58) Field of Classification Search .................. 435/377, 435/384
See application file for complete search history.

(56) References Cited

U.S. PATENT DOCUMENTS

| | | | |
|---|---|---|---|
| 6,242,666 | B1 | 6/2001 | Sarvetnick et al. |
| 6,436,704 | B1 | 8/2002 | Roberts et al. |
| 2006/0014808 | A1 | 1/2006 | Hughes et al. |
| 2006/0148081 | A1 | 7/2006 | Kelly et al. |
| 2008/0242594 | A1* | 10/2008 | McKay et al. ..................... 514/3 |
| 2011/0020297 | A1 | 1/2011 | Hald et al. |
| 2011/0286977 | A1* | 11/2011 | Roep et al. ................... 424/93.7 |
| 2011/0287011 | A1 | 11/2011 | Gurney et al. |

FOREIGN PATENT DOCUMENTS

| | | |
|---|---|---|
| CA | 2600568 | 9/2006 |
| WO | 2005/030032 A2 | 4/2005 |
| WO | WO 2005/063971 | 7/2005 |
| WO | WO 2005/116073 | 12/2005 |
| WO | 2007/103282 A2 | 9/2007 |
| WO | 2009/083502 A1 | 7/2009 |

OTHER PUBLICATIONS

Ahnfelt-Ronne J. et al. Preservation of Proliferating Pancreatic Progenitor Cells . . . BMC Developmental Biology 7(1)1-13, Jun. 7, 2007.*
Ahnfelt-Ronne et al., BMC Developmental Biology, Biomed Central Ltd., London, 2007, vol. 7, No. 1, p. 63.
Apelqvist et al., Nature, 1999, vol. 400, No. 6747, pp. 877-881.
Cirulli et al., Journal of Cell Biology, 1998, vol. 140, pp. 1519-1534.
Circulli et al., Journal of Cell Biology, 2000, vol. 150, pp. 1445-1460.
Eiraku et al., Jouornal of Biological Chemistry, 2002, vol. 277, No. 28, pp. 25400-25407.
Hald et al., Journal of Histochemistry and Cytochemistry, 2008, vol. 56, No. 6, pp. 587-595.
Sugiyama et al., Proceedings of the National Academy of Sciences of the USA, 2007, vol. 104, No. 1, pp. 175-180.
White et al., Diabetes, 2008, vol. 57, No. 3, pp. 654-668.
Xu et al., Cell, 2008, vol. 132, No. 2, pp. 197-207.
D'Amour et al., Nature Biotechnology, 2006, vol. 24, No. 11, pp. 1392-1401.
Jorgensen et al., Endocrine Reviews, 2007, vol. 28, No. 6, pp. 685-705.
Ram et al., Journal of Neuro-Oncology, 2006, vol. 76, No. 3, pp. 239-248.
Sakamoto et al., European Respiratory Journal, 2001, vol. 17, No. 5, pp. 969-974.
Banerjee et al., "A Simple Two-Step Protocol for the Purification of Human Pancreatic Beta Cells", Diabetologia, 2009, vol. 52, pp. 621-625.
Krijger et al., "Enrichment of Beta Cells From the Human Fetal Pancreas by Fluorescence Activated Cell Sorting With a New Monoclonal Antibody", Diabetologia, 1992, vol. 35, pp. 436-443.
Dorrell et al., "Isolatio of Major Pancreatic Cell Types and Long-Term Culture-Initiating Cells Using Novel Human Surface Markers", Stem Cell Research, 2008, vol. 1, pp. 183-194.
Hori et al., "Enrichment of Putative Pancreatic Progenitor Cells From Mice by Sorting for PROMININ1 (CD133) and Platelet-Derived Growth Factor Receptor β", Stem Cells, 2008, vol. 26, pp. 2912-2920.
Iglesias et al., "Comprehensive Analysis of Human Pancreatic Islets Using Flow and Laser Scanning Cytometry", Transplantation Proceedings, 2008, vol. 40, pp. 351-354.
Koblas et al., "Differentiation of CD133-Positive Pancreatic Cells Into Insulin-Producing Islet-Like Cell Clusters", Transplantation Proceedings, 2008, vol. 40, pp. 415-418.
Martin et al., "Cloning and Characterization of the Human and Rat Islet-Specific Glucose-6-Phosphatase Catalytic Subunit-Related Protein (IGRP) Genes", Journal of Biological Chemistry, 2001, vol. 276, No. 27, pp. 25197-25207.
Vissing et al., "Monoclonal Antibodies Against Pancreatic Islet-Cell-Surface Antigens Selected by Flow Cytofluorometry", Scandinavian Journal Immunology, 1986, vol. 23, pp. 425-433.

* cited by examiner

*Primary Examiner* — Ralph Gitomer
(74) *Attorney, Agent, or Firm* — Jianjie Hu; Michael J. Brignati

(57) ABSTRACT

The invention relates to a method of identifying and obtaining cells that have the potential to differentiate into pancreatic cells, having the step of contacting a cell population containing endocrine pre-progenitor cells, endocrine progenitor cells, early endocrine cells, and/or fully differentiated endocrine cells with a DNER binding agent; as well as isolating and/or expanding cells obtained by the method and compositions thereof.

12 Claims, 10 Drawing Sheets

ClustalW mouse vs. human
CLUSTAL W (1.83) multiple sequence alignment

```
gi|23097346|_Mus        MPPRRAQAPGAPLLPVLALLPLLLGAGPQSGCLASPVSAAPLPAPGPCASQPCRNGGVCT 60
gi|116235485|_Homo      MQPRRAQAPGAQLLPALALLLLLLGAGPRGSSLANPVPAAPLSAPGPCAAQPCRNGGVCT 60
                        * ******* * ** **:......**:******** gi|23097346|_Mus        PRSVTDQEHPAADAEPRYSCTCPAGVSGTYCQFVADPCASNPCHHGNCSSSSSSSSDSYL 120
gi|116235485|_Homo      SRPEPDPQHPAPAGEPGYSCTCPAGISGANCQLVADPCASNPCHHGNCSSSSSSSSDGYL 120
                        .*. .* .:***. .** ********:**. **:***********************.**

gi|23097346|_Mus        CICNDGYEGLNCEQPLPSIPTSGWTESTAPRQLQPVPATQEPDIILPRSQATVTLPTWQP 180
gi|116235485|_Homo      CICNEGYEGPNCEQALPSLPATGWTESMAPRQLQPVPATQEPDKILPRSQATVTLPTWQP 180
                        **: .*:*::*** *********** ************* gi|23097346|_Mus        KTGQKVVEMKWDQVEVVPDVACGNASSNNSAGGRLVSFEVPQNTSVKIRQDANSLLILLW 240
gi|116235485|_Homo      KTGQKVVEMKWDQVEVIPDIACGNASSNSSAGGRLVSFEVPQNTSVKIRQDATASLILLW 240
                        **************::******:.******************.: *** gi|23097346|_Mus        KVTATGFQQCSLIDGRSVTPLQAPGGLVLLEEMLALGPNHFIGFVNDSVAKSIVALRLTL 300
gi|116235485|_Homo      KVTATGFQQCSLIDGRSVTPLQASGGLVLLEEMLALGNNHFIGFVNDSVTKSIVALRLTL 300
                        *********************.********.*******.******** gi|23097346|_Mus        VVKASNCVPGDSHSNDLECSGKGKCATKPSEATFSCTCQDQYIGTFCEEFDACQRKPCQN 360
gi|116235485|_Homo      VVKVSTCVPGESHANDLECSGKGKCTTKPSEATFSCTCEEQYVGTFCEEYDACQRKPCQN 360
                        ***.*.***::********:********:::****:******* gi|23097346|_Mus        EASCIDANEKQDGSNFTCLCLPGYTGELCQSKIDYCVLDPCRNGATCVSSLSGFTCQCLE 420
gi|116235485|_Homo      NASCIDANEKQDGSNFTCVCLPGYTGELCQSKIDYCILDPCRNGATCISSLSGFTCQCPE 420
                        :***************:*************:******:********.* gi|23097346|_Mus        GYFGSACEEKVDPCMSSPCQNNGTCYVDGVHFTCSCSPGFTGPTCAQLVDFCALSPCAHG 480
gi|116235485|_Homo      GYFGSACEEKVDPCASSPCQNNGTCYVDGVHFTCNCSPGFTGPTCAQLIDFCALSPCAHG 480
                        ************.***************.*********:******** gi|23097346|_Mus        MCRSVGTSYKCLCDPGYHGLYCEEEYNECLSAPCLNAATCRDLINGYECVCLAEYKGTHC 540
gi|116235485|_Homo      TCRSVGTSYKCLCDPGYHGLYCEEEYNECLSAPCLNAATCRDLVNGYECVCLAEYKGTHC 540
                         ****************************************:************** gi|23097346|_Mus        ELYKDPCANISCLNGGTCDSEGLNGTCICAPGFTGEECDIDINECDSNPCHHAGTCLDQP 600
gi|116235485|_Homo      ELYKDPCANVSCLNGATCDSDGLNGTCICAPGFTGEECDIDINECDSNPCHHGGSCLDQP 600
                        *******:*.:*****************************.*.***** gi|23097346|_Mus        NGYTCHCPHGWVGANCEIHLQWKSGHMAESLTNMPRHSLYIIIGALCVAFILMLIILIVG 660
gi|116235485|_Homo      NGYNCHCPHGWVGANCEIHLQWKSGHMAESLTNMPRHSLYIIIGALCVAFILMLIILIVG 660
                        *.**************************************************** gi|23097346|_Mus        ICRISRIEYQGSSRPAYEEFYNCRSIDSEFSNAIASIRHARFGKKSRPAMYDVTPIAYED 720
gi|116235485|_Homo      ICRISRIEYQGSSRPAYEEFYNCRSIDSEFSNAIASIRHARFGKKSRPAMYDVSPIAYED 720
                        ***************************************************:**** gi|23097346|_Mus        YSPDDKPLVTLIKTKDL 737
gi|116235485|_Homo      YSPDDKPLVTLIKTKDL 737
                        *****************
```

Fig. 2

```
Name: gi_23097346_Mus    Length: 737
MPPRRAQAPGAPLLPVLALLPLLLGAGPQSGCLASPVSAAPLPAPGPCASQPCRNGGVCTPRSVTDQEHPAADAEPRYSC      80
TCPAGVSGTYCQFVADPCASNPCHHGNCSSSSSSSSDSYLCICNDGYEGLNCEQPLPSIPTSGWTESTAPRQLQPVPATQ     160
EPDIILPRSQATVTLPTWQPKTGQKVVEMKWDQVEVVPDVACGNASSNNSAGGRLVSFEVPQNTSVKIRQDANSLLILLW     240
KVTATGFQQCSLIDGRSVTPLQAPGGLVLLEEMLALGPNHFIGFVNDSVAKSIVALRLTLVVKASNCVPGDSHSNDLECS     320
GKGKCATKPSEATFSCTCQDQYIGTFCEEFDACQRKPCQNEASCIDANEKQDGSNFTCLCLPGYTGELCQSKIDYCVLDP     400
CRNGATCVSSLSGFTCQCLEGYFGSACEEKVDPCMSSPCQNNGTCYVDGVHFTCSCSPGFTGPTCAQLVDFCALSPCAHG     480
MCRSVGTSYKCLCDPGYHGLYCEEEYNECLSAPCLNAATCRDLINGYECVCLAEYKGTHCELYKDPCANISCLNGGTCDS     560
EGLNGTCICAPGFTGEECDIDINECDSNPCHHAGTCLDQPNGYTCHCPHGWVGANCEIHLQWKSGHMAESLTNMPRHSLY     640
IIIGALCVAFILMLIILIVGICRISRIEYQGSSRPAYEEFYNCRSIDSEFSNAIASIRHARFGKKSRPAMYDVTPIAYED     720
YSPDDKPLVTLIKTKDL
................................................................................      80
................................................................................     160
................................................................................     240
...............G................................................................     320
................................................................................     400
................................................................................     480
................................................................................     560
................................................................................     640
................................................................................     720
.................
```

Fig. 3A

```
Name: gi_11623548_Homo    Length: 737
MQPRRAQAPGAQLLPALALLLLLGAGPRGSSLANPVPAAPLSAPGPCAAQPCRNGGVCTSRPEPDPQHPAPAGEPGYSC       80
TCPAGISGANCQLVADPCASNPCHHGNCSSSSSSSSSDGYLCICNEGYEGPNCEQALPSLPATGWTESMAPRQLQPVPATQ    160
EPDKILPRSQATVTLPTWQPKTGQKVVEMKWDQVEVIPDIACGNASSNSSAGGRLVSFEVPQNTSVKIRQDATASLILLW    240
KVTATGFQQCSLIDGRSVTPLQASGGLVLLEEMLALGNNHFIGFVNDSVTKSIVALRLTLVVKVSTCVPGESHANDLECS    320
GKGKCTTKPSEATFSCTCEEQYVGTFCEEYDACQRKPCQNNASCIDANEKQDGSNFTCVCLPGYTGELCQSKIDYCILDP    400
CRNGATCISSLSGFTCQCPEGYFGSACEEKVDPCASSPCQNNGTCYVDGVHFTCNCSPGFTGPTCAQLIDFCALSPCAHG    480
TCRSVGTSYKCLCDPGYHGLYCEEEYNECLSAPCLNAATCRDLVNGYECVCLAEYKGTHCELYKDPCANVSCLNGATCDS    560
DGLNGTCICAPGFTGEECDIDINECDSNPCHHGGSCLDQPNGYNCHCPHGWVGANCEIHLQWKSGHMAESLTNMPRHSLY    640
IIIGALCVAFILMLIILIVGICRISRIEYQGSSRPAYEEFYNCRSIDSEFSNAIASIRHARFGKKSRPAMYDVSPIAYED    720
YSPDDKPLVTLIKTKDL
................................................................................      80
...........................................................G....................     160
................................................................................     240
...............G................................................................     320
................................................................................     400
................................................................................     480
................................................................................     560
................................................................................     640
................................................................................     720
.................
```

Fig. 3B

```
>gi_23097346__Mus          737 amino acids

netglycate-1.0 prediction results MPPRRAQAPGAPLLPVLALLPLLLGAGPQSGCLASPVSAAPLPAPGPCAS    #    50
        QPCRNGGVCTPRSVTDQEHPAADAEPRYSCTCPAGVSGTYCQFVADPCAS    #   100
        NPCHHGNCSSSSSSSSDSYLCICNDGYEGLNCEQPLPSIPTSGWTESTAP    #   150
        RQLQPVPATQEPDIILPRSQATVTLPTWQPKTGQKVVEMKWDQVEVVPDV    #   200
        ACGNASSNNSAGGRLVSFEVPQNTSVKIRQDANSLLILLWKVTATGFQQC    #   250
        SLIDGRSVTPLQAPGGLVLLEEMLALGPNHFIGFVNDSVAKSIVALRLTL    #   300
        VVKASNCVPGDSHSNDLECSGKGKCATKPSEATFSCTCQDQYIGTFCEEF    #   350
        DACQRKPCQNEASCIDANEKQDGSNFTCLCLPGYTGELCQSKIDYCVLDP    #   400
        CRNGATCVSSLSGFTCQCLEGYFGSACEEKVDPCMSSPCQNNGTCYVDGV    #   450
        HFTCSCSPGFTGPTCAQLVDFCALSPCAHGMCRSVGTSYKCLCDPGYHGL    #   500
        YCEEEYNECLSAPCLNAATCRDLINGYECVCLAEYKGTHCELYKDPCANI    #   550
        SCLNGGTCDSEGLNGTCICAPGFTGEECDIDINECDSNPCHHAGTCLDQP    #   600
        NGYTCHCPHGWVGANCEIHLQWKSGHMAESLTNMPRHSLYIIIGALCVAF    #   650
        ILMLIILIVGICRISRIEYQGSSRPAYEEFYNCRSIDSEFSNAIASIRHA    #   700
        RFGKKSRPAMYDVTPIAYEDYSPDDKPLVTLIKTKDL                 #   750

```
>gi_116235485__Homo      737 amino acids

netglycate-1.0 prediction results MQPRRAQAPGAQLLPALALLLLLLGAGPRGSSLANPVPAAPLSAPGPCAA    #     50
        QPCRNGGVCTSRPEPDPQHPAPAGEPGYSCTCPAGISGANCQLVADPCAS    #    100
        NPCHHGNCSSSSSSSSSDGYLCICNEGYEGPNCEQALPSLPATGWTESMAP   #    150
        RQLQPVPATQEPDKILPRSQATVTLPTWQPKTGQKVVEMKWDQVEVIPDI    #    200
        ACGNASSNSSAGGRLVSFEVPQNTSVKIRQDATASLILLWKVTATGFQQC    #    250
        SLIDGRSVTPLQASGGLVLLEEMLALGNNHFIGFVNDSVTKSIVALRLTL    #    300
        VVKVSTCVPGESHANDLECSGKGKCTTKPSEATFSCTCEEQYVGTFCEEY    #    350
        DACQRKPCQNNASCIDANEKQDGSNFTCVCLPGYTGELCQSKIDYCILDP    #    400
        CRNGATCISSLSGFTCQCPEGYFGSACEEKVDPCASSPCQNNGTCYVDGV    #    450
        HFTCNCSPGFTGPTCAQLIDFCALSPCAHGTCRSVGTSYKCLCDPGYHGL    #    500
        YCEEEYNECLSAPCLNAATCRDLVNGYECVCLAEYKGTHCELYKDPCANV    #    550
        SCLNGATCDSDGLNGTCICAPGFTGEECDIDINECDSNPCHHGGSCLDQP    #    600
        NGYNCHCPHGWVGANCEIHLQWKSGHMAESLTNMPRHSLYIIIGALCVAF    #    650
        ILMLIILIVGICRISRIEYQGSSRPAYEEFYNCRSIDSEFSNAIASIRHA    #    700
        RFGKKSRPAMYDVSPIAYEDYSPDDKPLVTLIKTKDL                 #    750

```
Name: gi_23097346__Mus  Length:  737
MPPRRAQAPGAPLLPVLALLPLLLGAGPQSGCLASPVSAAPLPAPGPCASQPCRNGGVCTPRSVTDQEHPAADAEPRYSC      80
TCPAGVSGTYCQFVADPCASNPCHHGNCSSSSSSSSDSYLCICNDGYEGLNCEQPLPSIPTSGWTESTAPRQLQPVPATQ     160
EPDIILPRSQATVTLPTWQPKTGQKVVEMKWDQVEVVPDVACGNASSNNSAGGRLVSFEVPQNTSVKIRQDANSLLILLW     240
KVTATGFQQCSLIDGRSVTPLQAPGGLVLLEEMLALGPNHFIGFVNDSVAKSIVALRLTLVVKASNCVPGDSHSNDLECS     320
GKGKCATKPSEATFSCTCQDQYIGTFCEEFDACQRKPCQNEASCIDANEKQDGSNFTCLCLPGYTGELCQSKIDYCVLDP     400
CRNGATCVSSLSGFTCQCLEGYFGSACEEKVDPCMSSPCQNNGTCYVDGVHFTCSCSPGFTGPTCAQLVDFCALSPCAHG     480
MCRSVGTSYKCLCDPGYHGLYCEEEYNECLSAPCLNAATCRDLINGYECVCLAEYKGTHCELYKDPCANISCLNGGTCDS     560
EGLNGTCICAPGFTGEECDIDINECDSNPCHHAGTCLDQPNGYTCHCPHGWVGANCEIHLQWKSGHMAESLTNMPRHSLY     640
IIIGALCVAFILMLIILIVGICRISRIEYQGSSRPAYEEFYNCRSIDSEFSNAIASIRHARFGKKSRPAMYDVTPIAYED     720
YSPDDKPLVTLIKTKDL
................................................................................      80
............................N...................................................     160
.........................................N........................N.............     240
.................................................N..............................     320
................................................................N...............     400
..............................................N.................................     480
..............................................................N.................     560
...N..............................................................................     640
................................................................................     720
.................                                                                     800
```

Fig. 5A

```
Name: gi_116235485__Homo  Length:  737
MQPRRAQAPGAQLLPALALLLLLLGAGPRGSSLANPVPAAPLSAPGPCAAQPCRNGGVCTSRPEPDPQHPAPAGEPGYSC      80
TCPAGISGANCQLVADPCASNPCHHGNCSSSSSSSSSDGYLCICNEGYEGPNCEQALPSLPATGWTESMAPRQLQPVPATQ    160
EPDKILPRSQATVTLPTWQPKTGQKVVEMKWDQVEVIPDIACGNASSNNSSAGGRLVSFEVPQNTSVKIRQDATASLILLW    240
KVTATGFQQCSLIDGRSVTPLQASGGLVLLEEMLALGNNHFIGFVNDSVTKSIVALRLTLVVKVSTCVPGESHANDLECS     320
GKGKCTTKPSEATFSCTCEEQYVGTFCEEYDACQRKPCQNNASCIDANEKQDGSNFTCVCLPGYTGELCQSKIDYCILDP    400
CRNGATCISSLSGFTCQCPEGYFGSACEEKVDPCASSPCQNNGTCYVDGVHFTCNCSPGFTGPTCAQLIDFCALSPCAHG    480
TCRSVGTSYKCLCDPGYHGLYCEEEYNECLSAPCLNAATCRDLVNGYECVCLAEYKGTHCELYKDPCANVSCLNGATCDS    560
DGLNGTCICAPGFTGEECDIDINECDSNPCHHGGSCLDQPNGYNCHCPHGWVGANCEIHLQWKSGHMAESLTNMPRHSLY    640
IIIGALCVAFILMLIILIVGICRISRIEYQGSSRPAYEEFYNCRSIDSEFSNAIASIRHARFGKKSRPAMYDVSPIAYED    720
YSPDDKPLVTLIKTKDL
................................................................................      80
............................N...................................................     160
.........................................N........................N.............     240
.................................................N..............................     320
................................................................N...............     400
..............................................N.................................     480
..............................................................N.................     560
...N..............................................................................     640
................................................................................     720
.................                                                                     800
```

Fig. 5B

```
Name: gi_23097346_Mus            Length:  737
MPPRRAQAPGAPLLPVLALLPLLLGAGPQSGCLASPVSAAPLPAPGPCASQPCRNGGVCTPRSVTDQEHPAADAEPRYSC
TCPAGVSGTYCQFVADPCASNPCHHGNCSSSSSSSSDSYLCICNDGYEGLNCEQPLPSIPTSGWTESTAPRQLQPVPATQ
EPDIILPRSQATVTLPTWQPKTGQKVVEMKWDQVEVVPDVACGNASSNNSAGGRLVSFEVPQNTSVKIRQDANSLLILLW
KVTATGFQQCSLIDGRSVTPLQAPGGLVLLEEMLALGPNHFIGFVNDSVAKSIVALRLTLVVKASNCVPGDSHSNDLECS
GKGKCATKPSEATFSCTCQDQYIGTFCEEFDACQRKPCQNEASCIDANEKQDGSNFTCLCLPGYTGELCQSKIDYCVLDP
CRNGATCVSSLSGFTCQCLEGYFGSACEEKVDPCMSSPCQNNGTCYVDGVHFTCSCSPGFTGPTCAQLVDFCALSPCAHG
MCRSVGTSYKCLCDPGYHGLYCEEEYNECLSAPCLNAATCRDLINGYECVCLAEYKGTHCELYKDPCANISCLNGGTCDS
EGLNGTCICAPGFTGEECDIDINECDSNPCHHAGTCLDQPNGYTCHCPHGWVGANCEIHLQWKSGHMAESLTNMPRHSLY
IIIGALCVAFILMLIILIVGICRISRIEYQGSSRPAYEEFYNCRSIDSEFSNAIASIRHARFGKKSRPAMYDVTPIAYED
YSPDDKPLVTLIKTKDL
_____    ...........................................
...........................................................T..T..........T.
...............T..............................................................
...............................................................................
...............................................................................
...............................................................................
...............................................................................
...............................................................................
...............................................................................
...............................................................................
...............................................................................
...............................................................................
..................
```

Fig. 6A

```
Name: gi_11623548_Homo           Length:  737
MQPRRAQAPGAPLLPALALLLLLLGAGPRGSSLANPVPAAPLSAPGPCAAQPCRNGGVCTSRPEPDPQHPAPAGEPGYSC
TCPAGISGANCQLVADPCASNPCHHGNCSSSSSSSSSDGYLCICNEGYEGPNCEQALPSLPATGWTESMAPRQLQPVPATQ
EPDKILPRSQATVTLPTWQPKTGQKVVEMKWDQVEVIPDIACGNASSNSSAGGRLVSFEVPQNTSVKIRQDATASLILLW
KVTATGFQQCSLIDGRSVTPLQASGGLVLLEEMLALGNNHFIGFVNDSVTKSIVALRLTLVVKVSTCVPGESHANDLECS
GKGKCTTKPSEATFSCTCEEQYVGTFCEEYDACQRKPCQNNASCIDANEKQDGSNFTCVCLPGYTGELCQSKIDYCILDP
CRNGATCISSLSGFTCQCPEGYFGSACEEKVDPCASSPCQNNGTCYVDGVHFTCNCSPGFTGPTCAQLIDFCALSPCAHG
TCRSVGTSYKCLCDPGYHGLYCEEEYNECLSAPCLNAATCRDLVNGYECVCLAEYKGTHCELYKDPCANVSCLNGATCDS
DGLNGTCICAPGFTGEECDIDINECDSNPCHHGGSCLDQPNGYNCHCPHGWVGANCEIHLQWKSGHMAESLTNMPRHSLY
IIIGALCVAFILMLIILIVGICRISRIEYQGSSRPAYEEFYNCRSIDSEFSNAIASIRHARFGKKSRPAMYDVSPIAYED
YSPDDKPLVTLIKTKDL
_____    .........................T....................
....................................................................T.
...............T...............................................................
...............................................................................
...............................................................................
...............................................................................
...............................................................................
...............................................................................
...............................................................................
...............................................................................
...............................................................................
...............................................................................
..................
```

Fig. 6B

USE OF THE EXTRACELLULAR MARKER DNER FOR IDENTIFICATION AND SELECTION OF SPECIFIC PANCREATIC CELLS

CROSS-REFERENCE TO RELATED APPLICATIONS

This application is a 35 U.S.C. §371 national stage application of International Patent Application PCT/EP2009/054015 (published as WO 2009/121958), filed Apr. 3, 2009, which claimed priority of European Patent Application 08103360.7, filed Apr. 3, 2008; this application further claims priority under 35 U.S.C. §119 of U.S. Provisional Application 61/123,490, filed Apr. 9, 2008.

FIELD OF THE INVENTION

In some aspects the invention relates to a selective cell surface marker, DNER, which permits the identification, selection and/or quantification of a unique subset of cells with pancreatic endocrine pre-progenitor phenotype and their progeny. In some aspects the selective cell surface marker is selected from the group consisting of DNER, DISP2, SEZ6L2, LRP11 and SLC30A8.

Compositions, cell cultures, and cell populations comprising pancreatic cells selected from the group consisting of endocrine pre-progenitor cells, endocrine progenitor cells, early endocrine cells, and/or fully differentiated endocrine cells are also contemplated as well as methods of producing fully differentiated endocrine cells and detecting endocrine pre-progenitor cells, endocrine progenitor cells, early endocrine cells, and/or fully differentiated endocrine cells.

INCORPORATION-BY-REFERENCE OF THE SEQUENCE LISTING

In accordance with 37 C.F.R. §1.52(e)(5), Applicants enclose herewith the Sequence Listing for the above-captioned application entitled "SEQUENCE LISTING", created on Jun. 2, 2010. The Sequence Listing is made up of 43 bytes, and the information contained in the attached "SEQUENCE LISTING" is identical to the information in the specification as originally filed. No new matter is added.

BACKGROUND OF THE INVENTION

Beta cell transplantation holds great promise to improve treatment of Type 1 diabetes but a number of obstacles need to be overcome first. Among these is the scarcity of available donor islets. Embryonic stem (ES) cell derived beta cells can in principle supply unlimited numbers of beta cells for transplantation but reliable protocols for generating fully functional beta cells are not yet developed. Formation of definitive endoderm (DE) cells from embryonic stem cells has been reported for both mouse and human ES cells in, e.g., WO 2005/116073, WO 2005/063971, and US 2006/0148081. Efficient generation of pancreatic endoderm (PE) cells from, e.g., DE cells is advantageous for generation of insulin-producing beta cells for the treatment of diabetes.

In attempting to cultivate fully differentiated pancreatic Islet cells, the objective has long been to isolate pancreatic cells including pancreatic endocrine pre-progenitor cells that are capable of differentiating into pancreatic beta cells or islets. One important step in isolation of the pancreatic endocrine lineage from the exocrine lineage would be to identify recognizable cell markers, specific for the pancreatic endocrine pre-progenitor cells and/or progeny thereof. Both intracellular and extracellular markers have been investigated for this purpose. Intracellular markers, particularly transcription factors detected in embryonic pancreatic cells that develop into fully differentiated Islet cells, have been extensively studied as progenitor markers. In some aspects these intracellular markers are transcription factors detected in embryonic pancreatic cells that develop into mature islet cells. Transcription factors such as Pdx1, Ngn3, Pax6, and Isl1, for example, have been studied. They are expressed in cells that are programmed during embryonic development to become pancreatic endocrine cells. However, these intracellular markers offer less practical value than extracellular markers, because analysis of expression of those markers requires either the killing of the cells or permanent modification of the cells by genetic engineering of reporter genes into the cells.

In particular, the earliest multipotent stem or progenitor cells comprising the early pancreatic bud structures (found at day 9.5-10.5 of mouse fetal development) co-express 3 transcription factors: Pdx1, Nkx6.1 and Ptf1a. The expression of Ptf1a and Nkx6.1 then segregate into the peripheral acinar committed domain and the central ductal/endocrine committed domain, respectively. See Hald et al., J Histochem Cytochem (2008); 56(6):587-95. It is thus of high priority to identify useful surface markers that are selectively expressed in pancreatic tissue subsets, such as the particular subpopulation of early "ductal/endocrine" progenitors that already committed to chose the endocrine lineage. We have used the nomenclature for these cells as "endocrine pre-progenitors". At this stage DNER is selectively expressed on the surface of endocrine pre-progenitor cells. Such cells will later express Ngn3 and progress towards endocrine maturation.

Once identified, extracellular markers would offer the advantage that the cells expressing the marker can be sorted under sterile conditions and kept alive. Epithelial cell adhesion molecules such as Ep-CAM and integrins have been investigated as pancreatic Islet progenitor markers. See, e.g., Cirulli et al., J. Cell Biol. 140: 1519-1534 (1998); and Cirulli et al., J. Cell Biol. 150: 1445-1460 (2000).

DESCRIPTION OF THE DRAWINGS

FIG. 1A shows a typical 8 µm mouse e15.5 pancreas tissue section as a schematic illustration. Cells in the mouse pancreas do not differentiate at the same time. Therefore, cells in different stages of development can be observed at a given time. At e15.5 two main domains are observed, a central and a peripheral. The central domain contains cells that have developed into early endocrine cells, endocrine progenitors, endocrine pre-progenitors, and ductal/endocrine progenitors. This central domain does not contain cells of the acinar lineage. Cells of the acinar lineage are found in the peripheral domain. Cells in the peripheral domain are Ptf1a$^+$ and Pdx1$^+$, but Nk6.1$^-$, Ddr1$^-$, and Dner$^-$. In the central domain cells are also Pdx1$^+$. Cells of the beta-cell lineage are Dner$^{low}$, and some of such cells will be positive for insulin. Compared to the number of Dner$^+$ cells, most of the cells in the central domain are Ddr1$^+$. Comparable cells and localisation thereof are found in the human pancreas. FIG. 1B shows a schematic illustration of the different stages a cell passes through. In the pancreas a cell starts out being part of the multi potent pancreatic progenitor pool, i.e. Pdx1$^+$/Nkx6.1$^+$/Ptf1a$^+$. The first choice of fate made by a cell is to go either in the acinar (Ptf1a$^+$) or in the ductal/endocrine lineage (Ptf1a$^-$ as well as Pdx1$^+$ and Nkx6.1$^+$ or Pdx1$^+$, Nkx6.1$^+$ and Ddr1$^+$). Some of these cells will take the fate of the ductal lineage and some will become endocrine pre-progenitor cells by turning on Dner. When a pancreatic cell is Dner+ it has the potential for choosing an endocrine fate and will thus later turn on Ngn3. Once the cell has turned on Ngn3 it is an endocrine progenitor cell. Dner is co-expressed with Ngn3 but some Ngn3 positive cells are found to be Dner negative. An Ngn3+ cell is also Pdx1+. Ngn3 expression is only transient in a progenitor cell and triggers the endocrine differentiation program through particular stages where other transcription factors including NeuroD, Pax6, Arx (in alpha cells), and Pax4 (in beta cells) become activated. These transcription factors are in part responsible for activation of the hormone genes and when the early endocrine cells become positive for hormones they are almost always already negative for Ngn3 but then, e.g., Pax6+. From this time point the cells will develop into one of the fully differentiated endocrine cell types (alpha-, beta-, delta-, PP- and ghrelin-cells) depending on previous and future fate-determining inputs.

FIG. 2. ClustalW of mouse and human Dner. Alignment identity is 90%. The transmembrane domain is underlined: Amino acids 639-661. The extracellular part is amino acids 1-638. This includes an N-terminal signal sequence that may cleaved off (i.e. first 30-35 amino acids). The alignment will display by default the following symbols denoting the degree of conservation observed in each column: "*" means that the residues or nucleotides in that column are identical in all sequences in the alignment. ":" means that conserved substitutions have been observed. "." means that semi-conserved substitutions are observed.

FIG. 3. GlcNAc O-glycosylation of mouse (A) and human (B) Dner. GlcNAc O-glycosylation is predicted to be present on the extracellular side of mouse and human Dner and is indicated with a "G".

FIG. 4. Glycation of epsilon amino groups of lysines of mouse (A) and human (B) Dner. Glycation is predicted to be present on the extracellular side of mouse and human Dner and is indicated with a "G".

FIG. 5. N-glycosylation on asparagines of mouse (A) and human (B) Dner. N-glycosylation is predicted to be present on the extracellular side of mouse and human Dner and is indicated with a "N".

FIG. 6. Mucin type GalNAc O-glycosylation of mouse (A) and human (B) Dner. Glycosylations are predicted to be present on the extracellular side of mouse and human Dner and is indicated with a "T". Underlining, i.e. "_____", indicate the signal peptide that is cleaved off.

SUMMARY OF THE INVENTION

Figure 1:
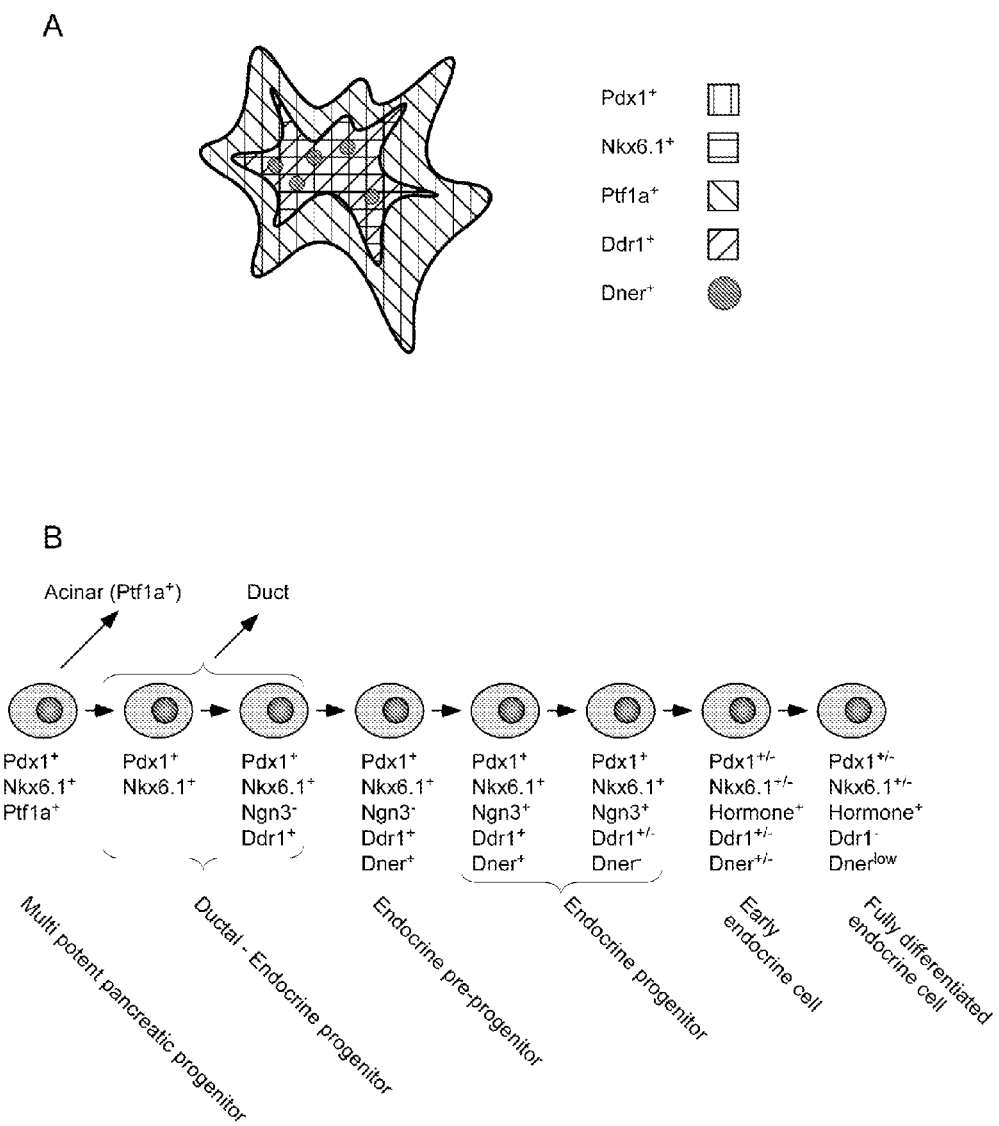
FIG. 1.

In some aspects the present invention discloses the use of the extracellular marker DNER for identification and selection of specific pancreatic cells. In some aspects the present invention discloses the use of an extracellular marker selected from the group consisting of DNER, DISP2, SEZ6L2, LRP11 and SLC30A8 for identification and selection of specific pancreatic cells.

In some aspects the invention relates to a method of identification of cells comprising cells selected from the group consisting of endocrine pre-progenitor cells, endocrine progenitor cells, early endocrine cells, and/or fully differentiated endocrine cells, the method comprising contacting a cell population comprising pancreatic cells with a DNER binding reagent. In some aspects the invention relates to a method of identification of cells comprising cells selected from the group consisting of endocrine pre-progenitor cells, endocrine progenitor cells, early endocrine cells, and/or fully differentiated endocrine cells, the method comprising contacting a cell population comprising pancreatic cells with a binding reagent selected from the group consisting of DNER, DISP2, SEZ6L2, LRP11 and SLC30A8.

In some aspects the invention relates to a method of obtaining a culture of cells comprising cells selected from the group consisting of endocrine pre-progenitor cells, endocrine progenitor cells, early endocrine cells, and/or fully differentiated endocrine cells, the method comprising: contacting a cell population comprising pancreatic cells with a DNER binding reagent and separating the cells that binds the DNER binding reagent in a fraction of DNER positive cells from cells that do not bind the DNER binding reagent.

In some aspects the invention relates to a method of obtaining a culture of cells comprising cells selected from the group consisting of endocrine pre-progenitor cells, endocrine progenitor cells, early endocrine cells, and/or fully differentiated endocrine cells, the method comprising: obtaining cells purified according to the method described above or herein and then subsequently culturing the obtained cells under conditions which facilitate differentiation of the cells into pancreatic cells comprising cells selected from the group consisting of endocrine pre-progenitor cells, endocrine progenitor cells, early endocrine cells, and/or fully differentiated endocrine cells.

In some aspects the invention relates to a method of expanding the number of cells comprising cells selected from the group consisting of endocrine pre-progenitor cells, endocrine progenitor cells, early endocrine cells, and/or fully differentiated endocrine cells, the method comprising: obtaining cells purified according to the method described above or herein and then subsequently culturing the obtained cells under conditions which facilitate expansion of the cell type(s) obtained.

In some aspects the invention relates to a method of expanding the number of cells comprising cells selected from the group consisting of endocrine pre-progenitor cells, endocrine progenitor cells, early endocrine cells, and/or fully differentiated endocrine cells, the method comprising: obtaining cells purified and expanded according to the method described above or herein and then subsequently culturing the obtained cells under conditions which facilitates differentiation of the cells into pancreatic cells selected from the group consisting of endocrine pre-progenitor cells, endocrine progenitor cells, early endocrine cells, and/or fully differentiated endocrine cells.

In some aspects the invention relates to a method of providing pancreatic endocrine function to a mammal deficient in its production of at least one pancreatic hormone wherein cells are obtained by any of the methods described above or herein, the method further comprising the steps of: implanting into the mammal the obtained cells in an amount sufficient to produce a measurable amount of at least one pancreatic hormone in the mammal.

In some aspects the invention relates to a method of quantifying DNER positive cells comprising pancreatic cells by a) contacting the cells with a DNER binding reagent; and b) determining the quantity of cells that exhibit DNER as a cell surface marker (DNER positive cells).

In some aspects the invention relates to a method for the optimisation of an in vitro protocol, wherein the number of DNER expressing cells (DNER positive cells) is periodically monitored.

In some aspects the invention relates to an isolated cell selected from the group consisting of endocrine pre-progenitor cells, endocrine progenitor cells, early endocrine cells and fully differentiated endocrine cells obtained by any of the methods defined herein.

In some aspects the invention relates to a composition comprising isolated cells selected from one or more cells from the group consisting of endocrine pre-progenitor cells, endocrine progenitor cells, early endocrine cells and fully differentiated endocrine cells obtained by a method as defined in any of the methods defined herein.

In some aspects the invention relates to the use of a DNER-binding reagent to identify or select cells that express DNER protein as a cell surface marker.

In some aspects the invention relates to the use of DNER protein as a cell surface marker to obtain a culture of pancreatic endocrine cells.

The DNER positive cells which are identified, enriched, and/or isolated in the methods of the present invention have the potential to differentiate into various cell types of the pancreatic lineage. In some aspects the DNER positive cells are differentiated further into insulin producing cells—this may be done so as to obtain insulin producing cells alone or to produce cultures of cells which also include glucagon, somatostatin, pancreatic polypeptide, and/or ghrelin producing cells. The DNER, DISP2, SEZ6L2, LRP11 and/or SLC30A8 positive cells which are identified, enriched, and/or isolated in the methods of the present invention have the potential to differentiate into various cell types of the pancreatic lineage. In some aspects the DNER, DISP2, SEZ6L2, LRP11 and/or SLC30A8 positive cells are differentiated further into insulin producing cells—this may be done so as to obtain insulin producing cells alone or to produce cultures of cells which also include glucagon, somatostatin, pancreatic polypeptide, and/or ghrelin producing cells.

DESCRIPTION OF THE INVENTION

DNER is present on pancreatic cells from the stage of differentiation from endocrine pre-progenitor cells to fully differentiated pancreatic cells. In comparison, DDR1 is present on pancreatic cells from the stage of differentiation from ductal/endocrine progenitor cells to early endocrine cells. Thus, DNER appears at a later stage during the development of pancreatic cells compared to DDR1 and is also expressed at later stages. Accordingly, DNER provides an extracellular marker of pancreatic cells at a stage of differentiation where the cells are committed to the endocrine lineage. Use of the extracellular marker DNER for identification, enrichment, and/or isolation of pancreatic cells provides cells which have the potential to become fully differentiated endocrine cells but have lost the potential to become ductal or acinar cells.

DISP2, SEZ6L2, LRP11 and SLC30A8 are extracellular markers of the endocrine lineage which are present from the differentiation stage around or after Ngn3 expression occurs and remains the fully mature endocrine cells including the beta cell. Accordingly, DISP2, SEZ6L2, LRP11 and SLC30A8 provide additional extracellular markers of pancreatic cells at a stage of differentiation where the cells are committed to the endocrine lineage and have lost the potential to become ductal or acinar cells.

Pancreatic Endocrine Cells—and Their Progenitors

In the pancreas several different types of pancreatic cells may be found. These cells include for example multi-potent pancreatic progenitor cells, ductal/endocrine progenitor cells, endocrine pre-progenitor cells, endocrine progenitor cells, early endocrine cells, and/or fully differentiated endocrine cells. A schematic overview of these cell types can be found in FIG. 1.

"Pancreatic endocrine cell" or "pancreatic hormone expressing cell" as used interchangeably herein refers to a cell capable of expressing at least one of the following hormones: insulin, glucagon, somatostatin, pancreatic polypeptide, and ghrelin.

"Pancreatic hormone secreting cell" as used herein refers to a pancreatic endocrine cell capable of secreting at least one of the following hormones: insulin, glucagon, somatostatin, pancreatic polypeptide, and ghrelin.

"Pancreatic endocrine pre-progenitor cells" (also termed "pancreatic endocrine pre-progenitors" and "endocrine pre-progenitors") as used herein are cells, which have lost their potential of developing into pancreatic ductal and acinar cells, have not yet expressed Ngn3 protein, and are not hormone expressing, but which have the potential to differentiate into pancreatic endocrine cells or pancreatic hormone secreting cells, and which do normally also share at least part of the phenotype characteristic of these cells. In some aspects endocrine pre-progenitor cells are $Pdx1^+$, $Nkx6.1^+$, $Ddr1^+$ and $Dner^+$.

"Pancreatic endocrine progenitor cells" (also termed "pancreatic endocrine progenitors" and "endocrine progenitors") as used herein are cells, which are Ngn3 protein expressing cells but not hormone expressing, but which have the potential to differentiate into pancreatic endocrine cells or pancreatic hormone secreting cells, and which do normally also share at least part of the phenotype characteristic of these cells. In some aspects endocrine progenitor cells are $Pdx1^+$, $Nkx6.1^+$, $Ngn3^+$, $Ddr1^+$ and $Dner^{+/\pm}$. In some aspects endocrine progenitor cells are $Pdx1^+$, $Nkx6.1^+$, $Ddr1^+$, $Ngn3^{+/low/-}$ and $Dner^{+/low-}$. In some aspects endocrine progenitor cells are $Pdx1^+$, $Nkx6.1^+$, $Ddr1^{+/low/-}$ and $Ngn3^+$.

"Early endocrine cells" (also termed "pancreatic early endocrine cells") as used herein are endocrine cells which have turned off Ngn3 but do not share all the characteristics of fully differentiated pancreatic endocrine cells found in the Islet of Langerhans in the adult pancreas, such as responsiveness to glucose. The early endocrine cells may be negative or positive for one or more of the pancreatic endocrine hormones (insulin, glucagon, somatostatin, pancreatic polypeptide, and ghrelin). In some aspects early endocrine cells are $Pdx1^{+/-}$, $Nkx6.1^{+/-}$, $hormone^+$, $Ddr1^{+/-}$ and $Dner^{+/-}$. In some aspects early endocrine cells are $Pdx1^{high/+}$, $Nkx6.1^+$, $hormone^{+/-}$, $Ddr1^{+/low/-}$ and $Dner^{+/low/-}$.

"Fully differentiated endocrine cells" (also termed "pancreatic mature endocrine cells") as used herein are cells which share all the characteristics of fully differentiated pancreatic endocrine cells found in the Islet of Langerhans in the adult pancreas. "Pancreatic hormone expressing cells" and "pancreatic hormone secreting cells" are considered as "pancreatic endocrine cells" ranging from the early to the fully differentiated phenotype. In some aspects fully differentiated endocrine cells are $Pdx1^{+/-}$, $Nkx6.1^{+/-}$, $hormone^+$, $Ddr1^-$ and $Dner^{-low}$. In some aspects fully differentiated endocrine cells are $Pdx1^+$, $Nkx6.1^{+/-}$, $hormone^+$ and $Dner^{low/-}$.

"beta cell lineage" as used herein refer to cells with positive gene expression for the transcription factor Pdx1 and at least one of the following transcription factors: Ngn3, Nkx2.2, Nkx6.1, NeuroD, Isl1, Hnf3 beta, MafA, Pax4, and Pax6. Cells expressing markers characteristic of the beta cell lineage include beta cells.

"Ductal/endocrine progenitor cells" as used herein are cells which during early pancreas development reside in the central part and retain the bi-potential of becoming mature ductal cells or fully differentiated endocrine cells. Furthermore, these cells express the transcription factors Pdx1 and Nkx6.1 and not Ptf1a. An example of ductal/endocrine progenitor cells can be found at development stage around e12.0 in the mouse. In some aspects ductal/endocrine rogenitor cells endocrine pre-progenitor cells are $Pdx1^+$, $Nkx6.1^+$, $Ddr1^{+/-}$.

"Multi-potent pancreatic progenitor cells" as used herein are cells which represents the earliest cells for the pancreas. These cells are uniquely characterized as the triple positive cells for the 3 key transcription factors: $Pdx1^+/Nkx6.1^+/Ptf1a^+$.

"Markers" as used herein, are nucleic acid or polypeptide molecules that are differentially expressed in a cell of interest. In this context, differential expression means an increased level for a positive marker and a decreased level for a negative marker. The detectable level of the marker nucleic acid or polypeptide is sufficiently higher or lower in the cells of interest compared to other cells, such that the cell of interest can be identified and distinguished from other cells using any of a variety of methods known in the art.

In some aspects the pancreatic endocrine cells obtained by the method according to the invention are insulin producing cells, optionally together with cells differentiated towards glucagon, somatostatin, pancreatic polypeptide, and/or ghrelin producing cells. As used herein, "insulin producing cells" refers to cells that produce and store or secrete detectable amounts of insulin. "Insulin producing cells" can be individual cells or collections of cells.

In some aspects the pancreatic DNER+ cells obtained by the method according to the invention comprise early endocrine cells. In some aspects the pancreatic DNER+ cells obtained by the method according to the invention comprise endocrine progenitor cells. In some aspects the pancreatic DNER+ cells obtained by the method according to the invention might be 1) non-dividing cells that are able to mature into endocrine cells; 2) dividing cells that are able to be expanded a limited number of times before maturation; 3) dividing cells that are able to undergo cell division and to be passaged from one culture vessel to another over time. In some aspects a culture of pancreatic cells that exhibits DNER as a cell surface marker refers to a culture of enriched in pancreatic cells comprising cells selected from the group consisting of endocrine pre-progenitor cells, endocrine progenitor cells, early endocrine cells, and/or fully differentiated endocrine cells that, in addition to detectable DNER cell surface expression, is capable of differentiation into fully differentiated pancreatic endocrine cells, including insulin-producing pancreatic beta cells.

In some aspects the pancreatic DNER, DISP2, SEZ6L2, LRP11 and/or SLC30A8 positive cells obtained by the method according to the invention comprise early endocrine cells. In some aspects the pancreatic DNER, DISP2, SEZ6L2, LRP11 and/or SLC30A8 positive cells obtained by the method according to the invention comprise endocrine progenitor cells. In some aspects the pancreatic DNER, DISP2, SEZ6L2, LRP11 and/or SLC30A8 positive cells obtained by the method according to the invention might be 1) non-dividing cells that are able to mature into endocrine cells; 2) dividing cells that are able to be expanded a limited number of times before maturation; 3) dividing cells that are able to undergo cell division and to be passaged from one culture vessel to another over time. In some aspects a culture of pancreatic cells that exhibits DNER, DISP2, SEZ6L2, LRP11 and/or SLC30A8 as a cell surface marker refers to a culture of enriched in pancreatic cells comprising cells selected from the group consisting of endocrine pre-progenitor cells, endocrine progenitor cells, early endocrine cells, and/or fully differentiated endocrine cells that, in addition to detectable DNER, DISP2, SEZ6L2, LRP11 and/or SLC30A8 cell surface expression, is capable of differentiation into fully differentiated pancreatic endocrine cells, including insulin-producing pancreatic beta cells.

"Passage" of cells usually refers to a transition of a seeded culture container from a partially confluent state to a confluent state, at which point they are removed from the culture container and reseeded in a culture container at a lower density. However, cells may be passaged prior to reaching confluence. Passage typically results in expansion of the cell population as they grow to reach confluence. The expansion of the cell population depends on the initial seeding density but is typically a 1 to 10, 1 to 5, 1 to 3, or 1 to 2 fold expansion. Thus, passaging generally requires that the cells be capable of a plurality of cell divisions in culture.

Cell Population Comprising Pancreatic Cells

The term "a cell population comprising pancreatic cells" as used herein refers to a population of cells comprising one or more cell types selected from the group consisting of acinar and ductal cells, multi-potent pancreatic progenitor cells, ductal/endocrine progenitor cells, pancreatic endocrine pre-progenitor cells, pancreatic endocrine progenitor cells, early pancreatic endocrine cells, pancreatic endocrine cells, pancreatic hormone secreting cells, fetal pancreatic cells, adult pancreatic cells and other non-pancreatic cells. A "population" of cells refers to a plurality of cells obtained by a particular isolation of the starting cells or culture procedure. Properties of a cell population are generally defined by a percentage of individual cells having the particular property (e.g., the percentage of cells staining positive for a particular marker) or the bulk average value of the property when measured over the entire population (e.g., the amount of mRNA in a lysate made from a cell population, or percentage of cells positive for a histochemically detectable marker, such as Ngn3, Pax6, insulin or glucagon).

In some aspects the cell population comprising pancreatic cells is obtained from a pancreas. In some aspects the cell population comprising pancreatic cells is obtained from a fetal pancreas or an adult pancreas. In some aspects the pancreas is from a mammal, such as a human.

In some aspects the cell population comprising pancreatic cells is obtained from a somatic cell population. In some aspects the somatic cell population has been induced to de-differentiate in to an embryonic-like stem (ES, e.g., a pluripotent) cell. Such de-differentiated cells are also termed induced pluripotent stem cells (IPS).

In some aspects the cell population comprising pancreatic cells is obtained from embryonic stem (ES, e.g., pluripotent) cells. In some aspects the cell population comprising pancreatic cells is pluripotent cells such as ES like-cells.

In some aspects the cell population comprising pancreatic cells is embryonic differentiated stem (ES or pluripotent) cells. Differentiation takes place in embryoid bodies and/or in monolayer cell cultures or a combination thereof.

In some aspects the cell population comprising pancreatic cells is of mammalian origin. In some aspects the cell population comprising pancreatic cells is of human origin. In some aspects the cell population has been differentiated to the pancreatic endocrine lineage.

In some aspects the cell population comprising pancreatic cells is obtained from one or more donated pancreases. The methods described herein are not dependent on the age of the donated pancreas. Accordingly, pancreatic material isolated from donors ranging in age from embryos to adults can be used.

Once a pancreas is harvested from a donor, it is typically processed to yield individual cells or small groups of cells for culturing using a variety of methods. One such method calls for the harvested pancreatic tissue to be cleaned and prepared for enzymatic digestion. Enzymatic processing is used to digest the connective tissue so that the parenchyma of the harvested tissue is dissociated into smaller units of pancreatic cellular material. The harvested pancreatic tissue is treated with one or more enzymes to separate pancreatic cellular material, substructures, and individual pancreatic cells from the overall structure of the harvested organ. Collagenase, DNAse, Liberase preparations (see U.S. Pat. Nos. 5,830,741 and 5,753,485) and other enzymes are contemplated for use with the methods disclosed herein.

Isolated source material can be further processed to enrich for one or more desired cell populations. However, unfractionated pancreatic tissue, once dissociated for culture, can also be used directly in the culture methods of the invention without further separation. In some aspects the isolated pancreatic cellular material is purified by centrifugation through a density gradient (e.g., Nycodenz, Ficoll, or Percoll). For example the gradient method described in U.S. Pat. No. 5,739,033, can be used as a means for enriching the processed pancreatic material in islets. The mixture of cells harvested from the donor source will typically be heterogeneous and thus contain alpha cells, beta cells, delta cells, epsilon cells, ductal cells, acinar cells, facultative progenitor cells, and other pancreatic cell types.

A typical purification procedure results in the separation of the isolated cellular material into a number of layers or interfaces. Typically, two interfaces are formed. The upper interface is Islet-enriched and typically contains 10 to 100% islet cells in suspension. The second interface is typically a mixed population of cells containing islets, acinar, and ductal cells. The bottom layer is the pellet, which is formed at the bottom of the gradient. This layer typically contains primarily acinar cells, some entrapped islets, and some ductal cells. Ductal tree components can be collected separately for further manipulation. The cellular constituency of the fractions selected for further manipulation will vary depending on which fraction of the gradient is selected and the final result of each isolation.

When islet cells are the desired cell type, a suitably enriched population of islet cells within an isolated fraction will contain at least 10% to 100% islet cells. Other pancreatic cell types and concentrations can also be harvested following enrichment. For example, the culture methods described herein can be used with cells isolated from the second interface, from the pellet, or from other fractions, depending on the purification gradient used.

In some aspects intermediate pancreatic cell cultures are generated from the islet-enriched (upper) fraction. Additionally, however, the more heterogeneous second interface and the bottom layer fractions that typically contain mixed cell populations of islets, acinar, and ductal cells or ductal tree components, acinar cells, and some entrapped Islet cells, respectively, can also be used in culture. In some aspects, while both layers contain cells capable of giving rise to the DNER and/or DDR1 positive population described herein, each layer may have particular advantages for use with the disclosed methods. In some aspects, while both layers contain cells capable of giving rise to the DNER, DISP2, SEZ6L2, LRP11, SLC30A8 and/or DDR1 positive population described herein, each layer may have particular advantages for use with the disclosed methods.

In some aspects the cell population is a population of stem cells. In some aspects the cell population is a population of stem cells differentiated to the pancreatic endocrine lineage.

Stem cells are undifferentiated cells defined by their ability at the single cell level to both self-renew and differentiate to produce progeny cells, including self-renewing progenitors, non-renewing progenitors, and terminally differentiated cells. Stem cells are also characterized by their ability to differentiate in vitro into functional cells of various cell lineages from multiple germ layers (endoderm, mesoderm and ectoderm), as well as to give rise to tissues of multiple germ layers following transplantation and to contribute substantially to most, if not all, tissues following injection into blastocysts.

Stem cells are classified by their developmental potential as: (1) totipotent, meaning able to give rise to all embryonic and extraembryonic cell types; (2) pluripotent, meaning able to give rise to all embryonic cell types; (3) multi-potent, meaning able to give rise to a subset of cell lineages, but all within a particular tissue, organ, or physiological system (for example, hematopoietic stem cells (HSC) can produce progeny that include HSC (self-renewal), blood cell restricted oligopotent progenitors and all cell types and elements (e.g., platelets) that are normal components of the blood); (4) oligopotent, meaning able to give rise to a more restricted subset of cell lineages than multi-potent stem cells; and (5) unipotent, meaning able to give rise to a single cell lineage (e.g., spermatogenic stem cells).

A protocol for obtaining pancreatic cells from stem cells is exemplified by, but not limited to, the protocols described in D'Amour, K. A. et al. (2006), Nat Biotechnol 24, 1392-401; Jiang, J. et al. (2007), Stem Cells 25, 1940-53; and Kroon, E. et al. (2008), Nat Biotechnol 26, 443-452.

A protocol for obtaining pancreatic cells from somatic cells or somatic cells induced to de-differentiate into pluripotent cells such as ES like-cells is exemplified by, but not limited to, the protocols described in Aoi, T. et al. (2008), Science 321(no. 5889), 699-702; D'Amour, K. A. et al. (2006), Nat Biotechnol 24, 1392-401; Jiang, J. et al. (2007), Stem Cells 25, 1940-53; Kroon, E. et al. (2008), Nat Biotechnol 26, 443-452; Takahashi, K. et al. (2007), Cell 131, 861-72; Takahashi, K., and Yamanaka, S. (2006), Cell 126, 663-76; and Wernig, M. et al. (2007), Nature 448, 318-24.

Differentiation is the process by which an unspecialized ("uncommitted") or less specialized cell acquires the features of a specialized cell such as, for example, a nerve cell or a muscle cell. A differentiated or differentiation-induced cell is one that has taken on a more specialized ("committed") position within the lineage of a cell. The term "committed", when applied to the process of differentiation, refers to a cell that has proceeded in the differentiation pathway to a point where, under normal circumstances, it will continue to differentiate into a specific cell type or subset of cell types, and cannot, under normal circumstances, differentiate into a different cell type or revert to a less differentiated cell type. De-differentiation refers to the process by which a cell reverts to a less specialized (or committed) position within the lineage of a cell. As used herein, the lineage of a cell defines the heredity of the cell, i.e., which cells it came from and what cells it can give rise to. The lineage of a cell places the cell within a hereditary scheme of development and differentiation. A lineage-specific marker refers to a characteristic specifically associated with the phenotype of cells of a lineage of interest and can be used to assess the differentiation of an uncommitted cell to the lineage of interest.

As used herein "differentiate" or "differentiation" refers to a process where cells progress from an undifferentiated state to a differentiated state, from an immature state to a less immature state or from an immature state to a mature state. For example, early undifferentiated embryonic pancreatic cells are able to proliferate and express characteristics markers, like Pdx1, Nkx6.1, and Ptf1a. Mature or differentiated pancreatic cells do not proliferate and do secrete high levels of pancreatic endocrine hormones or digestive enzymes. E.g., fully differentiated beta cells secrete insulin at high levels in response to glucose. Changes in cell interaction and maturation occur as cells lose markers of undifferentiated cells or gain markers of differentiated cells. Loss or gain of a single marker can indicate that a cell has "matured or fully differentiated." The term "differentiation factor" refers to a compound added to pancreatic cells to enhance their differentiation to mature endocrine cells also containing insulin producing beta cells. Exemplary differentiation factors include hepatocyte growth factor, keratinocyte growth factor, exendin-4, basic fibroblast growth factor, insulin-like growth factor-1, nerve growth factor, epidermal growth factor platelet-derived growth factor, and glucagon-like peptide 1. In some aspects differentiation of the cells comprises culturing the cells in a medium comprising one or more differentiation factors.

Markers characteristic of the pancreatic endocrine lineage are selected from the group consisting of Ngn3, NeuroD, Islet-1, Pdx1, Nkx6.1, Nkx2.2, MafA, MafB, Arx, Brn4, Pax4, Pax6, Glut2, insulin, glucagon, somatostatin, pancreatic polypeptide (PP), and ghrelin. In some aspects a pancreatic endocrine cell is capable of expressing at least one of the following hormones: insulin, glucagon, somatostatin, PP, and ghrelin. Suitable for use in the present invention is a cell that expresses at least one of the markers characteristic of the pancreatic endocrine lineage. In some aspects of the present invention, a cell expressing markers characteristic of the pancreatic endocrine lineage is a pancreatic endocrine cell. The pancreatic endocrine cell may be a pancreatic hormone expressing cell. Alternatively, the pancreatic endocrine cell may be a pancreatic hormone secreting cell.

In some aspects of the present invention, the pancreatic endocrine cell is a cell expressing markers characteristic of the beta cell lineage. A cell expressing markers characteristic of the beta cell lineage expresses Pdx1 and at least one of the following transcription factors: Ngn3, Nkx2.2, Nkx6.1, NeuroD, Isl1, Hnf3 beta, MafA, Pax4, and Pax6. In some aspects of the present invention, a cell expressing markers characteristic of the beta cell lineage is a beta cell. In some aspects the pancreatic endocrine cell is a cell expressing the marker Nkx6.1. In some aspects the pancreatic endocrine cell is a cell expressing the marker Pdx1. In some aspects the pancreatic endocrine cell is a cell expressing the markers Nkx6.1 and Pdx1.

"Pdx1" as used herein refers to a homeodomain transcription factor implicated in pancreas development. In some aspects "Pax4" as used herein is a beta cell specific transcription factor and "Pax6" as used herein is a pancreatic islet cell (specific) transcription factor; both are implicated in Islet development. "Hnf3 beta" belongs to the hepatic nuclear factor family of transcription factors, which is characterized by a highly conserved DNA binding domain and two short carboxy-terminal domains. "Hnf3 beta" is also known as "FoxA2". "NeuroD" as used herein is basic helix-loop-helix (bHLH) transcription factor implicated in neurogenesis. "Ngn3" as used herein, is a member of the neurogenin family of basic loop-helix-loop transcription factors. "Nkx2.2" and "Nkx6.1" as used herein are members of the Nkx transcription factor family. "Islet-1" or "Isl1" as used herein is a member of the LIM/homeodomain family of transcription factors, and is expressed in the developing pancress. "MafA" as used herein is a transcription factor expressed in the pancreas, and controls the expression of genes involved in insulin biosynthesis and secretion.

Nkx6.1 and Pdx1 are co-expressed with Ptf1a in the early pancreatic multi-potent cell that can develop into all cell types found in the adult pancreas (e.g., acinar, ductal, and endocrine cells). Within this cell population cells that also transiently express Ngn3 are found. Once a cell expresses or has expressed Ngn3 it will be part of the endocrine lineage, giving rise to endocrine cells (one type being the insulin producing beta cell) that will later form the islets of Langerhans. In the absence of Ngn3 no endocrine cells form during pancreas development. As development progress Nkx6.1 and Pdx1 are co-expressed in the more central domain of the pancreas which now become devoid of Ptf1a expression and the Nkx6.1 and Pdx1 positive cells can no longer give rise to acinar cells. Within this Nkx6.1 and Pdx1 positive cell population a significant number of cells transiently co-express Ngn3, marking them for the endocrine lineage like earlier in development.

DNER

As used herein, "DNER", "Dner", "DNER protein", or "Dner protein" refers to all mammalian forms of DNER, including human and mouse. In some aspects "DNER", "Dner", "DNER protein", or "Dner protein" refers to all vertebrate forms of DNER. When used herein the term may be written fully in uppercase, "DNER", or with only the first letter in uppercase, "Dner", and shall mean the DNER from any mammal including human and mouse. The human form is known as: "delta/notch-like EGF repeat containing", also known as, e.g., "bet" and "UNQ26". The mouse form is known as: "delta/notch-like EGF-related receptor" also known as, e.g., "BET", "Bret", "MGC39059", and "A930026D19Rik". DNER contains a single transmembrane domain at its C-terminal end and is presumed to be a putative cell surface protein. It also contains a number EGF-like repeats in its extracellular domain and its cytoplasmic carboxy-teminal domain contains a tyrosine-based sorting motif. In both human and mouse it is 737 amino acids long, and the similarity between mouse and human is 90%. One family member has been identified in mouse. DNER acts as a ligand of Notch during cellular morphogenesis of Bergmann glia in the mouse cerebellum. DNER binds to Notch1 at cell-cell contacts and activate Notch signalling in vitro.

The amino acid sequence of human and mouse DNER is shown in SEQ ID NO: 1 and SEQ ID NO: 2, respectively. The amino acid sequence of DNER is 737 amino acids in both mouse and human. In some aspects DNER according to the invention is SEQ ID NO: 1. In some aspects DNER according to the invention is SEQ ID NO: 2.

In some aspects the term "DNER protein" encompasses proteins of 70, such as 80, 85, 90, 92, 94, percent identity. In some aspects the term DNER protein encompasses proteins of 95, such as 96, 97, 98 or 99, percent identity. In some aspects the percent identity is determined relative to a human or mouse form of the protein. The percent identity may be determined by aligning two sequences and determining the number of aligned identical residues minus the number of different residues divided by the total number of residues in the longer sequence and multiplied by 100.

"Human DNER protein" as used herein is naturally occurring on chromosome 2 at location 2q36.3 or 229.93-230.29 Mb. Human DNER protein has GenPept accession no. NP_620711.2.

"Mouse Dner protein" as used herein is naturally occurring on chromosome 1 at location 1 C5 or 84.25-84.58 Mb. Mouse Dner protein has GenPept accession no. NP_690879.1.

The term "DNER binding reagent" is used herein to refer to a compound that specifically binds to the DNER protein, or to molecules covalently linked to said protein, such as an antibody, an antibody fragment thereof, a synthetic, antibody derived molecule, which includes CDRs from antibodies that bind to the particular protein (such synthetic molecules may for example be a scFV, a multispecific antibody etc.), a lectin, interactions partners of the delta notch family and a small molecule or fragments thereof.

In some aspects the binding reagent is an antibody that specifically binds to the DNER protein. In some aspects the binding reagent is an antibody that specifically binds to natural carbohydrates that are posttranslationally linked to the DNER protein. As shown in Example 1 herein, carbohydrate modifications are likely to appear in a number of specific sites in the DNER amino acid sequence. In some aspects the binding reagent is a lectin that specifically binds to natural carbohydrate structures linked to the DNER protein. In some aspects the binding reagent is a ligand of the DNER protein. In some aspects the ligand of DNER is selected from the group consisting of the extracellular domain of Notch-1, -2, -3, and/or -4. In some aspects the binding reagent is a non-toxic fluorescently marked molecule that interacts with the DNER protein on the extra- or intracellular side of the plasma membrane. An "oligosaccharide linked to DNER" is a polysaccharide molecule that is covalently linked to the DNER protein. In some aspects the oligosaccharide is linked through a glycine (G) residue. In some aspects the oligosaccharide is linked through an asparagine (N) residue. In some aspects the oligosaccharide is linked through a threonine (T) residue. The term "lectin" refers to protein that recognizes specific carbohydrate molecules. In some aspects In some aspects the carbohydrate is all or part of an oligosaccharide linked to the DNER protein molecule. A "ligand" is a molecule that is specifically bound by a protein. The term also encompasses molecules that bind to a protein, for example, an antibody that specifically binds to a protein. In some aspects the ligand binds to a molecule that is covalently linked to a protein, for example, a carbohydrate or an oligosaccharide.

In some aspects the binding reagent is an antibody that specifically binds to the DNER protein. The term "DNER binding reagent" also encompasses compounds that are specifically bound by the DNER protein, for example the extracellular domain of Notch-1, -2, -3, and/or -4. The term "binding reagent" encompasses both naturally occurring antibodies and fragments thereof, as well as chimeric antibodies composed of elements from several species and also completely synthetic antibody-like molecules, such as scFVs and other synthetic molecules having the binding specificity of an antibody (as a consequence of inclusion of naturally occurring CDR sequences).

Binding reagents are used to identify or select cells that express a particular protein as a cell surface marker. For example, DNER binding reagents are used to identify or select cells that express DNER protein as a cell surface marker.

Cells that "exhibit" a DNER protein "as a cell surface marker" are cells that exhibit a sufficient quantity of the particular protein on the cell surface to allow the cells to be selected or picked out from a population of cells using specific binding reagents of the particular protein and methods described herein, such as FACS, immunocytochemistry, immunoadsorbtion, and panning. In some aspects the method is MACS. In some aspects a DNER antibody is used to select cells that "exhibit DNER as a cell surface marker".

In some aspects the DNER binding reagent is labelled with a fluorescent dye, such as selected from PE, cy2, cy3, cy5, or Alexa488. In some aspects the DNER binding reagent is labelled with a hapten such as DIG, biotin, an epitope such as FLAG, HA, or Myc.

In some aspects one or more additional binding reagents may be used in combination with DNER binding reagent either simultaneously or sequentially. In some aspects the additional binding reagent may be subjected to the same step(s) of analysis as the DNER binding reagent. In some aspects the additional binding reagent is selected from the group consisting of DDR1 protein, prominin 1 (also known as CD133), and CD49f. See, e.g., Sugiyama et al. (2007), PNAS 140(1): 175-180. In some aspects the additional binding reagent is DDR1.

DDR1

As used herein, "DDR1 protein", "Ddr1 protein", "DDR1" or "Ddr1" refers to a DDR/TKT type protein kinase, Discoidin Domain Receptor family, member 1. When used herein the term may be written fully in uppercase, "DDR1", or with only the first letter in uppercase, "Ddr1", and shall mean the Discoidin Domain Receptor family, member 1 from any mammal including human and mouse. In some aspects "DDR1 protein", "Ddr1 protein", "DDR1" or "Ddr1" refers to all vertebrate forms of DDR1. DDR1 is activated by various types of collagen, including types I through IV. Binding of collagen to DDR1 protein results in autophosphorylation and a delayed but sustained tyrosine kinase activation. DDR1 may function in cell-to-cell interaction or recognition. At least three mRNA variants, resulting in different protein isoforms of 876, 913 and 919 amino acids, have been reported in humans. In the mouse two isoforms have been reported of 874 and 911 amino acids, respectively. DDR1 protein has been shown to be overexpressed in human breast, ovarian, esophageal and pediatric brain tumors. The protein has an intracellular Receptor tyrosine kinases activity and is activated by various types of collagen. Its autophosphorylation is achieved by all collagens so far tested (type I to type VI and XI).

The amino acid sequence of mouse and human DDR1 is shown in SEQ ID NO: 3 to SEQ ID NO: 7, respectively.

| SEQ ID NO: | Origin | Type |
| --- | --- | --- |
| 3 | Human | DDR1 isoform a |
| 4 | Human | DDR1 isoform b |
| 5 | Human | DDR1 isoform c |
| 6 | Mouse | DDR1 isoform 1 |
| 7 | Mouse | DDR1 isoform 2 |

In some aspects DDR1 according to the invention is SEQ ID NO: 3. In some aspects DDR1 according to the invention is SEQ ID NO: 4. In some aspects DDR1 according to the invention is SEQ ID NO: 5. In some aspects DDR1 according to the invention is SEQ ID NO: 6. In some aspects DDR1 according to the invention is SEQ ID NO: 7.

In some aspects the term "DDR1 protein" encompasses proteins of 70, such as 80, 85, 90, 92, 94, percent identity. In some aspects the term DDR1 protein encompasses proteins of 95, such as 96, 97, 98 or 99, percent identity. In some aspects the percent identity is determined relative to a human or mouse form of the protein. The percent identity may be determined by aligning two sequences and determining the number of aligned identical residues minus the number of different residues divided by the total number of residues in the longer sequence and multiplied by 100.

"Human DDR1 protein" as used herein is naturally occurring on chromosome c6 COX at location 30.99-31.01 Mb or on chromosome 6 at location 6p21.3. Human DDR1 protein isoform a has GenPept accession no. NP_054699.2. Human DDR1 protein isoform b has GenPept accession no. NP_001945.3. Human DDR1 protein isoform c has GenPept accession no. NP_054700.2.

"Mouse Ddr1 protein" as used herein is naturally occurring on chromosome 17 at location 35.29-35.31 Mb or 17 C; 17 21.5 cM. Mouse DDR1 protein isoform 1 has GenPept accession no. NP_031610.2. Mouse DDR1 protein isoform 2 has GenPept accession no. NP_766550.1.

It is noted that the terms "isoform" and "isotype" are used interchangeably herein referring to different forms of the same protein formed, e.g., because of single nucleotide polymorphisms, wherein different forms of a protein may be produced from related genes or may arise from the same gene by alternative splicing.

The term "DDR1 binding reagent" is used herein to refer to a compound that specifically binds to a DDR1 protein or to molecules covalently linked to a DDR1 protein, such as an antibody, an antibody fragment thereof, a synthetic, antibody derived molecule, which includes CDRs from DDR1 binding antibodies (such synthetic molecules may for example be a scFV, a multispecific antibody etc), a lectin, collagen types and a small molecule or fragments thereof.

In some aspects the DDR1 binding reagent is an antibody that specifically binds to the DDR1 protein. In some aspects the DDR1 binding reagent is an antibody that specifically binds to natural carbohydrates that are posttranslationally linked to the DDR1 protein; as shown in Example 1 herein, carbohydrates are likely to appear in a number of specific sites in the DDR1 amino acid sequence. In some aspects the DDR1 binding reagent is a lectin that specifically binds to natural carbohydrate structures linked to the DDR1 protein. In some aspects the DDR1 binding reagent is a ligand of the DDR1 protein. In some aspects the ligand is selected from the group consisting of collagens I-XI, Transthyretin, Transmembrane 4 superfamily, member 1 (TM4SF1). In some aspects the DDR1 binding reagent is a non-toxic fluorescently marked molecule that interacts with DDR1 on the extra- or intracellular side of the plasma membrane. An "oligosaccharide linked to DDR1" is a polysaccharide molecule that is covalently linked to the DDR1 protein. In some aspects the oligosaccharide is linked through an asparagine residue. The term "lectin" refers to protein that recognizes specific carbohydrate molecules. In some aspects the carbohydrate is all or part of an oligosaccharide linked to a DDR1 protein molecule. A "ligand" is a molecule that is specifically bound by a protein. The term also encompasses molecules that bind to a protein, for example, an antibody that specifically binds to a protein. In some instances the ligand binds to a molecule that is covalently linked to a protein, for example, a carbohydrate or an oligosaccharide.

In some aspects the DDR1 binding reagent is an antibody that specifically binds to the DDR1 protein. The term "DDR1 binding reagent" also encompasses compounds that are specifically bound by the DDR1 protein, for example collagen and collagen fragments. The term encompasses both naturally occurring antibodies and fragments thereof, as well as chimeric antibodies composed of elements from several species and also completely synthetic antibody-like molecules such as scFVs and other synthetic molecules having the binding specificity of an antibody (as a consequence of inclusion of naturally occurring CDR sequences)

DDR1 binding reagents are used to identify or select cells that express DDR1 protein as a cell surface marker.

Cells that "exhibit DDR1 as a cell surface marker" are cells that exhibit a sufficient quantity of DDR1 on the cell surface to allow the cells to be selected or picked out from a population of cells using DDR1 specific binding reagents and methods described herein, such as FACS, immunocytochemistry, immunoadsorbtion, and panning. In some aspects the method is MACS. In some aspects a DDR1 antibody is used to select cells that "exhibit DDR1 as a cell surface marker."

In some aspects the DDR1 binding reagent is labelled with a fluorescent dye, such as selected from PE, cy2, cy3, cy5, or Alexa488. In some aspects the DDR1 binding reagent is labelled with a hapten such as DIG, biotin, an epitope such as FLAG, HA, or Myc.

Further aspects relating to DDR1 and DDR1 binding reagents and the use hereof are described in PCT/EP2008/068061 which is incorporated herein by reference.

Further Extracellular Markers

As used herein, "DISP2", "Disp2", "DISP2 protein", "Disp2 protein" refer to a protein which is an extracellular marker of the endocrine lineage mainly found after the occurrence of Ngn3 expression and remains in the fully mature pancreatic endocrine cells including the beta cell. However, some cells are found to co-express DISP2 and Ngn3. When used herein the term may be written fully in uppercase, "DISP2", or with only the first letter in uppercase, "Disp2", and shall mean the DISP2 from any vertebrate including mammal, human and mouse. Disp2 is also known as "dispatched B" or "dispatched homolog 2". Disp2 has Gen-Pept reference no. NP_277045 in human and NP_733481 in mouse. The gene encoding the Disp2 protein has GeneID no. 85455 in human and 214240 in mouse.

As used herein, "SEZ6L2", "Sez6l2", "SEZ6L2 protein" or "Sez6l2 protein" refer to a protein which is an extracellular marker of the endocrine lineage mainly found after the occurrence of Ngn3 expression and remains in the fully mature pancreatic endocrine cells including the beta cell. However, some cells are found to co-express SEZ6L2 and Ngn3. When used herein the term may be written fully in uppercase, "SEZ6L2", or with only the first letter in uppercase, "Sez6l2", and shall mean the SEZ6L2 from any vertebrate including mammal, human and mouse. Sez6l2 is also known as "seizure related 6 homolog like 2" or "seizure related 6 homolog (mouse)-like 2". Two isoforms of Sez6l2 are found in human isoform 1 of Sez6l2 has GenPept reference no. NP_036542 and isoform 2 of Sez6l2 has GenPept reference no. NP_963869. Sez6l2 has GenPept reference no. NP_659175 in mouse. Sez6l2 has GenPept reference no. NP_659175 in mouse. The gene encoding the Sez6l2 protein has GeneID no. 26470 in human and 233878 in mouse.

As used herein, "LRP11", "Lrp11", "LRP11 protein" or "Lrp11 protein" refer to a protein which is an extracellular marker of the endocrine lineage mainly found after the occurrence of Ngn3 expression and remains in the fully mature pancreatic endocrine cell including the beta cell. However, some cells are found to co-express LRP11 and Ngn3. When used herein the term may be written fully in uppercase, "LRP11", or with only the first letter in uppercase, "Lrp11", and shall mean the LRP11 from any vertebrate including mammal, human and mouse. Lrp11 is also known as "low density lipoprotein receptor-related protein 11". Lrp11 has GenPept reference no. NP_116221 in human and NP_766372 in mouse. The gene encoding the Lrp11 protein has GeneID no. 84918 in human and 237253 in mouse.

As used herein, "SLC30A8", "Slc30a8", "SLC30A8 protein" or "Slc30a8 protein" refer to a protein which is an extracellular marker of the endocrine lineage mainly found after the occurrence of Ngn3 expression and remains in the fully mature pancreatic endocrine cells including the beta cell. When used herein the term may be written fully in uppercase, "SLC30A8", or with only the first letter in uppercase, "Slc30a8", and shall mean the SLC30A8 from any vertebrate including mammal, human and mouse. Slc30a8 is also known as "solute carrier family 30 (zinc transporter), member 8" or "solute carrier family 30 member 8". Slc30a8 has GenPept reference no. NP_776250 in human and NP_766404 in mouse. The gene encoding the Slc30a8 protein has GeneID no. 169026 in human and 239436 in mouse.

In some aspects the term DISP2, SEZ6L2, LRP11 or SLC30A8 protein encompasses proteins of 70, such as 80, 85, 90, 92, 94, percent identity. In some aspects the term DISP2, SEZ6L2, LRP11 or SLC30A8 protein encompasses proteins of 95, such as 96, 97, 98 or 99, percent identity. In some aspects the percent identity is determined relative to a human or mouse form of the protein. The percent identity may be determined by aligning two sequences and determining the number of aligned identical residues minus the number of different residues divided by the total number of residues in the longer sequence and multiplied by 100.

The terms "DISP2 binding reagent", "SEZ6L2 binding reagent", "LRP11 binding reagent" or "SLC30A8 binding reagent" is used herein to refer to a compound that specifically binds to a DISP2, SEZ6L2, LRP11 or SLC30A8 protein, respectively, or to molecules covalently linked to a DISP2, SEZ6L2, LRP11 or SLC30A8 protein, respectively, such as an antibody, an antibody fragment thereof, a synthetic, antibody derived molecule, which includes CDRs from DISP2, SEZ6L2, LRP11 or SLC30A8 binding antibodies, respectively (such synthetic molecules may for example be a scFV, a multispecific antibody etc), a lectin and a small molecule or fragments thereof.

In some aspects the DISP2, SEZ6L2, LRP11 or SLC30A8 binding reagent is an antibody that specifically binds to the DISP2, SEZ6L2, LRP11 or SLC30A8 protein, respectively. In some aspects the DISP2, SEZ6L2, LRP11 or SLC30A8 binding reagent is an antibody that specifically binds to natural carbohydrates that are posttranslationally linked to the DISP2, SEZ6L2, LRP11 or SLC30A8 protein, respectively. In some aspects the DISP2, SEZ6L2, LRP11 or SLC30A8 binding reagent is a lectin that specifically binds to natural carbohydrate structures linked to the DISP2, SEZ6L2, LRP11 or SLC30A8 protein, respectively. In some aspects the DISP2, SEZ6L2, LRP11 or SLC30A8 binding reagent is a ligand of the DISP2, SEZ6L2, LRP11 or SLC30A8 protein, respectively. In some aspects the ligand is selected from the group consisting of collagens I-XI, Transthyretin, Transmembrane 4 superfamily, member 1 (TM4SF1). In some aspects the DISP2, SEZ6L2, LRP11 or SLC30A8 binding reagent is a non-toxic fluorescently marked molecule that interacts with DISP2, SEZ6L2, LRP11 or SLC30A8, respectively, on the extra- or intracellular side of the plasma membrane. An "oligosaccharide linked to DISP2", "oligosaccharide linked to SEZ6L2", "oligosaccharide linked to LRP11" or "oligosaccharide linked to SLC30A8" is a polysaccharide molecule that is covalently linked to the DISP2, SEZ6L2, LRP11 or SLC30A8 protein, respectively. In some aspects the oligosaccharide is linked through an asparagine residue. The term "lectin" refers to protein that recognizes specific carbohydrate molecules. In some aspects the carbohydrate is all or part of an oligosaccharide linked to a DISP2, SEZ6L2, LRP11 or SLC30A8 protein molecule. A "ligand" is a molecule that is specifically bound by a protein. The term also encompasses molecules that bind to a protein, for example, an antibody that specifically binds to a protein. In some instances the ligand binds to a molecule that is covalently linked to a protein, for example, a carbohydrate or an oligosaccharide.

In some aspects the DISP2, SEZ6L2, LRP11 or SLC30A8 binding reagent is an antibody that specifically binds to the DISP2, SEZ6L2, LRP11 or SLC30A8 protein, respectively. The term "DISP2 binding reagent", "SEZ6L2 binding reagent", "LRP11 binding reagent" or "SLC30A8 binding reagent" also encompasses compounds that are specifically bound by the DISP2, SEZ6L2, LRP11 or SLC30A8 protein, respectively, for example collagen and collagen fragments. The term encompasses both naturally occurring antibodies and fragments thereof, as well as chimeric antibodies composed of elements from several species and also completely synthetic antibody-like molecules such as scFVs and other synthetic molecules having the binding specificity of an antibody (as a consequence of inclusion of naturally occurring CDR sequences)

DISP2, SEZ6L2, LRP11 or SLC30A8 binding reagents are used to identify or select cells that express DISP2, SEZ6L2, LRP11 or SLC30A8 protein, respectively, as a cell surface marker.

Cells that "exhibit DISP2 as a cell surface marker", "exhibit SEZ6L2 as a cell surface marker", "exhibit LRP11 as a cell surface marker", "exhibit SLC30A8 as a cell surface marker" are cells that exhibit a sufficient quantity of DISP2, SEZ6L2, LRP11 or SLC30A8, respectively, on the cell surface to allow the cells to be selected or picked out from a population of cells using DISP2, SEZ6L2, LRP11 or SLC30A8 specific binding reagents, respectively, and methods described herein, such as FACS, immunocytochemistry, immunoadsorbtion, and panning. In some aspects the method is MACS. In some aspects a DISP2, SEZ6L2, LRP11 or SLC30A8 antibody is used to select cells that "exhibit DISP2 as a cell surface marker", "exhibit SEZ6L2 as a cell surface marker", "exhibit LRP11 as a cell surface marker", "exhibit SLC30A8 as a cell surface marker", respectively.

In some aspects the DISP2, SEZ6L2, LRP11 or SLC30A8 binding reagent is labelled with a fluorescent dye, such as selected from PE, cy2, cy3, cy5, or Alexa488. In some aspects the DISP2, SEZ6L2, LRP11 or SLC30A8 binding reagent is labelled with a haptene such as DIG, biotin, an epitope such as FLAG, HA, or Myc.

In some aspects one or more of the markers selected from the group consisting of DISP2, SEZ6L2, LRP11 and SLC30A8 may be used in the methods of the invention in combination with DNER. In some aspects one or more binding reagents selected from the group consisting of DISP2, SEZ6L2, LRP11 and SLC30A8 binding reagent may be used in the methods of the invention in combination with DNER binding reagent.

In some aspects one or more of the markers selected from the group consisting of DISP2, SEZ6L2, LRP11 and SLC30A8 may be used in the methods of the invention in stead of the DNER. In some aspects one or more binding reagents selected from the group consisting of DISP2, SEZ6L2, LRP11 and SLC30A8 binding reagent may be used in the methods of the invention in stead of the DNER binding reagent.

In some aspects one or more of the markers selected from the group consisting of DISP2, SEZ6L2, LRP11 and SLC30A8 may be used in the methods of the invention in combination with DDR1 and in stead of the DNER. In some aspects one or more binding reagents selected from the group consisting of DISP2, SEZ6L2, LRP11 and SLC30A8 binding reagent may be used in the methods of the invention in combination with DDR1 binding reagent and in stead of the DNER binding reagent.

Methods of Identification

In some aspects the invention relates to a method of identification of cells comprising cells selected from the group consisting of endocrine pre-progenitor cells, endocrine progenitor cells, early endocrine cells, and/or fully differentiated endocrine cells, the method comprising contacting a cell population comprising pancreatic cells with a DNER binding reagent. In some aspects the number and/or ratio of cells that binds the DNER binding reagent, i.e. DNER positive cells, may be determined. In some aspects the invention relates to a method of identification of endocrine pre-progenitor cells, the method comprising contacting a cell population comprising pancreatic cells with a DNER binding reagent. In some aspects the invention relates to a method of identification of endocrine progenitor cells, the method comprising contacting a cell population comprising pancreatic cells with a DNER binding reagent. In some aspects the invention relates to a method of identification of cells comprising cells selected from the group consisting of endocrine pre-progenitor cells, endocrine progenitor cells, early endocrine cells, and/or fully differentiated endocrine cells, the method comprising contacting a cell population comprising pancreatic cells with a binding reagent selected from the group consisting of DNER, DISP2, SEZ6L2, LRP11 and SLC30A8 binding reagent. In some aspects the number and/or ratio of cells that binds a binding reagent selected from the group consisting of DNER, DISP2, SEZ6L2, LRP11 and SLC30A8 binding reagent, i.e. DNER, DISP2, SEZ6L2, LRP11 and/or SLC30A8 positive cells, may be determined. In some aspects the invention relates to a method of identification of endocrine pre-progenitor cells, the method comprising contacting a cell population comprising pancreatic cells with a binding reagent selected from the group consisting of DNER, DISP2, SEZ6L2, LRP11 and SLC30A8 binding reagent. In some aspects the invention relates to a method of identification of endocrine progenitor cells, the method comprising contacting a cell population comprising pancreatic cells with a binding reagent selected from the group consisting of DNER, DISP2, SEZ6L2, LRP11 and SLC30A8 binding reagent.

In some aspects the invention relates to a method of quantifying DNER positive cells comprising pancreatic cells by a) contacting the cells with a DNER binding reagent; and b) determining the quantity of cells that exhibit DNER as a cell surface marker (DNER positive cells). In some aspects the invention relates to a method of quantifying DNER, DISP2, SEZ6L2, LRP11 and/or SLC30A8 positive cells comprising pancreatic cells by a) contacting the cells with a binding reagent selected from the group consisting of DNER, DISP2, SEZ6L2, LRP11 and SLC30A8 binding reagent; and b) determining the quantity of cells that exhibit DNER, DISP2, SEZ6L2, LRP11 and/or SLC30A8 as a cell surface marker (DNER, DISP2, SEZ6L2, LRP11 and/or SLC30A8 positive cells).

Those skilled in the art will recognize that there are many methods to detect DNER, DISP2, SEZ6L2, LRP11, SLC30A8 and/or DDR1 protein. For example, antibodies that bind specifically to the DNER, DISP2, SEZ6L2, LRP11, SLC30A8 and/or DDR1 protein can be used to detect DNER, DISP2, SEZ6L2, LRP11, SLC30A8 and/or DDR1. Antibodies specific to the DNER, DISP2, SEZ6L2, LRP11, SLC30A8 and/or DDR1 protein are known to those skilled in the art and are commercially available from, for example, R&D Systems, Research Diagnostics, Inc.; Abcam; Ancell Immunology Research Products; eBioscience; the Developmental Studies Hybridoma Bank of the Univeristy of Iowa; and Zymed Laboratories, Inc., Abnova Corporation, Affinity BioReagents BioLegend, GeneTex Lifespan Biosciences, MBL International Novus Biologicals, Proteintech Group, Inc., Santa Cruz Biotechnology, Inc. Antibodies that recognize the extracellular portion of DNER, DISP2, SEZ6L2, LRP11, SLC30A8 and/or DDR1 may be used in the present invention for sorting cells. Different antibodies that recognize different epitopes on the extracellular portion of DNER, DISP2, SEZ6L2, LRP11, SLC30A8 and/or DDR1 may be used either alone or in combination. Any DNER, DISP2, SEZ6L2, LRP11, SLC30A8 and/or DDR1 binding reagents that recognize any part of DNER, DISP2, SEZ6L2, LRP11, SLC30A8 and/or DDR1 both in the extracellular domain, transmembrane domain and intracellular domain can be used for monitoring expression of DNER, DISP2, SEZ6L2, LRP11, SLC30A8 and/or DDR1. A person skilled in the art would realise that the description above or herein of detection of DNER, DISP2, SEZ6L2, LRP11, SLC30A8 and/or DDR1 protein would also apply to other extracellular proteins which may be contemplated for use as markers in the present invention.

Many different fluorescent molecules are available for conjugation to antibodies, for example fluorescien, cy2, cy3, cy5, PE, Alexa488, or rhodamine. Those skilled are aware that in some instances more than one extracellular marker can be detected by using different antibodies conjugated to fluorescent molecules. FACS analysis can be done under conditions to identify more than one extracellular marker of interest.

"Antibody" or "antibodies" refer to a polypeptide comprising a framework region from an immunoglobulin gene or fragments thereof that specifically binds and recognizes an antigen. Antibodies (also known as immunoglobulins) are proteins that are found in blood or other bodily fluids of vertebrates, and are used by the immune system to identify and neutralize foreign objects, such as bacteria and viruses. Although the general structure of all antibodies is very similar, a small region at the tip of the protein is extremely variable, allowing millions of antibodies with slightly different tip structures to exist. This region is known as the hypervariable region. Each of these variants can bind to a different target, known as an antigen. This huge diversity of antibodies allows the immune system to recognize an equally wide diversity of antigens. The unique part of the antigen recognized by an antibody is called an epitope. These epitopes bind with their antibody in a highly specific interaction, called induced fit, that allows antibodies to identify and bind only their unique antigen in the midst of the millions of different molecules that make up an organism.

Methods for assessing expression of protein and/or nucleic acid markers, such as mRNA, in cultured or isolated cells are standard in the art and include quantitative reverse transcription polymerase chain reaction (RT-PCR), Northern blots, and in situ hybridization (see, e.g., Current Protocols in Molecular Biology (Ausubel et al., eds. 2001 supplement)) and immunoassays, such as immunohistochemical analysis of sectioned material, Western blotting, and, for markers that are accessible in intact cells, flow cytometry analysis (FACS) (see, e.g., Harlow and Lane, Using Antibodies: A Laboratory Manual, New York: Cold Spring Harbor Laboratory Press (1998)). Conventional histochemical markers of endocrine cell differentiation may also be employed. Cells to be examined by immunohistochemistry may be cultured on glass chamber slides for microscopic examination. Alternatively, cells grown in conventional tissue culture may be manually removed from the culture and embedded in paraffin for sectioning. Alternatively, cells grown in conventional tissue culture may be manually, enzymatically or by use of enzyme free cell dissociation buffers removed from the culture and embedded in paraffin or TissueTech for sectioning or reincubated in media before embedding. Cell differentiation markers are varied and can be detected by conventional immunohistochemistry. A generally applicable protocol follows.

In some aspects cells in chamber slides may be very gently rinsed with in PBS and fixed for 45 minutes in 4% paraformaldehyde solution. Cells are then rinsed in PBS and stored at +5 until use. At the day of use cells are permeabilized through a graded series of ethanol (starting with 70% moving to 96%, then to 99%, then again 99%, then to 96%, and finally to 70%, using 5 minutes incubation with each concentration) then incubated in a blocking solution containing normal serum or TNB (from the TSA (Tyramide Signal Amplification) kit from Perkin Elmer) at room temperature. Primary antibodies are prepared at appropriate dilution and added to cells and incubated overnight (O/N) at room temperature (RT) in a moist chamber. Following incubation with primary antibody, cells are rinsed in PBS. Fluorescent secondary antibody prepared at appropriate dilution is added to the cells and incubated in the dark. With the secondary antibody DAPI dye might be included for counterstain of cell nuclei. Cells are then rinsed and excess fluid is removed and the chamber portion of the slides removed and slides are mounted with cover glass. The slides dry and are stored in the dark until inspection using a fluorescence microscope, such as a confocal microscope. In some aspects the staining process begins with removing chamber portion of the slides. Cells are very gently rinsed with in buffers and fixed in paraformaldehyde solution. Cells are then incubated in a blocking solution containing normal serum at room temperature. Cells are permeabilized with non-ionic detergent in blocking solution. Primary antibodies are prepared at appropriate dilution and added to cells and incubated. Following incubation with primary antibody, cells are rinsed in buffer. Secondary antibody prepared at appropriate dilution is added to the cells and incubated in the dark. Following incubation the cells are rinsed and nuclei were counterstained with DAPI. Excess fluid is removed and the slides are mounted and covered with cover slides. Alternatively, excess fluid is removed and the slides are mounted and covered with cover glass. The slides dry and are stored in the dark.

Alternatively the cells can be prepared for immunocytochemistry using the HRP method. In brief, the cells are embedded in paraffin and slides with paraffin sections are dried at 37° C. overnight. The cells are deparaffinized and immersed in a hydrogen peroxide solution to inhibit endogenous peroxidase activity. Slides are boiled in 0.01 M citrate buffer (pH 6.0) for 15 minutes to recover certain epitopes. Slides are rinsed with buffer and blocked using normal serum at room temperature in a moist chamber.

In some aspects primary antibody are added to the samples and incubated in a moist chamber. Slides are washed and incubated with biotin-secondary antibody. Slides were again rinsed with buffer and incubated with Avidin-HRP. Slides are again rinsed and incubated with TSA reagent to visualize primary antibody. In some aspects TSA is an abbreviation for tyramide signal amplification. Slides are mounted for viewing.

Alternatively, the cells can be prepared for immunocytochemistry using the HRP (horse-radish peroxidise) method. As secondary antibody a biotin coupled one is used. Slides were then rinsed with PBS and incubated with Avidin-HRP. Slides are again rinsed and incubated with TSA reagent to visualize primary antibody. In some aspects slides are mounted for visual inspection using conventional light microscopy. In some aspects slides are mounted for visual inspection using a fluorescence microscope, such as a confocal microscope. In some aspects the development may be carried out using a chromogene reagent, such as AEC.

For the identification of proteins in tissue sections the tissue may be fixed in 4% PFA (paraformaldehyde) O/N, then cryo-protected in 30% sucrose O/N and imbedded in TissueTech. Sections are then cut on a cryostate, air dried and stored at −80 degrees until use. Section are removed from the freezer and left at RT to thaw, next the sections are rinsed in PBS (phosphate buffered saline) and microwaved in 0.01 M citrate buffer (pH 6.0) for 15 minutes to recover epitopes. Such sections can then be stained using either method above or herein, but omitting the graded ethanol treatment. A hydrogen peroxide solution was used to inhibit endogenous peroxidase activity in the case of using the HRP based assay. In some aspects sections are then cut on a microtome, such as when using paraffin sections.

Analytical FACS sorting may be carried out on live cells or cells that have been fixed for 45 minutes in Lillys fixative. To remove supernatant cells are pelleted by 1400 rpm in 10 minutes at RT in 2 ml tubes. Alternatively, to remove supernatant cells are pelleted by 1300 rpm for 5 minutes at RT in 10 ml v-tubes. Following this cells are washed in PBS with 0.1% BSA. For fixed cells: Cells are blocked by adding serum to reach 10% serum (final concentration) from the animal where the secondary antibody is raised, block for 1 h. Cells are then pelleted and supernatant removed. Primary antibody solution is added and incubated O/N at RT. The next day cells are washed 3×5 minutes in 2 ml tubes (using 1.8 ml). Alternatively, the next day cells are washed 2×5 minutes in 10 ml v-tubes. Secondary antibody is added and incubated for 1 hour at RT. Cells are washed 3×5 min in PBS with 0.1% BSA (using 1.8 ml). Alternatively, cells are washed 2×5 min in PBS with 0.1% BSA. Finally, cells are assayed by FACS. Live cells: Primary antibody solution is added and incubated 1 hour at 4° C. Cells are washed 2×5 minutes in 10 ml v-tubes. Secondary antibody is added and incubated for 30 minutes at 4 degrees. Cells are washed 2×5 min in PBS with 0.1% BSA in 10 ml v-tubes. Finally, cells are fixed and assayed by FACS.

In some aspects identification of endocrine pre-progenitor cells, endocrine progenitor cells, early endocrine cells, and/or fully differentiated endocrine cells may be achieved by contacting the cell population with a DNER binding reagent and evaluating the staining. In some aspects identification of endocrine pre-progenitor cells may be achieved by contacting the cell population with a DNER binding reagent and evaluating the staining. In some aspects identification of endocrine progenitor cells may be achieved by contacting the cell population with a DNER binding reagent and evaluating the staining. This analysis may be carried out using a method such as fluorescence activated cell sorting (FACS), immunohistochemistry (IHC), western blot, PCR, or ELISA. In some aspects identification of endocrine pre-progenitor cells, endocrine progenitor cells, early endocrine cells, and/or fully differentiated endocrine cells may be achieved by contacting the cell population with a binding reagent selected from the group consisting of DNER, DISP2, SEZ6L2, LRP11 and SLC30A8 binding reagent and evaluating the staining. In some aspects identification of endocrine pre-progenitor cells may be achieved by contacting the cell population with a binding reagent selected from the group consisting of DNER, DISP2, SEZ6L2, LRP11 and SLC30A8 binding reagent and evaluating the staining. In some aspects identification of endocrine progenitor cells may be achieved by contacting the cell population with a binding reagent selected from the group consisting of DNER, DISP2, SEZ6L2, LRP11 and SLC30A8 binding reagent and evaluating the staining.

In some aspects the invention relates to an isolated cell selected from the group of endocrine pre-progenitor cells, endocrine progenitor cells, early endocrine cells and fully differentiated endocrine cells obtained by a method as defined herein. In some aspects the invention relates to an isolated endocrine pre-progenitor cell obtained by a method as defined herein. In some aspects the isolated cell is an endocrine pre-progenitor cell. In some aspects the invention relates to an isolated endocrine progenitor cells obtained by a method as defined herein. In some aspects the invention relates to an isolated fully differentiated endocrine cell obtained by a method as defined herein. In some aspects the invention relates to an isolated pancreatic beta cell obtained by a method as defined herein.

In some aspects the invention relates to the use of a DNER binding reagent to identify or select cells that express DNER protein as a cell surface marker. In some aspects the invention relates to the use of DNER protein as a cell surface marker to obtain a culture of pancreatic endocrine cells. In some aspects the invention relates to the use of a binding reagent selected from the group consisting of DNER, DISP2, SEZ6L2, LRP11 and SLC30A8 binding reagent to identify or select cells that express DNER, DISP2, SEZ6L2, LRP11 and/or SLC30A8 protein as a cell surface marker. In some aspects the invention relates to the use of DNER, DISP2, SEZ6L2, LRP11 and/or SLC30A8 protein as a cell surface marker to obtain a culture of pancreatic endocrine cells. In some aspects one or more further cell surface markers are used simultaneously or sequentially to obtain a culture of pancreatic endocrine cells. In some aspects a further cell surface marker is selected from the group consisting of DDR1 protein, prominin 1 (also known as CD133), and CD49f. In some aspects a further cell surface marker is DDR1 protein.

Methods of Separating

In some aspects the invention relates to a method of obtaining a culture of cells comprising cells selected from the group consisting of endocrine pre-progenitor cells, endocrine progenitor cells, early endocrine cells, and/or fully differentiated endocrine cells, the method comprising: contacting a cell population comprising pancreatic cells with a DNER binding reagent and separating the cells that binds the DNER binding reagent in a fraction of DNER positive cells from cells that do not bind the DNER binding reagent. In some aspects the invention relates to a method of obtaining a culture comprising endocrine pre-progenitor cells, the method comprising: contacting a cell population comprising pancreatic cells with a DNER binding reagent and separating the cells that binds the DNER binding reagent in a fraction of DNER positive cells from cells that do not bind the DNER binding reagent. In some aspects the invention relates to a method of obtaining a culture comprising endocrine progenitor cells, the method comprising: contacting a cell population comprising pancreatic cells with a DNER binding reagent and separating the cells that binds the DNER binding reagent in a fraction of DNER positive cells from cells that do not bind the DNER binding reagent. In some aspects the invention relates to a method of obtaining a culture of cells comprising cells selected from the group consisting of endocrine pre-progenitor cells, endocrine progenitor cells, early endocrine cells, and/or fully differentiated endocrine cells, the method comprising: contacting a cell population comprising pancreatic cells with a binding reagent selected from the group consisting of DNER, DISP2, SEZ6L2, LRP11 and SLC30A8 binding reagent and separating the cells that binds a binding reagent selected from the group consisting of DNER, DISP2, SEZ6L2, LRP11 and SLC30A8 binding reagent in a fraction of DNER, DISP2, SEZ6L2, LRP11 and/or SLC30A8 positive cells from cells that do not bind a binding reagent selected from the group consisting of DNER, DISP2, SEZ6L2, LRP11 and SLC30A8 binding reagent. In some aspects the invention relates to a method of obtaining a culture comprising endocrine pre-progenitor cells, the method comprising: contacting a cell population comprising pancreatic cells with a binding reagent selected from the group consisting of DNER, DISP2, SEZ6L2, LRP11 and SLC30A8 binding reagent and separating the cells that binds a binding reagent selected from the group consisting of DNER, DISP2, SEZ6L2, LRP11 and SLC30A8 binding reagent in a fraction of DNER, DISP2, SEZ6L2, LRP11 and/or SLC30A8 positive cells from cells that do not bind the DNER binding reagent. In some aspects the invention relates to a method of obtaining a culture comprising endocrine progenitor cells, the method comprising: contacting a cell population comprising pancreatic cells with a binding reagent selected from the group consisting of DNER, DISP2, SEZ6L2, LRP11 and SLC30A8 binding reagent and separating the cells that binds a binding reagent selected from the group consisting of DNER, DISP2, SEZ6L2, LRP11 and SLC30A8 binding reagent in a fraction of DNER, DISP2, SEZ6L2, LRP11 and/or SLC30A8 positive cells from cells that do not bind a binding reagent selected from the group consisting of DNER, DISP2, SEZ6L2, LRP11 and SLC30A8 binding reagent.

In some aspects the step of separating is done by fluorescence activated cell sorting (FACS). In some aspects the method is MACS. In some aspects the step of separating is done by panning.

FACS can also be used to physically separate cell populations based on measurement of fluorescence. The flowing cells are deflected by electromagnetic fields whose strength and direction are varied according to the measured intensity of the fluorescence signal. Labelled DNER, DISP2, SEZ6L2, LRP11 and/or SLC30A8 positive cells can be deflected into a separate container and thus, separated from unlabeled DNER, DISP2, SEZ6L2, LRP11 and/or SLC30A8 negative cells.

In some aspects fluorescently labelled molecules that bind specifically to DNER, DISP2, SEZ6L2, LRP11 and/or SLC30A8, most commonly antibodies, are used to select DNER, DISP2, SEZ6L2, LRP11 and/or SLC30A8 positive cells in conjunction with a FACS. Briefly, In some aspects a cell population comprising pancreatic cells are incubated with fluorescently labelled antibody and after the antibody binding, the cells are analyzed by FACS. The cell sorter passes single cells suspended in liquid through a fluorimeter. The amount of fluorescence is measured and cells with fluorescence levels detectably higher than control, unlabeled, cells are selected as positive cells.

In some aspects, wherein the cell population comprising pancreatic cells are isolated from pancreas, the cells are first cultured for one or more passages and then labelled with a DNER, DISP2, SEZ6L2, LRP11 and/or SLC30A8 specific antibody. The cells are then scanned using FACS to separate DNER, DISP2, SEZ6L2, LRP11 and/or SLC30A8 positive from DNER, DISP2, SEZ6L2, LRP11 and/or SLC30A8 negative cells. While this example has discussed FACS analysis with labelled antibodies, other molecules that specifically bind to DNER, DISP2, SEZ6L2, LRP11 and/or SLC30A8, e.g., lectins and other DNER binding partners, such as listed above or herein, can also be used to practice the invention. In some aspects the method of separating DNER, DISP2, SEZ6L2, LRP11 and/or SLC30A8 positive cells from DNER, DISP2, SEZ6L2, LRP11 and/or SLC30A8 negative cells is by affinity adsorbing DNER, DISP2, SEZ6L2, LRP11 and/or SLC30A8 positive cells onto a solid support. DNER, DISP2, SEZ6L2, LRP11 and/or SLC30A8 positive cells can also be separated from DNER, DISP2, SEZ6L2, LRP11 and/or SLC30A8 negative cells by using DNER, DISP2, SEZ6L2, LRP11 and/or SLC30A8 specific binding molecules attached to a solid support. Those skilled in the art will recognize that DNER, DISP2, SEZ6L2, LRP11 and/or SLC30A8 specific antibodies can be bound to a solid support through an antibody binding molecule, such as protein G or protein A or alternatively, can be conjugated to a solid support directly. Solid supports with attached DNER, DISP2, SEZ6L2, LRP11 and/or SLC30A8 antibodies are commercially available, e.g., StemSep and EasySep™, magnetic beads, both from Stem Cell Technologies. In some aspects the step of separating may be carried out using magnetic activated cell sorting (MACS).

DNER, DISP2, SEZ6L2, LRP11 and/or SLC30A8 positive cells can also be separated from DNER, DISP2, SEZ6L2, LRP11 and/or SLC30A8 negative cells through the technique of panning. Panning is done by coating a solid surface with a binding reagent selected from the group consisting of DNER, DISP2, SEZ6L2, LRP11 and SLC30A8 binding reagent and incubating pancreatic cells on the surface for a suitable time under suitable conditions. A flat surface, e.g., a culture dish, is coated with a binding reagent selected from the group consisting of DNER, DISP2, SEZ6L2, LRP11 and SLC30A8 binding reagent. Pancreatic cells are added to the surface and allowed to bind to the binding reagent selected from the group consisting of DNER, DISP2, SEZ6L2, LRP11 and SLC30A8 binding reagent. The culture dishes are then washed, removing the DNER, DISP2, SEZ6L2, LRP11 and/or SLC30A8 negative cells from the dish. In some aspects a DNER, DISP2, SEZ6L2, LRP11 and/or SLC30A8 specific antibody is used to coat a culture dish and "pan" for DNER, DISP2, SEZ6L2, LRP11 and/or SLC30A8 positive cells in a population of pancreatic cells.

In some aspects the cells may be purified before or after selection by DNER, DISP2, SEZ6L2, LRP11 and/or SLC30A8 by separating cells into Ptprn/IA2-positive and Ptprn/IA2-negative cells. In some aspects the cells may be purified before or after selection by DNER, DISP2, SEZ6L2, LRP11 and/or SLC30A8 by separating cells into Ptprn/IA2-positive and Ptprn-negative cells. In some aspects the cells may be separated into Abcc8/Sur1-positive and Abcc8/Sur1-negative cells. In some aspects the cells may be separated into Slc30a8/ZnT-8-positive and Slc30a8/ZnT-8-negative cells. In some aspects the cells may be purified before or after selection by DNER in combination with one or more further extracellular markers, such as DDR1 protein. In some aspects the cells may be purified before or after selection by DNER, DISP2, SEZ6L2, LRP11 and/or SLC30A8 in combination with one or more further extracellular markers, such as DDR1 protein.

So, the invention includes aspects wherein the cell population comprising pancreatic cells is a beta cell-positive fraction, including a Ptprn-positive fraction, an Abcc8-positive fraction, and/or a Slc30a8-positive fraction. Also, the culture of pancreatic endocrine cells obtained by the method according to any of the embodiments above or herein may be further separated in a beta cell-positive/negative fraction, including a Ptprn-positive/negative fraction, an Abcb9-positive/negative fraction, and/or a Slc30a8-positive/negative fraction.

A person skilled in the art will realise that all details in the section above or herein relating to methods of separating, although explicitly stated for DNER, DISP2, SEZ6L2, LRP11 and/or SLC30A8, may also be applied to other extracellular proteins. Such extracellular protein include proteins selected from the group consisting of DDR1, prominin 1 (also known as CD133), and CD49f. Specifically, such extracellular protein may be DDR1.

During differentiation of embryonic stem (ES) cells into beta cells it is expected that other cells types, such as, e.g., neural cells, and non-pancreatic endoderm will also be produced. ES cells can be differentiated to endodermal cells by activin A and then to pancreatic cells. Once the pancreatic fate has been acquired the wanted cells can be isolated. DNER and/or DDR1 can then be used as marker(s) to isolate the wanted subset of cells. A DNER binding reagent will specifically bind to the endocrine pre-progenitor cells of the pancreas and their progeny but also to neural cells in general. The inventors have conducted gene expression profiling experiments which show that DNER is not a marker for intestinal endocrine progenitor cells. A DDR1 binding reagent will also bind to the ductal/endocrine progenitor cells of the pancreas as well as the endocrine pre-progenitor cells, endocrine progenitor cells, and early endocrine cells. In addition, a DDR1 binding reagent will not bind to neural cells but do bind to other endodermal cells than pancreatic cells.

Various strategies for identification, enrichment, and/or selection are available, such as the following example: ES cells that have been induced to differentiate into definitive endoderm including pancreatic endoderm can be subjected to 1) the use of DDR1 as a marker to isolate DDR1+ cells followed by; 2) the use of DNER as a marker to isolate DNER+ cells from the DDR1+ population. This step will allow direct isolation of the ES-derived pool of cells that can be designated pancreatic endocrine pre-progenitors. Upon further in vitro mediated differentiation of such cells the subsequent use markers of, e.g., Ptprn/IA2-, Abcc8/Sur1-, or Slc30a8/ZnT-8-positive cells as markers can be used to isolate early and fully differentiated endocrine cells.

A portion of the DDR1 positive cells are expected to have the ability to proliferate. Accordingly, in some aspects the invention relates to a method comprising the steps of a) the use of a DDR1 binding reagent to isolate a population of cells, b) optionally culturing the cell population to facilitate proliferation and/or differentiation, and c) the use of a DNER, DISP2, SEZ6L2, LRP11 and/or SLC30A8 binding reagent to isolate a subset of the population of cells. The DNER, DISP2, SEZ6L2, LRP11 and/or SLC30A8 positive cell population isolated by this method will comprise cells selected from group consisting of endocrine pre-progenitor cells, endocrine progenitor cells, early endocrine cells, and/or fully differentiated endocrine cells.

In some aspects the invention relates to a method comprising the steps of a) the use of a DNER, DISP2, SEZ6L2, LRP11 and/or SLC30A8 binding reagent to isolate a population of cells, b) optionally culturing the cell population to facilitate proliferation and/or differentiation, c) the use of a DDR1 binding reagent to isolate a subset of the population of cells, d) optionally culturing the cell population to facilitate proliferation and/or differentiation, and e) optionally repeating steps a) to d) until the required amount of DNER, DISP2, SEZ6L2, LRP11 and/or SLC30A8 positive cells has been achieved.

In some aspects using DNER, DISP2, SEZ6L2, LRP11 and/or SLC30A8 as a marker will provide a cell population comprising endocrine pre-progenitor cells, endocrine progenitor cells, early endocrine cells, and/or fully differentiated endocrine cells with a low ratio of other cell types, such as less than 20%, less than 15%, less than 10%, less than 5%, less than 2%, or no other cell types, such as endodermal cells other than pancreatic cells and neural cells. A double sorting using DNER and DDR1 binding reagents might not be needed if the starting population is only of pancreatic or endodermal origin without neural cells.

In some aspects using DDR1 and DNER, DISP2, SEZ6L2, LRP11 and/or SLC30A8 as markers in combination either simultaneously or sequentially will provide a cell population comprising endocrine pre-progenitor cells, endocrine progenitor cells, and/or early endocrine cells with a low ratio of other cell types, such as less than 20%, less than 15%, less than 10%, less than 5%, less than 2%, or no other cell types, such as endodermal cells other than pancreatic cells and neural cells. A double sorting using DNER and DDR1 binding reagents might not be needed if the starting population is only of pancreatic or endodermal origin without neural cells.

In some aspects if the staring population is only of pancreatic origin, the invention relates to a first sorting for DDR1, whereby a cell population of DDR1 positive cells is obtained, and a second counter sorting for DNER, whereby DNER positive cells are removed from the DDR1 positive cells; this method will leave a cell population of pro-endocrine pre-progenitor cells, which expresses DDR1 but not DNER, along with some ductal/endocrine progenitor cells. A pro-endocrine pre-progenitor being defined as the immediate precursor of the endocrine pre-progenitor cell. In some aspects if the staring population is only of pancreatic origin, the invention relates to a first sorting for DDR1, whereby a cell population of DDR1 positive cells is obtained, and a second counter sorting for DNER, DISP2, SEZ6L2, LRP11 and/or SLC30A8, whereby DNER, DISP2, SEZ6L2, LRP11 and/or SLC30A8 positive cells are removed from the DDR1 positive cells; this method will leave a cell population of pro-endocrine pre-progenitor cells, which expresses DDR1 but not DNER, DISP2, SEZ6L2, LRP11 and/or SLC30A8, along with some ductal/endocrine progenitor cells. A pro-endocrine pre-progenitor being defined as the immediate precursor of the endocrine pre-progenitor cell.

In some aspects compositions comprising pancreatic endocrine cells substantially free of other cell types may be produced. In some aspects compositions comprising pancreatic endocrine pre-progenitor cells, pancreatic endocrine progenitor cells, early endocrine cells, and fully differentiated endocrine cells substantially free of other cell types may be produced. In some aspects compositions comprising pancreatic endocrine pre-progenitor cells substantially free of other cell types may be produced. In some aspects compositions comprising pancreatic endocrine progenitor cells substantially free of other cell types may be produced. In some aspects the expression "substantially free of" is for cell cultures or cell populations to be understood as a cell culture or cell population comprising less than 20% other cell types than pancreatic endocrine pre-progenitor cells, pancreatic endocrine progenitor cells, early endocrine cells, and fully differentiated endocrine cells in relation to the total number of cells. In some aspects the expression "substantially free of" is for cell cultures or cell populations to be understood as a cell culture or cell population comprising less than 20% other cell types than pancreatic endocrine pre-progenitor cells in relation to the total number of cells. In some aspects the expression "substantially free of" is for cell cultures or cell populations to be understood as a cell culture or cell population comprising less than 20% other cell types than pancreatic endocrine progenitor cells in relation to the total number of cells.

In some aspects the invention relates to a method wherein the resulting cell population consists of at least 30%, such as at least 40%, at least 50%, at least 60%, at least 70%, at least 80%, at least 90%, or at least 95% cells selected from the group consisting of endocrine pre-progenitor cells, endocrine progenitor cells, early endocrine cells, and/or fully differentiated endocrine cells. In some aspects the invention relates to a method wherein the resulting cell population consists of at least 30%, such as at least 40%, at least 50%, at least 60%, at least 70%, at least 80%, at least 90%, or at least 95% endocrine pre-progenitor cells. In some aspects the invention relates to a method wherein the resulting cell population consists of at least 30%, such as at least 40%, at least 50%, at least 60%, at least 70%, at least 80%, at least 90%, or at least 95% endocrine progenitor cells.

In some aspects the invention relates to a method wherein the starting cell population is of endodermal origin and the resulting cell population consists of at least 30%, such as at least 40%, at least 50%, at least 60%, at least 70%, at least 80%, at least 90%, or at least 95% cells selected from the group consisting of endocrine pre-progenitor cells, endocrine progenitor cells, early endocrine cells, and/or fully differentiated endocrine cells. In some aspects the invention relates to a method wherein the starting cell population is of endodermal origin and the resulting cell population consists of at least 30%, such as at least 40%, at least 50%, at least 60%, at least 70%, at least 80%, at least 90%, or at least 95% cells selected from the group consisting of endocrine pre-progenitor cells. In some aspects the invention relates to a method wherein the starting cell population is of endodermal origin and the resulting cell population consists of at least 30%, such as at least 40%, at least 50%, at least 60%, at least 70%, at least 80%, at least 90%, or at least 95% endocrine progenitor cells.

In some aspects the invention relates to a method wherein the starting cell population comprises cells of endodermal and neural origin and the resulting cell population consists of at least 30%, such as at least 40%, at least 50%, at least 60%, at least 70%, at least 80%, at least 90%, or at least 95% cells selected from the group consisting of endocrine pre-progenitor cells, endocrine progenitor cells, early endocrine cells, and/or fully differentiated endocrine cells. In some aspects the invention relates to a method wherein the starting cell population comprises cells of endodermal and neural origin and the resulting cell population consists of at least 30%, such as at least 40%, at least 50%, at least 60%, at least 70%, at least 80%, at least 90%, or at least 95% cells selected from the group consisting of endocrine pre-progenitor cells. In some aspects the invention relates to a method wherein the starting cell population comprises cells of endodermal and neural origin and the resulting cell population consists of at least 30%, such as at least 40%, at least 50%, at least 60%, at least 70%, at least 80%, at least 90%, or at least 95% cells selected from the group consisting of endocrine progenitor cells. In some aspects the invention relates to a method wherein the DNER, DISP2, SEZ6L2, LRP11 and/or SLC30A8 binding reagent simultaneously or sequentially is used in combination with one or more additional binding reagents when the starting cell population comprises cells of endodermal and neural origin wherein the starting cell population comprises cells of endodermal and neural origin. In some aspects the invention the additional binding reagent is selected from the group consisting of DDR1, prominin 1 (also known as CD133), and CD49f binding reagent. In some aspects the invention the additional binding reagent is DDR1 binding reagent.

In some aspects the invention relates to an isolated cell selected from the group consisting of endocrine pre-progenitor cells, endocrine progenitor cells, early endocrine cells and fully differentiated endocrine cells obtained by any of the methods defined herein. In some aspects the invention relates to an isolated endocrine pre-progenitor cell obtained by a method as defined in any of the methods defined herein. In some aspects the invention relates to an isolated endocrine progenitor cell obtained by a method as defined in any of the methods defined herein.

In some aspects the invention relates to a composition comprising isolated cells selected from one or more cells from the group consisting of endocrine pre-progenitor cells, endocrine progenitor cells, early endocrine cells and fully differentiated endocrine cells obtained by a method as defined in any of the methods defined herein. In some aspects the invention relates to a composition comprising isolated endocrine pre-progenitor cells obtained by a method as defined in any of the methods defined herein. In some aspects the invention relates to a composition comprising isolated endocrine progenitor cells obtained by a method as defined in any of the methods defined herein.

Cellular Differentiation Markers

In some aspects the invention relates to a method of obtaining a culture of cells comprising cells selected from the group consisting of endocrine pre-progenitor cells, endocrine progenitor cells, early endocrine cells, and/or fully differentiated endocrine cells, the method comprising: obtaining cells purified according to the method described above or herein and then subsequently culturing the obtained cells under conditions which facilitate differentiation of the pancreatic cells into cells selected from the group consisting of endocrine pre-progenitor cells, endocrine progenitor cells, early endocrine cells, and/or fully differentiated endocrine cells. In some aspects the invention relates to a method of obtaining a culture comprising endocrine pre-progenitor cells, the method comprising: obtaining cells purified according to the method described above or herein and then subsequently culturing the obtained cells under conditions which facilitate differentiation of the endocrine pre-progenitor cells. In some aspects the invention relates to a method of obtaining a culture comprising endocrine progenitor cells, the method comprising: obtaining cells purified according to the method described above or herein and then subsequently culturing the obtained cells under conditions which facilitate differentiation of the endocrine progenitor cells.

There are a number of cellular markers that can be used to identify populations of pancreatic cells. Donor cells isolated and cultured begin to display various phenotypic and genotypic indicia of differentiated pancreatic cells. Examples of the phenotypic and genotypic indicia include various molecular markers present in the facultative progenitor cell population that are modulated (e.g., either up or down regulated). These molecular markers include CK-19 or the Pdx1/Nkx6.1/Ptf1a triple positive cell, which is hypothesized to be a marker of the pancreatic facultative stem cell (i.e. the multi-potent pancreatic stem cell).

Typically, mammalian stem cells proceed through a number of developmental stages as they mature to their ultimate developmental endpoint. Developmental stages often can be determined by identifying markers present or absent in developing cells. Because human endocrine cells develop in a similar manner, various markers can be used to identify cells as they transition from a stem cell-like phenotype to pseudo-Islet phenotype.

The expression of markers in cells induced to proliferate or differentiate by the methods of the present invention bears some similarity to the sequence of marker expression in normal human pancreas development. Very early in development, the primordial epithelial cells express Pdx1, an early cellular marker that is a homeodomain nuclear factor. As the cells develop, they begin to bud out and form a duct. These cells express cytokeratin 19, a marker for epithelial ductal cells, and temporally express Ngn3 leading developmentally to endocrine cells. As these cells continue to develop towards endocrine cells, they gain the ability to express insulin, somatostatin, glucagon, ghrelin, or pancreatic polypeptide. The final differentiated cells are only able to express one and become the alpha cells (glucagon), beta cells (insulin), delta cells (somatostatin), epsilon cells (ghrelin), and PP-cells.

It is believed that the DNER, DISP2, SEZ6L2, LRP11 and/or SLC30A8 positive cell population used herein can be divided into the main categories of endocrine pre-progenitor cells, endocrine progenitor cells, early endocrine cells, and fully differentiated endocrine cells.

The extracellular expression of DNER may vary in different domains of the pancreas and changes during the stages of development of pancreatic endocrine cells, see, e.g., schematic overview in FIG. 1.

DNER is expressed in some cells of the pancreatic endoderm. DNER is not expressed in the multi-potent pancreatic progenitor cell. DNER is not expressed in the acinar lineage. DNER is not expressed in the exocrine lineage. DNER is not expressed in the ductal lineage. DNER is not expressed in the endocrine intestinal lineage. DNER appears to be expressed in a novel cell type that is at a stage of differentiation prior to expression of Ngn3 protein, i.e. the endocrine pre-progenitor cell. Thus, DNER can be used to identify, enrich, and/or isolate endocrine pre-progenitor cells. DNER may be expressed at high, medium or low levels in the endocrine progenitor cell. Thus, DNER can be used to identify, enrich, and/or isolate endocrine progenitor cells. DNER may be expressed at high, medium or low levels in the early endocrine cell. Furthermore, DNER may be expressed in hormone positive endocrine cells and in the adult pancreatic endocrine cells, such as fully differentiated endocrine cells. Thus, DNER can also be used to identify, enrich, and/or isolate fully differentiated endocrine cells. Accordingly, DNER may be used to identify, enrich, and/or isolate pancreatic cells selected from the group consisting of endocrine pre-progenitor cells, endocrine progenitor cells, early endocrine cells, and/or fully differentiated endocrine cells. Specifically, while many proteins, such as ptprn/IA2, Abcc8/Sur1, and Slc30a8/ZnT-8, can be used to identify, enrich, and/or isolate fully differentiated endocrine cells, only DNER may be used to identify, enrich, and/or isolate endocrine pre-progenitor cells.

Whether the cells are indeed examples of a precursor in the development pathway or simply a result of in vitro manipulation, the DNER, DISP2, SEZ6L2, LRP11 and/or SLC30A8 positive cells are believed to be able to eventually express endocrine hormones or to mature from pancreatic early endocrine cells to a more mature endocrine cell type and, therefore, have the potential to be used to correct a deficiency in any type of Islet cell.

Furthermore, the DDR1 positive cell population is believed to be at a less than fully differentiated stage of development, retaining the potential to differentiate into fully differentiated endocrine cells and the ability to proliferate. Whether the cells are indeed examples of a precursor in the development pathway or simply a result of in vitro manipulation, the DDR1 positive cells are believed to be able to proliferate as well as to eventually express endocrine hormones or to mature from pancreatic early endocrine cells to a more mature endocrine cell type and, therefore, have the potential for being used to correct a deficiency in any type of Islet cell.

Markers of interest are molecules that are expressed in temporal- and tissue-specific patterns in the pancreas (see Hollingsworth, Ann N YAcad Sci 880: 38-49 (1999)). These molecular markers are divided into three general categories: transcription factors, notch pathway markers, and intermediate filament markers. Examples of transcription factor markers include Pdx1, NeuroD, Nkx6.1, Isl1, Pax6, Pax4, Ngn3, and HES1.

Examples of notch pathway markers include Notch1, Notch2, Notch3, Notch4, Jagged1, Jagged2, Dll1, and RBPjk. Examples of intermediate filament markers include CK19 and nestin. Examples of markers of precursors of pancreatic beta cells include Pdx1, Pax4, Ngn3, and Hb9. Examples of markers of fully differentiated pancreatic beta cells include insulin, ptprn/IA2, Abcc8/Sur1, and Slc30a8/ZnT-8.

Insulin mRNA Expression

In some aspects the level of insulin mRNA may be used to characterize pancreatic cell identity, differentiation, or maturity. For example, the intermediate cell population of the present invention show expression of insulin mRNA within a defined range. Method for quantifying insulin mRNA include Northern blots, nuclease protection, and primer extension.

In some aspects RNA is extracted from a population of cultured cells, and the amount of proinsulin message is measured by quantitative reverse transcription PCR. Following reverse transcription, insulin cDNA is specifically and quantitatively amplified from the sample using primers hybridizing to the insulin cDNA sequence, and amplification conditions under which the amount of amplified product is related to the amount of mRNA present in the sample (see, e.g., Zhou et al. (1997), J Biol Chem 272: 25648-51). In some aspects kinetic quantification procedures are preferred due to the accuracy with which starting mRNA levels can be determined.

Frequently, the amount of insulin mRNA is normalized to a constitutively expressed mRNA such as actin, which is specifically amplified from the same RNA sample using actin-specific primers. Thus, the level of expression of insulin mRNA may be reported as the ratio of insulin mRNA amplification products to actin mRNA amplification products, or simply the insulin: actin mRNA ratio. The expression of mRNAs encoding other pancreatic hormones (e.g., somatostatin or glucagon) may be quantified by the same method. Insulin and actin mRNA levels can also be determined by in situ hybridization and then used to determine insulin: actin mRNA ratios. In situ hybridization methods are known to those skilled in the art.

Methods of Expansion

In some aspects the invention relates to a method of expanding the number of cells comprising cells selected from the group consisting of endocrine pre-progenitor cells, endocrine progenitor cells, early endocrine cells, and/or fully differentiated endocrine cells, the method comprising: obtaining cells purified according to the method described above or herein and then subsequently culturing the obtained cells under conditions which facilitate expansion of the cell type(s) obtained. In some aspects the invention relates to a method of expanding the number of endocrine pre-progenitor cells, the method comprising: obtaining cells purified according to the method described above or herein and then subsequently culturing the obtained cells under conditions which facilitate expansion of the endocrine pre-progenitor cells. In some aspects the invention relates to a method of expanding the number of endocrine progenitor cells, the method comprising: obtaining cells purified according to the method described above or herein and then subsequently culturing the obtained cells under conditions which facilitate expansion of endocrine progenitor cells.

In some aspects the invention relates to a method of expanding the number of cells comprising cells selected from the group consisting of endocrine pre-progenitor cells, endocrine progenitor cells, early endocrine cells, and/or fully differentiated endocrine cells, the method comprising: obtaining cells purified and expanded according to the method described above or herein and then subsequently culturing the obtained cells under conditions which facilitates differentiation of the pancreatic cells into cells selected from the group consisting of endocrine pre-progenitor cells, endocrine progenitor cells, early endocrine cells, and/or fully differentiated endocrine cells. In some aspects the invention relates to a method of expanding the number of endocrine pre-progenitor cells, the method comprising: obtaining cells purified and expanded according to the method described above or herein and then subsequently culturing the obtained cells under conditions which facilitates differentiation of the endocrine pre-progenitor cells. In some aspects the invention relates to a method of expanding the number of endocrine progenitor cells, the method comprising: obtaining cells purified and expanded according to the method described above or herein and then subsequently culturing the obtained cells under conditions which facilitates differentiation of the endocrine progenitor cells.

A protocol for expansion of pancreatic cells derived from fetal/adult tissue and stem cells is exemplified by, but not limited to, the protocols described in Heimberg, H. et al. (2000), Diabetes 49, 571-9; Heremans, Y. et al. (2002), J Cell Biol 159, 303-12; Miralles, F. et al. (1998), Development 125, 1017-24; and Miralles, F. et al. (1999), Dev Dyn 214, 116-26.

Functional Assays

One of the important functions of a beta cell is to adjust its insulin secretion according to the glucose level. Typically, a static glucose stimulation (SGS) assay can be performed on the proliferating adherent pancreatic cells to identify whether they are able to secrete insulin in response to different glucose levels. Cells are generally cultured on an appropriate substrate until nearly confluent. Three days prior to the SGS test, the culture medium is replaced by a medium of similar character but lacking insulin and containing only 1 g/L of glucose. The medium is changed each day for three days and the SGS test is performed on day four.

Before the test, the culture medium may be collected for glucose and insulin analysis. To prepare cells for the test, cells are washed twice with Dulbecco's phosphate-buffered saline (DPBS)+0.5% BSA, incubating for 5 minutes with each wash, and then once with DPBS alone, also incubating for 5 minutes. After washing, the cells are incubated with 10 ml (in a 100 mm dish) or 5 ml (in a 60 mm dish) of Krebs-Ringers SGS solution with 60 mg/dl glucose (KRB-60) for 30 minutes in a 37° C. incubator. This incubation is then repeated.

To perform the SGS assays, cells are incubated in 3 ml (100 mm dish) or 4 ml (T75 flask) or 2 ml (60 mm dish) KRB-60, at 37° C. for 20 minutes. The medium is aspirated and spun, and is collected for insulin assay as LG-1 (low glucose stimulated step). KRB-450+theo (KRB with 450 mg/dl glucose and 10 mM theophylline) is then added with the same volume as above or herein, and cells are cultured under the same condition as above or herein. The supernatant is collected for insulin assay as HG (high glucose stimulated). The cells are then incubated again with KRB-60 and the medium collected as LG-2, and another time as LG-3. The media are collected for insulin analysis, and stored at −20° C. until insulin content is determined by radioimmunoassay (RIA) or other suitable assay.

The results of the SGS test are often expressed as a stimulation index, defined as the HG insulin value divided by the LG-1 insulin value. Generally, a stimulation index of about 2 or greater is considered to be a positive result in the SGS assay, although other values (e.g., 1.5, 2.5, 3.0, 3.5, etc.) may be used to define particular cell populations.

Treatment Methods

In some aspects the invention relates to a method of providing pancreatic endocrine function to a mammal deficient in its production of at least one pancreatic hormone wherein cells are obtained by any of the methods described above or herein, the method further comprising the steps of: implanting into the mammal the obtained cells in an amount sufficient to produce a measurable amount of at least one pancreatic hormone in the mammal.

Those skilled in the art will recognize that DNER, DISP2, SEZ6L2, LRP11 and/or SLC30A8 selected cells or further cultured and differentiated cells provide a renewable resource for implantation and restoration of pancreatic function in a mammal.

DNER, DISP2, SEZ6L2, LRP11 and/or SLC30A8 positive pancreatic cells are first differentiated before implantation into the mammal. Alternatively, DNER, DISP2, SEZ6L2, LRP11 and/or SLC30A8 selected cells are implanted in the progenitor state and allowed to differentiate in the body. If desired by the user, DNER, DISP2, SEZ6L2, LRP11 and/or SLC30A8 cells can be encapsulated before implantation.

Differentiation of DNER, DISP2, SEZ6L2, LRP11 and/or SLC30A8 positive pancreatic cells before implantation into the mammal may be to the stages of differentiation selected from the group consisting of fully differentiated endocrine cells, including glucose responsive insulin producing beta cells, i.e. equivalent to beta cells of the isolated Islet of Langerhans. An example of implantation isolated Islet of Langerhans using the so-called Edmonton protocol can be found in Shapiro A M (2000), N Engl J Med.; 343(4):230-8.

Cells selected by DNER, DISP2, SEZ6L2, LRP11 and/or SLC30A8 may be implanted in the progenitor state, i.e. immature cells, such as a cell population comprising cells selected from the group consisting of pancreatic pre-progenitor cells, pancreatic progenitor cells, and/or early endocrine cells, and allowed to differentiate in the body. In some aspects cells selected by DNER, DISP2, SEZ6L2, LRP11 and/or SLC30A8 may be implanted in the progenitor state of pancreatic pre-progenitor cells. In some aspects cells selected by DNER, DISP2, SEZ6L2, LRP11 and/or SLC30A8 may be implanted in the progenitor state of pancreatic progenitor cells. Accordingly, the DNER, DISP2, SEZ6L2, LRP11 and/or SLC30A8 positive cells may be used directly for transplantation. In this situation, the in vivo environment is anticipated to cause the DNER, DISP2, SEZ6L2, LRP11 and/or SLC30A8 postive cells to differentiate into therapeutic beta cells. An example of the use of immature pancreatic cells for transplantation is described in Kroon E et al. (2008), Nat Biotechnol 26, 443-452.

Encapsulation of the DNER, DISP2, SEZ6L2, LRP11 and/or SLC30A8 positive cells results in the formation of cellular aggregates in the capsules. Encapsulation can allow the pancreatic cells to be transplanted into a type 1 diabetic host, while minimizing the immune response of the host animal. The porosity of the encapsulation membrane can be selected to allow secretion of biomaterials, like insulin, from the capsule, while limiting access of the host's immune system to the foreign cells.

Encapsulation methods are known in the art and are disclosed in the following references: van Schelfgaarde & de Vos, J. Mol. Med. 77: 199-205 (1999), Uludag et al. Adv. Drug Del Rev. 42: 29-64 (2000) and U.S. Pat. Nos. 5,762,959, 5,550,178, and 5,578,314.

Encapsulation methods are described in detail in application PCT/US02/41616; herein incorporated by reference.

Implantation or transplantation into a mammal and subsequent monitoring of endocrine function may be carried out according to methods commonly employed for Islet transplantation; see, e.g., Ryan et al., Diabetes 50: 710-19 (2001); Peck et al., Ann Med 33: 186-92 (2001); Shapiro et al., N Engl J Med 343 (4): 230-8 (2000); Carlsson et al., Ups J Med Sci 105 (2): 107-23 (2000) and Kuhtreiber, W M, Cell Encapsulation Technology and Therapeutics, Birkhauser, Boston, 1999. In some aspects preferred sites of implantation include the peritoneal cavity, the liver, and the kidney capsule.

A person skilled in the art will realise that in the case of carrying out transplantation using pancreatic cells comprising immature pancreatic cells, measurement of beta cell function, such as measurement of pancreatic hormone and blood glucose levels, should be carried out at least 2 weeks, such as at least 4 weeks, at least 6 weeks, or at least 8 weeks after the transplantation. In contrast, when carrying out transplantation using differentiated pancreatic cells beta cell function, such as measurement of pancreatic hormone and blood glucose levels, should be carried out right after transplantation, such as before 12 hours, before 24 hours, or before 36 hours after the transplantation.

A person skilled in the art will be able to determine an appropriate dosage of the number of fully differentiated beta cells or microcapsules for an intended recipient. The dosage will depend on the insulin requirements of the recipient. Insulin levels secreted by the defined number of beta cells or microcapsules can be determined immunologically or by amount of biological activity. The recipient's body weight can also be taken into account when determining the dosage. If necessary, more than one implantation can be performed as the recipient's response to the (optionally encapsulated) cells is monitored. Thus, the response to implantation can be used as a guide for the dosage of (optionally encapsulated) cells. (Ryan et al. (2001), Diabetes 50: 710-19).

The function of (optionally encapsulated) cells in a recipient can be determined by monitoring the response of the recipient to glucose. Implantation of the (optionally encapsulated) cells can result in control of blood glucose levels. In addition, evidence of increased levels of pancreatic endocrine hormones, insulin, C-peptide, glucagon, and somatostatin can indicate function of the transplanted (optionally encapsulated) cells.

One skilled in the art will recognize that control of blood glucose can be monitored in different ways. For example, blood glucose can be measured directly, as can body weight and insulin requirements. Oral glucose tolerance tests can also be given. Renal function can also be determined as can other metabolic parameters. (Soon-Shiong, P. et al. (1993), PNAS USA 90: 5843-5847; Soon-Shiong, P. et al. (1994), Lancet 343: 950-951).

The term "insulin producing endocrine pancreatic cells" as used herein refers to cells that produce insulin and secrete insulin in a blood glucose dependent manner.

In some aspects the cell population comprising pancreatic cells are isolated (this invention) from a cultured source. The isolated cells are then used for example in further culturing or for microencapsultation according to the microencapsulation method of U.S. Pat. No. 5,762,959.

The term "providing pancreatic function to a mammal in need of such function" refers to a method of producing pancreatic hormones within the body of a mammal unable to produce such hormones on its own. In some aspects the pancreatic hormone is selected from the group consisting of insulin, glucagon, somatostatin, pancreatic polypeptide, and ghrelin. In some aspects insulin is produced in the body of a diabetic mammal. The pancreatic function is provided by implanting or transplanting insulin producing pancreatic cells, produced by the methods of this disclosure into the mammal. The number of aggregates implanted is an amount sufficient to produce a measurable amount of insulin in the mammal. The insulin can be measured by Elisa assay or Radioimmunoassay or by other detection methods known to those skilled in the art, including assays for insulin function, such as maintenance of blood glucose levels.

Insulin is co-secreted with C-peptide in equimolar amounts. Thus, insulin secretion activity can also be measured by detecting C-peptide in the blood. In some aspects the provision of pancreatic function is sufficient to decrease or eliminate the dependence of the mammal on insulin produced outside the body.

"Encapsulation" refers to a process where cells are surrounded by a biocompatible acellular material, such as sodium alginate and polylysine. Preferably small molecules, like sugars and low molecular weight proteins, can be taken up from or secreted into an environment surrounding the encapsulated cells. At the same time access to the encapsulated cells by larger molecules and immune cells is limited.

"Implanting" is the grafting or placement of the cells into a recipient. It includes encapsulated cells and non-encapsulated. The cells can be placed subcutaneously, intramuscularly, intraportally or interperitoneally by methods known in the art.

In some aspects the step of separating is done by fluorescence activated cell sorting. In some aspects the step of separating is done by panning. In some aspects the step of separating is done by fluidised bed.

In some aspects the invention also relates to the use of a binding reagent selected from the group consisting of DNER, DISP2, SEZ6L2, LRP11 and SLC30A8 binding reagent to identify or select cells that express DNER, DISP2, SEZ6L2, LRP11 and/or SLC30A8 protein as a cell surface marker. In some aspects the invention relates to the simultaneous or sequential use of a binding reagent selected from the group consisting of DNER, DISP2, SEZ6L2, LRP11 and SLC30A8 binding reagent to identify or select cells that express DNER, DISP2, SEZ6L2, LRP11 and/or SLC30A8 protein as a cell surface marker in combination with one or more additional binding reagents, which are subjected to the same step(s) of analysis as the binding reagent selected from the group consisting of DNER, DISP2, SEZ6L2, LRP11 and SLC30A8 binding reagent. In some aspects the additional binding reagent is selected from the group consisting of DDR1, prominin 1 (also known as CD133), and CD49f binding reagent. In some aspects the additional binding reagent is DDR1 binding reagent.

The invention also relates to the use of DNER, DISP2, SEZ6L2, LRP11 and/or SLC30A8 protein as a cell surface marker to obtain a culture of pancreatic endocrine progenitor cells or pancreatic hormone secreting cell or early endocrine cells. In some aspects the invention relates to the simultaneous or sequential use of DNER, DISP2, SEZ6L2, LRP11 and/or SLC30A8 protein as a cell surface marker to obtain a culture of pancreatic endocrine progenitor cells or pancreatic hormone secreting cell or early endocrine cells in combination with one or more additional binding reagents. In some aspects the additional binding reagent may be subjected to the same step(s) of analysis as the binding reagent selected from the group consisting of DNER, DISP2, SEZ6L2, LRP11 and SLC30A8 binding reagent. In some aspects the additional binding reagent is selected from the group consisting of DDR1, prominin 1 (also known as CD133), and CD49f binding reagent. In some aspects the additional binding reagent is DDR1 binding reagent. In some aspects the additional binding reagents are selected from the group consisting of Ptprn/IA2, Abcc8/Sur1, and Slc30a8/ZnT-8 binding reagent, which can be used to isolate early and fully differentiated endocrine cells.

In some aspects the invention also relates to the method of treating type I diabetes by providing pancreatic function to a mammal in need of such function.

In Vitro Protocol Optimisation

In some aspects an in vitro culture comprising pancreatic cells is periodically moni-tored for expression of DNER, DISP2, SEZ6L2, LRP11 and/or SLC30A8. In some aspects one or more additional markers may be used in combination with DNER, DISP2, SEZ6L2, LRP11 and/or SLC30A8 either simultaneously or sequentially. In some aspects the additional marker is selected from the group consisting of DDR1 protein, prominin 1 (also known as CD133), and CD49f. In some aspects the additional marker is DDR1 protein. High expression levels of DNER mark cells that are committed to become endocrine cells but that are at a stage of development prior to expression of Ngn3 protein.

For efficient optimization of differentiation of embryonic stem cells it is very important to have markers identifying the various stages of development of pancreatic cells towards fully differentiated endocrine cells. DNER and DDR1 may alone or in combination be used to pinpoint important and specific stages of cellular differentiation which until now not have been possible to detect using other markers. DNER and/or DDR1 may be used in combination with one or more additional markers. DNER, DISP2, SEZ6L2, LRP11, SLC30A8 and DDR1 may alone or in combination be used to pinpoint important and specific stages of cellular differentiation which until now not have been possible to detect using other markers. DNER, DISP2, SEZ6L2, LRP11, SLC30A8 and/or DDR1 may be used in combination with one or more additional markers.

Cells expressing DNER, DISP2, SEZ6L2, LRP11 and/or SLC30A8 can be identified, enriched, and/or isolated using methods as described above or herein, e.g., FACS.

In some aspects sequential isolation of DDR1+ and DNER+ cells provide the substantial advantage of generating pure cultures of endocrine pre-progenitor cells, e.g., from ES cell derived definitive endodermal cell population. In some aspects sequential isolation of DDR1 positive cells and DNER, DISP2, SEZ6L2, LRP11 and/or SLC30A8 positive cells provide the substantial advantage of generating pure cultures of endocrine pre-progenitor cells, e.g., from ES cell derived definitive endodermal cell population. Hereby cultures are obtained that can be subjected to further expansion and/or differentiated towards more pure endocrine cell populations.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law).

All headings and sub-headings are used herein for convenience only and should not be construed as limiting the invention in any way.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

EXAMPLES

The animal origin and concentration of the antibodies used in the examples herein are shown in Table 1. All secondary antibodies were diluted and used according to the manufacturer's instructions.

TABLE 1

Origin and concentration of antibodies

| Antibody raised against[1] | Antibody raised in | | | |
|---|---|---|---|---|
| | Goat | Mouse | Rabbit | Guinea pig |
| mPtf1a | | | N.A. (serum) | |
| hDNER | 0.2 mg/ml IgG | | | |
| mDner | 0.2 mg/ml IgG | | | |
| hDdr1 | 0.2 mg/ml IgG | | | |
| hHuC/D | | from 0.2-0.1 mg/ml IgG | | |
| mNgn3 | | 1.07 mg/ml IgG | N.A. (serum) | |
| mPax6 | | | N.A. (serum) | |
| mPdx1 | N.A. (serum) | 0.994 mg/ml IgG | N.A. (serum) | N.A. (serum) |

[1]Prefix m or h indicates whether the antibody as raised against a protein of mouse or human origin, respectively, i.e. mX indicates an antibody raised against mouse protein X and hX indicates an antibody raised against human protein X.
N.A. Information on concentration was not available Example 1

Bioinformatic Analysis of Mouse and Human Dner

In order to find the extracellular and transmembrane domains mouse and human Dner were passed through the transmembrane predictor TMHMM Server v. 2.0 at CBS (http://www.cbs.dtu.dk/). The results showed that both human and mouse Dner were predicted to be a single transmembrane protein (type I) with the main first 638 amino acids on the extracellular side in both human and mouse, and the transmembrane domain predicted to be amino acids 639-661. The transmembrane-like area predicted by TMHMM in the first part of the Dner protein is the signal peptide, which is also discussed in the results below relating to SignalP.

Mouse and human signal peptide of Dner were analyzed using the SignalP 3.0 predicting Server at CBS (http://www.cbs.dtu.dk/). Mouse: Signal peptide probability: 1.000; Signal anchor probability: 0.000; Max cleavage site probability: 0.494 between positions 39 and 40. Human: Signal peptide probability: 1.000; Signal anchor probability: 0.000; Max cleavage site probability: 0.379 between positions 34 and 35. The results showed that the transmembrane like structure observed in mouse and human Dner is not a transmembrane domain but the signal peptide with a probability of 1.

To investigate the amino acid differences between mouse and human Dner the amino acid sequence of the proteins were aligned by the use of Clustal W (at http://www.ebi.ac.uk/Tools/clustalw/). The results are shown in FIG. 2. Alignment identity was 90%. Thus, the amino acid sequence of Dner in mouse and human is highly conserved. The transmembrane domain is underlined: Amino acids 639-661.

Mouse and human Dner were then passed through post-translational prediction servers at CBS (at http://www.cbs.dtu.dk/) to obtain information about modifications that could also be bound by Dner binding reagents. The results are shown in FIGS. 3-6. To investigate GlcNAc O-glycosylation mouse and human Dner were passed through the DictyOGlyc 1.1 Server (at http://www.cbs.dtu.dk/). FIG. 3 shows that GlcNAc O-glycosylation was predicted to be present on the extracellular side of mouse and human Dner and is indicated with a "G". To investigate Glycation of epsilon amino groups of lysines mouse and human Dner were passed through the NetGlycate 1.0 Server (at http://www.cbs.dtu.dk/). FIG. 4 shows that glycation is predicted to be present on the extracellular side of mouse and human Dner and is indicated with a "G". To investigate N-glycosylation on asparagines mouse and human Dner were passed through the NetGlycate 1.0 Server (at http://www.cbs.dtu.dk/). FIG. 5 shows that N-glycosylation is predicted to be present on the extracellular side of mouse and human Dner and is indicated with an "N". To investigate Mucin type GalNAc O-glycosylation mouse and human Dner were passed through the NetOGlyc 3.1 Server (at http://www.cbs.dtu.dk/). FIG. 6 shows that glycosylations were predicted to be present on the extracellular side of mouse and human Dner and is indicated with a "T". Underlining, i.e. "_____", indicate the signal peptide that is cleaved off.

These results (TMHMM, SignalP and FIGS. 2-6) showed that Dner is very likely to be post-translationally modified on the extracellular side. Both the mouse and human form of Dner can thus be bound by binding reagents that recognizes such modifications.

Bioinformatic analysis of mouse and human DDR1 can be performed according to Example 1 of PCT/EP2008/068061 and results hereof are shown therein. Investigation of isotypes of mouse DDR1 can be performed according to Example 2 of PCT/EP2008/068061 and results hereof are shown therein.

Example 2

Expression of Dner and Ddr1 in Pancreatic Beta Cell Lines

Total RNA was isolated from the mouse endocrine-like cells lines: Ins1, BetaHC, BetaTCtet (condition: cultured with tetracycline (+tet)), BetaTCtet (condition: cultured without tetracycline (−tet)), Min6 and AlphaTC and from e15.5 NMRI gut (stomach, duodenum, spleen, and pancreas) tissue. The cell line Ins1 is described in M Asfari et al. Endocrinology, Vol 130, 167-178. The cell line BetaHC-9 is described in Noda M et al., Diabetes, 1996 December;

45(12):1766-73. The cell line BetaTC-tet is described in Fleischer N et al., Diabetes, 1998 September; 47(9):1419-25. The cell line Min6 is described in J Miyazaki et al., Endocrinology, 1990 July; 127(1):126-32. The cell line AlphaTC is described in Powers AC et al., Diabetes, 1990 April; 39(4): 406-14. Using the RNA as template random primed cDNA was made. 35 cycles of PCR was performed on these cDNAs (96° C. for 180 seconds, then (96° C. for 30 seconds, 55° C. for 30 seconds, 72° C. for 30 seconds)x35 times). e15.5 cDNA was used as positive control and water $H_2O$ was used as negative control.

The results showed that Ddr1 was expressed in all cell lines investigated and that Dner is expressed in all cell lines except Ins1. This demonstrates that it is possible to obtain Dner and Ddr1 expression in cultures of cells. It is expected that similar results could be obtained for ES cells differentiated to pancreatic cells.

Example 3

Expression of Dner and Ddr1 in the Endocrine-Like Cell Line, alphaTC, Visualized by IHC in Chamber Slides AlphaTC were grown in DMEM with 1000 mg/L D-Glucose, sodium pyruvate (0.5 mM), P/S (Penicillin (10 IU/ml), streptomycin (10 µg/ml)), and 10% FCS. The cell line AlphaTC is described in Powers AC et al., Diabetes, 1990 April; 39(4):406-14. Cells were fixed in Lilliys fixative for 45 minutes and then washed in PBS and stored at +5° C. in PBS until use. Staining was done by permeabilizing cells in an ethanol gradient (starting with 70% moving to 96%, then to 99%, then again 99%, then to 96%, and finally to 70%, using 5 minutes incubation with each concentration) and subsequently blocking with 0.5% TNB blocking reagent (from Perkin-Elmer). Goat anti-Dner (R&D Systems, AF2254, 1:150) or mouse anti-Ddr1 (R&D Systems, MAB2396, 1:50) was then added and incubated overnight (O/N) at room temperature (RT). The following day cells were washed in PBS and biotinylated anti-donkey or anti-mouse antibody was added and incubated for 45 minutes. After washing the cells in PBS streptavidin-HRP was added and incubated for 15 minutes and subsequently washed in PBS. Finally tyramid-cy3 was added to develop the staining.

The results showed that heterogeneous Dner and Ddr1 immunoreactivity could be detected in alphaTC. A strong and distinct immunoreactivity was observed for Dner in about 10% of the cells. A clear immunoreactiviy was also observed for Ddr1 in about 10% of the cells.

When differentiating ES cells into beta cells it is expected that other cells types will also be produced. Dner and/or Ddr1 can then be used to isolate the wanted subset of cells. This is illustrated in the heterogeneous Dner and Ddr1 staining in Examples 4-7 herein. ES cells are differentiated to endodermal cells by activin A and then to pancreatic cells. Once the pancreatic fate has been acquired the wanted cells can be isolated. 1) To isolate the ductal/endocrine progenitor Ddr1 binding reagent can be used. 2) To isolate the endocrine pre-progenitor cells and endocrine progenitor cells Dner binding reagent can be used alone or in combination with Ddr1 binding reagent.

It is expected that cells isolated using Dner as a marker can be used to generate endocrine cell types whereas cells isolated using Ddr1 as a marker could give rise to both endocrine and ductal cell type(s). Ddr1+ cells are thus expected to comprise a subpopulation of cells that exhibit the potential of expressing DNER.

In some aspects investigation of the expression pattern of Ddr1 in mouse can be performed according to Example 3 of PCT/EP2008/068061 and results hereof are shown therein.

Example 4

Localization of Dner in the Mouse Pancreas at e15.5, e18.5 and Adult Visualized by Fluorescent Staining Mouse e15.5, e18.5 embryos, and adult tissue were harvested and fixed over night (O/N) in 4% paraformaldehyde (PFA) in PBS. Tissue was equilibrated in 30% sucrose in PBS and embedded in TissueTech. 8 µm sections were cut and stored at −80° C. Sections were thawed at room temperature (RT), washed in PBS, microwaved in 0.01 M citrate buffer and incubated with 1% $H_2O_2$ in PBS for 30 minutes and subsequently blocked with 0.5% TNB blocking reagent (from Perkin-Elmer). Goat anti-Dner 1:75, guinea pig anti-insulin (Gp antiIns) 1:200, and mouse anti-glucagon (mouse anti-Glu001) 1:75 were then added and incubated O/N at RT. The following day cells were washed in PBS and biotinylated anti-donkey, anti-mouse-cy5, and anti-gp-cy2 antibody were added and incubated for 45 minutes. After washing the cells in PBS streptavidin-HRP was added and incubated for 15 minutes. Subsequently, the cells were washed in PBS. Finally, tyramid-cy3 was added to develop the staining.

The results showed that Dner is expressed strongly in the pancreas at e15.5 and e18.5. However, in the adult pancreas heterogeneous and weaker Dner is detected. At e15.5 strong Dner immunoreactivity is detected in scattered cell with in the central Nkx6.1 positive domain of the pancreas. The localization of Dner in the pancreas was strikingly similar to the localisation of Ngn3 protein. Dner signal was only occasionally observed in insulin or glucagon positive cells. At e18.5 a Dner population that neither co-express insulin nor glucagons was still present, but the amount of insulin and glucagon positive cells that co-express Dner had dramatically increased. Furthermore, insulin and glucagon positive cells that were Dner negative were also observed. From time to time Dner was found to the co-expressed with glucagon or insulin positive cells that are in close connection to the duct system. Dner expression was also observed in the surrounding mesenchyme. Dner signal in the mesenchyme was likely to come from innervating neural cells as they are positive for HuC/D. At e18.5 Dner appeared to be less intense compared to e15.5. In the adult pancreas Dner immunoreactivity was found in the Islet. It co-localized with both insulin and glucagons. In the adult pancreas Dner also appeared to be less intense compared to e15.5 and e18.5. However, some cells expressed Dner at high levels. In summary, Dner immunoreactivity is most highly expressed in a cell type localized to the central domain of the pancreas at day e15.5 of mouse pancreas development—and with a highly characteristic "Ngn3-like" staining pattern (now known to comprise cells that are endocrine pre-progenitors and endocrine progenitors (Ngn3+ cells). Dner may be expressed to lower levels in later stage endocrine cells and in fully differentiated endocrine cells. Dner is expressed in neurons (that both innervate the pancreas and the pancreatic mesenchyme).

Example 5

Localisation of Dner, Pdx1, and Huc/HuD in the e15.5 wt and Ngn3 Null Mutant Mouse Pancreas Visualized by Fluorescent Staining To test the assumption that initiation of expression of Dner appears prior to the expression of Ngn3 protein, wild-type and Ngn3-null mutant e15.5 mouse pancreas was stained for Dner, Pdx1, and the neural marker HuC/HuD. The data clearly demonstrates that Dner is expressed in mice deficient of ngn3-expression. Dner is thus a marker expressed prior to Ngn3.

See Example 4 herein for a description of methods. Specifically, mouse anti-HuC/HuD (Molecular Probes, A-21271) was used at 1:150 and developed with donkey anti-mouse-cy2. Rabbit anti-Pdx1 (Hm-253) was used 1:600 and developed with donkey anti-rabbit-cy5.

The results showed that in the e15.5 wt pancreas by far most of the Dner positive cells co-expressed Pdx1, but not the Pdx1$^{high}$. Some of the Dner immunoreactivity that did not co-localize with Pdx1, co-localized with the neural marker HuC/HuD in the pancreas. The co-localization of Dner and HuC/HuD was nerves innervating the pancreas. HuC/HuD staining was strong. Strong Dner staining was also observed in the pancreas. A few Dner positive cells did neither co-express Pdx1 nor HuC/HuD. In the e15.5 Ngn3 null mutant pancreas a lot of Dner immunoreactivity was observed in long strings (arrowheads). Such Dner positive cells were negative for HuC/HuD and Pdx1. Only very few Dner positive cells were found to co-express Pdx1. The Dner positive cells that did co-express Pdx1 appeared to be delaminating from the Pdx1 positive endoderm. And the string of Dner+/Pdx1-cells observed in C'-C"" might be representing such delaminated cells (arrow heads). This would imply that once a cell turns on Dner, Ngn3 is needed to maintain Pdx1.

Example 6

Localization of Dner, Pax6, Pdx1, Ngn3, and Ptf1a in the Mouse e15.5 Pancreas Visualized by Fluorescent Stainings For preparation of sections, see Example 4 herein. Goat anti-Dner was used at 1:75 on sections (developed with TSA-cy3) and at 1:250 in whole mount (developed with donkey anti-goat-cy2). Rabbit anti-Pax6 (Covance, PRB-278P) was used at 1:200 on sections (developed with donkey anti-rabbit-cy5) and at 1:2000 in whole mount (developed with TSA-cy3). Rabbit anti-Pdx1 (Hm-253) was used at 1:500 on sections (developed with donkey anti-rabbit-cy5). Guinea pig anti-Pdx1 was used at 1:1000 in whole mount (Abcam, ab47308-100, developed with donkey anti-rabbit-cy5). Mouse anti-Ngn3 (AbCore, F25A1B3) was used at 1:100 on sections (developed with donkey anti-rabbit-cy2). Rabbit anti-Ngn3 (AbCore, 2369 B) was used at 1:16000 in whole mount (developed with TSA-cy3). Rabbit anti-Ptf1 a was used at 1:5000 in whole mount (developed with donkey anti-rabbit-cy5). For whole mount method see Ahnfelt-Rønne J et al., J Histochem Cytochem. 2007 September; 55(9):925-30.

The whole mount results showed that Dner is localized to the central endocrine Pax6 domain. However, on sections it was observed that Dner positive cells were mainly negative for Pax6 but was expressed very close to the Pax6 expressing cells. Some Dner positive cells did co-express Pax6. From further whole mount studies it was evident that Dner was localized in the central domain of the pancreas where Pdx1$^{high}$ expressing cells were localized. On sections it was observed that Dner is mainly negative for Pdx1$^{high}$ cell nuclei, but that close to all Dner expressing cells expressed Pdx1. Whole mount Dner staining with Ngn3 showed that Dner was localized to the central domain of the pancreas that among other cell types contains endocrine progenitors expressing Ngn3. On sections it was observed that some Dner positive cells co-expressed Ngn3, whereas other Dner positive cell were negative for Ngn3. Finally it was observed that Dner was not co-expressed with Ptf1a, which marks the acinar cells at this stage. From these results it was seen that at e15.5 Dner was expressed in the pancreatic endoderm (Dner co-localizes with Pdx1) and that Dner was mainly expressed in the pancreatic endoderm. Dner was co-expressed with Ngn3, but also before Ngn3 had turned on in a cell (note that the majority of the Dner positive cells did not co-localize with Pax6 and that Pdx1 positive Dner cells were found in the Ngn3 null mutant pancreas (Example 5 herein). Thus, Dner appears to be expressed in a novel cell type that is at a development stage prior to Ngn3, the endocrine pre-progenitor cell. It was also seen that Dner is not part of the acinar lineage as Dner did not co-localize with Ptf1a. Thus, Dner can be used to purify endocrine pre-progenitor cells. Furthermore, Dner was also expressed in some of the endocrine progenitor cells, early endocrine cells and many of the fully differentiated endocrine cells (Example 4 herein) and can thus also be used to purify such cells.

Example 7

Localization of Dner and Ddr1 in the e15.5 Mouse Visualized by Fluorescent Staining Fluorescent stainings were carried out to determine localization of Dner and Ddr1 in the e15.5 mouse pancreas and other endodermal cell types. See Example 4 herein for a description of methods. Goat anti-Ddr1 (R&D systems, AF2396) was used at 1:150, goat anti-Dner was used at 1:75, both were developed with TSA-cy3.

An experiment was conducted to determine localization of Dner and Ddr1 in the e15.5 mouse embryo visualized by fluorescent staining, on adjacent sections. The results showed that Ddr1 was highly and broadly expressed (like Nkx6.1) in the central domain of the pancreas that among other cell types contains endocrine progenitors is at this time point but not in the adjacent endoderm—duodenum or posterior stomach. Further away from the pancreas Ddr1 is expressed in the anterior stomach, esophagus and some parts of the lung. In the neural tube some expression was seen in the central part. Ddr1 was generally not expressed in the neural tissue apart from some expression in the cental part of the neural tube. Dner was also expressed in the endoderm of the pancreas. But apart from this it was not expressed in the endoderm as seen in the posterior and anterior stomach, duodenum, esophagus and lung. But Dner was strongly expressed in the non-central parts of the neural tube. Furthermore Dner was widely expressed in neurons in the body. Dner was observed in neurons surrounding the stomach, duodenum and esophagus. In the neural tube Ddr1 and Dner appeared to be expressed in complementary patterns. By comparing Ddr1 and Dner expression in the endoderm it was evident that Dner is only expressed in the pancreas whereas Ddr1 is expressed more widely. In the pancreas Ddr1 was also express more widely than Dner, as Dner was only expressed in a subset of the Ddr1 positive cells. The results also showed that Phox2b, which is expressed in all differentiated neurons except for the cranial motoneurons in the oculomotor nucleus and trochlear nucleus, was co-expressed with Dner.

Results further showed that both Dner and Ddr1 double positive cells and Dner or Ddr1 double positive cells were found in the e15.5 pancreas as visualized by fluorescent staining.

Results further showed that the Dner or Ddr1 positive cells did not co-express ghrelin in the e15.5 pancreas as visualized by fluorescent staining.

Results further showed that approx. 90% of the Ngn3 positive cells co-expressed Ddr1 in the e15.5 pancreas as visualized by fluorescent staining.

Results further showed that none of the Dner positive cells and approx. 5-10% of the Ddr1 positive cells in the e15.5 pancreas proliferated as they were positive for Ki-67, which is a marker of cellular proliferation, as visualized by fluorescent staining.

Results further showed that at e15.5 Dner was expressed in a few cells and Ddr1 was expressed in nearly all cells of the major pancreatic duct close to the junction of the duct to the duodenum. Notably both Dner and Ddr1 were only expressed in the pancreas and a sharp boundary of Dner positive cells or Ddr1 positive cells in the major pancreatic duct and Dner negative cells and Ddr1 negative cells in the duodenum is observed as visualized by fluorescent staining.

In an ES culture differentiated to become mainly endoderm with some pancreatic cells it is seen that Dner binding reagent binds specifically to the endocrine pre-progenitor cells of the pancreas but also to neural cells in general. Ddr1 binding reagent will also bind to the endocrine pre-progenitor cells, but in addition to the ductal/endocrine progenitor cells in the pancreas. However, in contrast to Dner binding reagent, Ddr1 binding reagent will not bind to neural cells but do react to other endodermal cells than pancreatic cells. Thus, by first using Ddr1 binding reagent the ductal/endocrine endodermal cells will be purified together with some other endoderm, but by then using Dner binding reagent simultaneously or sequentially only the endocrine pre-progenitor cells, endocrine progenitor cells, and early endocrine cells, however, not fully differentiated endocrine cells will be purified. However, as Dner immunoreactivity appears to be stronger at e15.5 than at e18.5 and in the adult Islet this could be used to selectively purify only the endocrine pre-progenitor cells and the endocrine progenitors. The resulting cell population will have a low ratio of other cell types, such as other endoderm and neural cell types.

In some aspects localization of Ddr1 in the e15.5 mouse pancreas visualized by fluorescent staining can be performed according to Example 4 of PCT/EP2008/068061 and results hereof are shown therein.

Example 8

Localization of DNER, Insulin and Glucagon in the WG21 Human Pancreas Visualized by Fluorescent Staining Fluorescent stainings were carried out to determine localization of Dner, insulin and glucagon in the human WG21 pancreas. The sections were first deparaffinised. Goat anti-Dner (R&D Systems, 0.2 mg/ml) was used at 1:75 (i.e. 2.7 μg/ml), and was developed with TSA-cy3. Insulin was detected with guinea pig anti-human insulin 1:100 (Abcam, whole serum) and glucagon with rabbit anti-human glucagon 1:100 (DAKO, whole serum). The staining was developed with donkey anti-guinea pig-Cy2 and donkey anti-rabbit-Cy5. See Example 4 herein for a description of methods.

Results show that DNER expression was found in the human pancreas. Some cells are strongly positive for DNER and some are weakly positive. The DNER strongly positive cells are generally not found to co-express insulin or glucagon. However, some of the DNER weakly positive cells are positive for insulin or glucagon.

Example 9

Sorting of alphaTC Cells Using Dner

Dner sorting of alphaTC was carried out by analytical FACS sorting using cells that had been fixed for 45 minutes in Lillys fixative. To remove supernatant cells were pelleted by 1400 rpm in 10 minutes at RT in 2 ml tubes. Following this cells were washed in PBS with 0.1% BSA and cells were blocked by adding serum to reach 10% serum (final concentration) from the animal where the secondary antibody is raised, block for 1 h. Cells were then pelleted and supernatant removed. Primary antibody solution was added and incubated O/N at RT. The next day cells were washed 3×5 minutes in 2 ml tubes (using 1.8 ml). Secondary antibody was added and incubated for 1 hour at RT. Cells were washed 3×5 min in PBS with 0.1% BSA (using 1.8 ml). Finally, cells were assayed by FACS. Specifically, goat anti-Dner was used 1:150 and developed with donkey anti-goat-cy2 (1:300).

Figure 7:
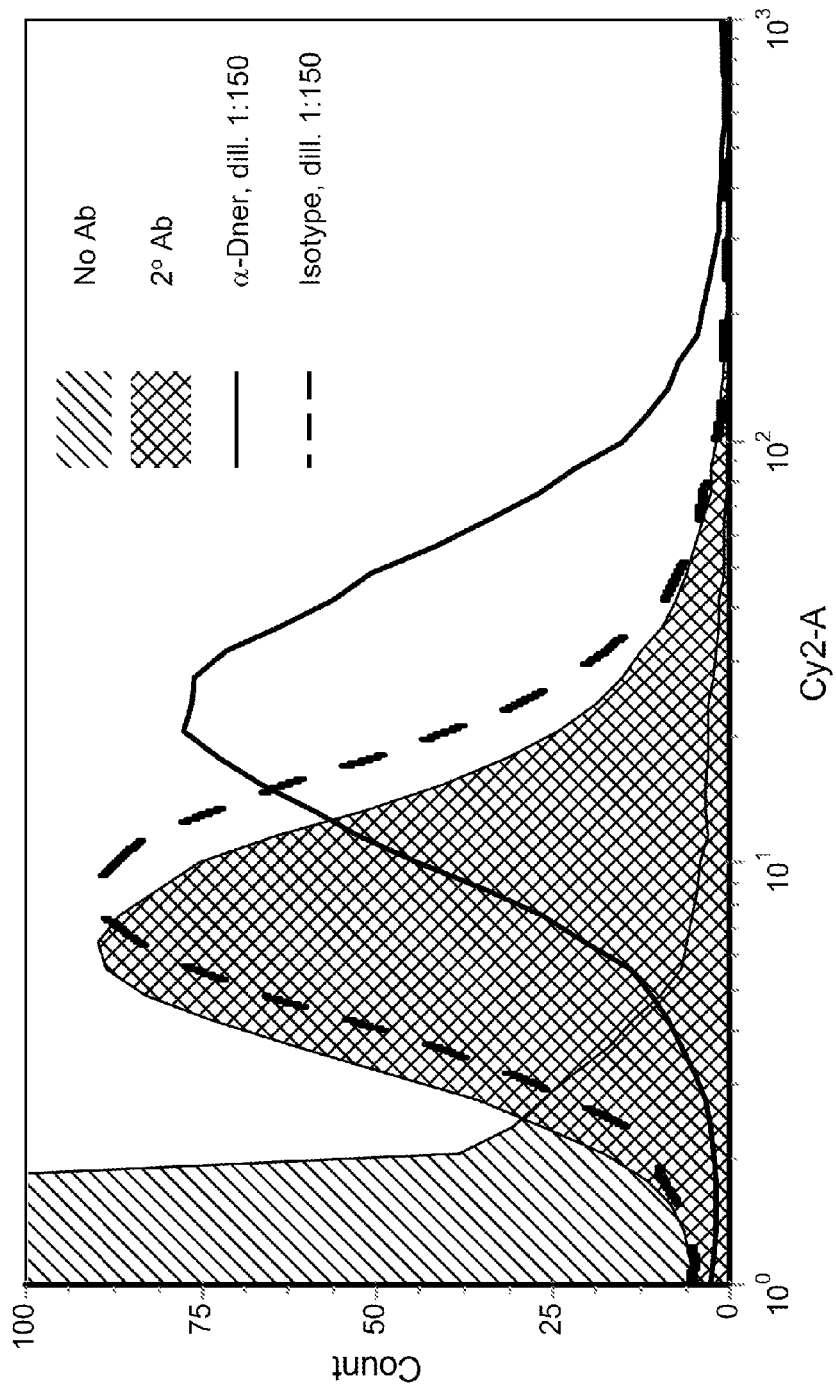
FIG. 7: FACS of alphaTC with Dner antibody. Performing FACS of alphaTC that have been incubated with neither primary goat anti-Dner antibody nor secondary donkey anti-goatCy2 antibody results in a cell population with very weak in Cy2 fluorescence (i.e. background). Adding the secondary donkey anti-goatCy2 antibody results in a marked increase in fluorescence—this is due to the non-specific binding of the secondary antibody to the cells (i.e. background). Addition of a primary goat IgG isotype control results in almost the same fluorescence as for secondary antibody alone (i.e. background). However, addition of goat anti-Dner results in a marked increase in fluorescence, demonstrating that the Dner protein can be used as tag in FACS.

The results are shown in FIG. 7: FACS of alphaTC with Dner antibody. The results showed that performing FACS of alphaTC that have been incubated with neither primary goat anti-Dner antibody nor secondary donkey anti-goatCy2 antibody resulted in a cell population with very weak in Cy2 fluorescence (i.e. background). Addition of the secondary donkey anti-goatCy2 antibody resulted in a marked increase in fluorescence—this was due to the non-specific binding of the secondary antibody to the cells (i.e. background). Addition of a primary goat IgG isotype control resulted in almost the same fluorescence as for secondary antibody alone (i.e. background). However, addition of goat anti-Dner resulted in a marked increase in fluorescence, demonstrating that the Dner protein can be used as tag in FACS.

ES cell culture differentiated to become mainly endoderm with pancreas cells and some neural cells can be purified by FACS in the same way as alpha cells. By sorting using the marker Dner it is likely that the endocrine pre-progenitor population will be purified together with some neural cells. By sorting using the marker Ddr1 the ductal/endocrine progenitors, endocrine pre-progenitor, endocrine progenitor, and/or early endocrine cells will be purified (also containing the Dner endocrine pre-progenitor cells) together with other endodermal cells. However, carrying out the double sorting using the markers Ddr1 and Dner in combination would result in a population of pure endocrine pre-progenitors, endocrine pro-genitors, and/or early endocrine cells. A double sorting might not be needed if the starting population only consist of endoderm of pancreatic origin without neural cells.

In some aspects sorting of cells, such as betaTC3 cells, using Ddr1 via FACS can be performed according to Example 5 of PCT/EP2008/068061 and results hereof are shown therein.

Example 10

Sorting of Dner Positive Cells from the e15.5 Mouse Pancreas by FACS

The aim of the experiment was to investigate if primary cells could be sorted for Dner.

Pancreata from NMRI e15.5 embryos were isolated by micro-dissection in ice cold PBS. Single cells were made from the tissue by incubating with Acutase at 30° C. for about one hour or until single cells are obtained, depending on, e.g., the amount of tissue. Cells were washed two times in 10 ml v-tubes by adding 5 ml of ice cold DMEM/F12+P/S and pellet cells at 1200 rpm for 5 minutes at 4 degrees and resuspended in 3 ml DMEM/F12+P/S+10% FCS. Cells were then reincubated at 37° C. for 2.5 hours, pelleted and resuspended in ice cold PBS+0.1% BSA. Primary antibody solution (rat anti-mDner, IgG1 type, 10 µg/ml or isotype, 10 µg/ml) was added and incubated for 45 minutes on ice. Cells were washed three times with 5 ml of PBS+0.1% BSA in v-tubes. Secondary antibody (donkey anti-rat-cy2, Jackson ImmunoResearch, stock concentration 1.5 mg/ml, used at 1:300, i.e. 5 µg/ml) was added and incubated for 30 minutes on ice. Cells were washed three times with 5 ml of PBS+0.1% BSA in v-tubes. Finally, cells were assayed by FACS.

Figure 8A:
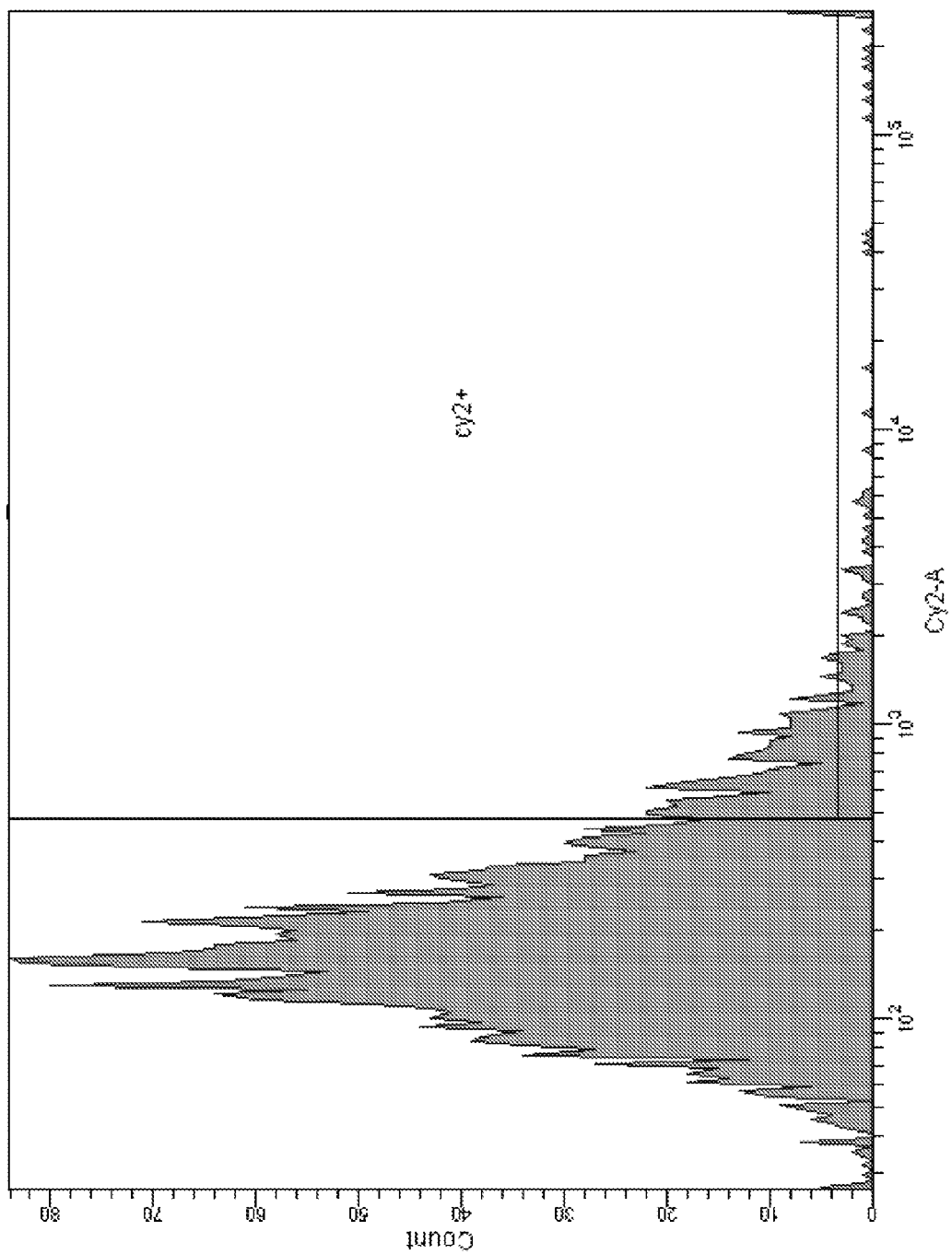
FIG. 8. FACS of e15.5 mouse pancreas cells with Dner antibody (A) and isotype control (B).
Figure 8B:
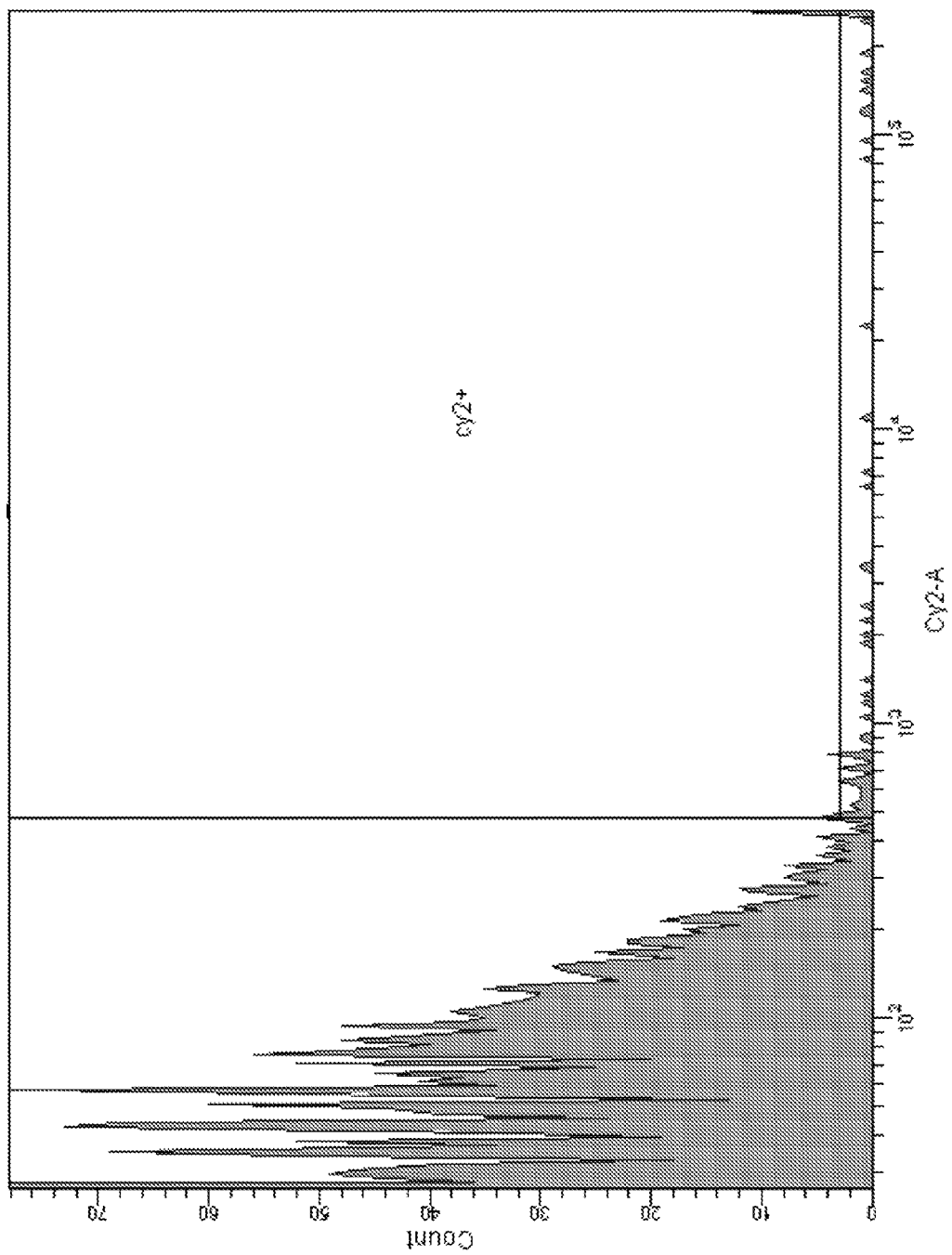

Results are shown in FIG. 8 shows results using the Dner antibody at 10 µg/ml (A) and IgG1 isotype control at 10 µg/ml (B). Results showed that with specific antibody compare to isotype antibody the e15.5 cell population is shifted to a marked higher fluorescence.

In some aspects mouse embryonic pancreatic cells using Ddr1 via FACS can be performed according to Example 6 of PCT/EP2008/068061 and results hereof are shown therein.

Example 11

Characterisation Dner Positive Cells from the e15.5 Mouse Pancreas Sorted by FACS The aim of the experiment is to determine what cell types the Dner positive cells from the embryonic pancreas give rise to and to test the potential of such cells.

Cells that are Dner positive and negative are sorted from the embryonic pancreas as in Example 10 herein. The two cells populations are implanted under the kidney capsule as described by Kroon, E. et al. (2008), Nat Biotechnol 26, 443-452. Transplant is treated and stained by IHC according to Examples 4 and 6 herein. Following in vivo maturation transplanted cells are recovered in vitro and tested functionally, such as test of glucose-regulated insulin secretion. It is expected that the implants with the Dner positive population will comprise insulin/glucagon expressing cells and that the implants with the Dner negative cells will comprise the exocrine cells and thus stain positive for amylase and DBA. Thus will the Dner positive cells also be able to normalize blood sugar levels.

In some aspects detection of insulin production in fetal pancreatic-derived cells or ES-derived cells isolated via Ddr1 using FACS can be performed according to Example 7 or 8 of PCT/EP2008/068061.

Example 12

Expression of Ddr1 and Dner in Human ES Cells Differentiated to the Pancreas Fate In order to determine expression of DDR1 and DNER in hES cells differentiated to pancreatic fate such cells may be fixed and stained according to the procedure described in Example 4 herein.

Example 13

Purification of Pancreatic Endocrine Cells Differentiated from hES Cells

The aim of the experiment is to purify beta cells and other endocrine cells and there endocrine committed precursors.

Embryonic stem cells may be isolated and differentiated according to the protocol described by Kroon, E. et al. (2008), Nat Biotechnol 26, 443-452 until stage 4 is reached. To purify subpopulations of ductal-endocrine progenitor cells, endocrine pre-progenitor cells, endocrine progenitor cells or early endocrine cells ES-derived cells are made into single cells and stained for Dner and Ddr1 alone or in combination as described in Example 6 herein with the following modifications: Mouse anti-Ddr1 (R&D Systems, MAB2396) and mouse anti-Dner (R&D Systems, MAB3646) antibodies are used. After secondary antibody and wash cells are not fixed but sorted live on a FACSArian into two tubes containing DMEM/F12+10% FCS+P/S. The positive cells are sorted into a first tube. The negative cells are sorted into another tube. Hereafter cells are implanted under the kidney capsule, tested and characterized as described by Kroon, E. et al. (2008), Nat Biotechnol 26, 443-452It is expected that the implants from the positive population will comprise insulin/glucagon expressing cells and that the implants with the negative cells will comprise amylase positive cells.

Example 14

Localization of Lrp11, Disp2 and Sez6l2

In-situ hybridization (ISH) was performed for Lrp11, Disp2 and Sez6l2 on cryo sections from adult mouse pancreas. Specific ISH signal was observed in the endocrine islet of Langerhans. Also at e18.5 and e15.5 ISH signal was localized to the endocrine compartment. This was confirmed by the use of antibodies recognizing Lrp11, Disp2 or Sez6l2. IHC in the adult pancreas showed that Lrp11, Disp2 and Sez6l2 all co-localized with hormone producing cells in the endocrine islet of Langerhans. In the embryonic pancreas some of the cells positive for Lrp11, Disp2 or Sez6l2 did co-express hormones while others did not coexpress a hormone. But at all times the Lrp11, Disp2 or Sez6l2 IHC signal was found in the central endocrine domain of the embryonic pancreas.

Example 15

Sorting of Disp2 or Sez6l2 Positive Cells by FACS

Experiments have shown that adult islets form mice can be FACS sorted by using monoclonal antibodies to Disp2. Rabbit serum specific for Sez6l2 have been used to FACS sort betaTC cells.

Example 16

Optimisation of In Vitro Protocol for the Diffentiation of Stem Cells by Quantification of the Expression of DNER, DDR1, and/or Ngn3

For efficient optimization of ES differentiation it is very important to have markers identifying the various stages of development of pancreatic cells into fully differentiated endocrine cells (see FIG. 1). Dner, Ddr1, and Ngn3 may in combination be used to pinpoint important and specific stages of cellular differentiation which until now not have been possible to detect using other markers. Dner, Ddr1, and Ngn3 may be used in combination with one or more additional markers.

Identification of endocrine pre-progenitor cells, endocrine progenitor cells, early endocrine cells, and/or fully differentiated endocrine cells may be achieved by contacting the cell population with a Dner binding reagent, Ddr1 binding reagent, and/or a binding reagent for another endoderm marker (e.g., Pdx1 or E-cadherin binding reagent) and evaluating the staining. The choice of binding reagent may depend on whether neural cells are present in the cell culture because Ddr1 will mark endoderm and not neural cells innervating the pancreas. However, high expression levels of Dner mark cells that are endocrine pre-progenitors or endocrine progenitors committed to become endocrine cells. By co-staining for Ngn3 and Ddr1 cells that are triple positive can be grouped into the endocrine progenitor group and cells that have high level of Dner immunoreactivity and are devoid of Ngn3 but have Ddr1 immunoreactivity will belong to the endocrine pre-progenitor cells. This analysis may be carried out using a method such as FACS, IHC, or panning.

In some aspects the method of optimisation of an in vitro protocol for the differentiation of stem cells is a method of screening for optimal culture conditions.

In some aspects the method of optimisation of an in vitro protocol for the differentiation of stem cells comprises of the steps of:
 a) quantifying DNER positive cells by 1) contacting a population of cells with a DNER binding reagent and 2) determining the quantity of cells exhibiting DNER as a cell surface marker (DNER positive cells);
 b) optionally separating the cells that bind the DNER binding reagent in a fraction of DNER positive cells from cells that do not bind the DNER binding reagent;
 c) optionally expanding the number of pancreatic cells selected from the group consisting of ductal/endocrine progenitor cells, endocrine progenitor cells, and early endocrine cells by culturing the population of cells comprising DNER positive cells under conditions which facilitate expansion of the cell type(s) obtained;
 d) culturing the population of cells comprising DNER positive cells under conditions which facilitate their differentiation into pancreatic cells selected from the group consisting of ductal/endocrine progenitor cells, endocrine progenitor cells, early endocrine cells, and fully differentiated endocrine cells;
 e) optionally expanding the number of pancreatic cells selected from the group consisting of ductal/endocrine progenitor cells, endocrine progenitor cells, and early endocrine cells by culturing the population of cells comprising DNER positive cells under conditions which facilitate expansion of the cell type(s) obtained;
 f) quantifying DNER positive cells by 1) contacting a population of cells with a DNER binding reagent and 2) determining the quantity of cells exhibiting DNER as a cell surface marker (DNER positive cells);
 g) determining whether the quantity of DNER positive cells in step f) is larger than the quantity of DNER positive cells in step a);
 h) optionally separating the cells that bind the DNER binding reagent in a fraction of DNER positive cells from cells that do not bind the DNER binding reagent;
 i) optionally introducing an adjustment of culture conditions in order to increase the quantity of DNER positive cells by varying conditions which affect differentiation, such as 1) concentration or combination of differentiation factors, 2) concentration or composition of growth media, 3) concentration or composition of supplements to the growth media, 4) time of incubation, and/or 5) oxygen tension;
 j) optionally separating the cells that bind the DNER binding reagent in a fraction of DNER positive cells from cells that do not bind the DNER binding reagent;
 k) repeating the sequence of steps a) to h) until a satisfactory quantity of DNER positive cells has been obtained.

In some aspects the method of optimisation of an in vitro protocol for the differentiation of stem cells comprises the sequential use of a DDR1 binding reagent and a DNER binding reagent. In some aspects the use of a DDR1 binding reagent takes place before the use of a DNER binding reagent. The above method relating to use of a DNER binding reagent as defined by steps a) to k) may be combined with the use of a DDR1 binding reagent, such as the use of the following steps α) to γ) before step a) and/or before step d):
 α) quantifying DDR1 positive cells by 1) contacting a population of cells with a DDR1 binding reagent and 2) determining the quantity of cells exhibiting DDR1 as a cell surface marker (DDR1 positive cells);
 β) optionally separating the cells that bind the DDR1 binding reagent in a fraction of DDR1 positive cells from cells that do not bind the DDR1 binding reagent;
 χ) optionally expanding the number of pancreatic cells selected from the group consisting of ductal/endocrine progenitor cells, endocrine progenitor cells, and early endocrine cells by culturing the population of cells comprising DDR1 positive cells under conditions which facilitate expansion of the cell type(s) obtained;

In some aspects the method of optimisation of an in vitro protocol for the differentiation of stem cells comprises the sequential use of a DDR1 binding reagent, a DNER binding reagent and an LRP11 and/or DISP2 and/or SEZ6L2 and/or SLC30A8 binding reagent, wherein the use of a DNER binding reagent may be as defined by steps a) to k) above and the use of a DDR1 binding reagent may be as defined by steps α) to γ) above and used before step a) and/or before step d) as well as after step γ) or c):
 i) quantifying LRP11, DISP2, SEZ6L2 and/or SLC30A8 positive cells by 1) contacting a population of cells with a LRP11, DISP2, SEZ6L2 and/or SLC30A8 binding reagent and 2) determining the quantity of cells exhibiting LRP11, DISP2, SEZ6L2 and/or SLC30A8 as a cell surface marker (LRP11, DISP2, SEZ6L2 and/or SLC30A8 positive cells);
 ii) optionally separating the cells that bind the LRP11, DISP2, SEZ6L2 and/or SLC30A8 binding reagent in a fraction of LRP11, DISP2, SEZ6L2 and/or SLC30A8 positive cells from cells that do not bind the LRP11, DISP2, SEZ6L2 and/or SLC30A8 binding reagent.

In some aspects the method of optimisation of an in vitro protocol for the differentiation of stem cells comprises the sequential use of a DDR1 binding reagent and an LRP11 and/or DISP2 and/or SEZ6L2 and/or SLC30A8 binding reagent, wherein the use of a DDR1 binding reagent may be as defined by steps α) to γ) above and a LRP11, DISP2, SEZ6L2, and/or SLC30A8 binding reagent is used as defined by steps i) and ii) after step γ).

In some aspects determination of the quantity DNER and/or DDR1 positive cells may be carried out using an automated staining system, e.g., with fluorescence detection.

Identification of endocrine progenitor cells, and/or early endocrine cells may be achieved by contacting the cell population with a DDR1 binding reagent, optionally in combination with an additional binding reagent for another endodermal marker (e.g., Pdx1 binding reagent) and evaluating the staining. The choice of binding reagent may depend on the composition of the cells culture, such as whether neural cells are present in the cell culture because DDR1 will mark endoderm and not neural cells innervating the pancreas. By costaining for Ngn3 and DDR1 cells that are double positive can be grouped into the endocrine progenitor group. This analysis may be carried out using a method such as FACS, MACS, IHC, or panning.

In some aspects optimisation of in vitro protocol for the differentiation of stem cells by quantification of DDR1 can be performed according to Example 9 of PCT/EP2008/068061.

The invention described herein was made through support by a grant (#5U01-DK072473) from NIH/NIDDK through Vanderbilt University.

EMBODIMENTS OF THE INVENTION

1. A method of identification of cells comprising cells selected from the group consisting of endocrine pre-progenitor cells, endocrine progenitor cells, early endocrine cells, and/or fully differentiated endocrine cells, the method comprising contacting a cell population comprising pancreatic cells with one or more binding reagents selected from the group consisting of DNER, DISP2, SEZ6L2, LRP11 and SLC30A8 binding reagent.
2. A method of identification of cells comprising cells selected from the group consisting of endocrine pre-progenitor cells, endocrine progenitor cells, early endocrine cells, and/or fully differentiated endocrine cells, the method comprising contacting a cell population comprising pancreatic cells with a DNER binding reagent.
3. A method of obtaining a culture of cells comprising cells selected from the group consisting of endocrine pre-progenitor cells, endocrine progenitor cells, early endocrine cells, and/or fully differentiated endocrine cells, the method comprising: contacting a cell population comprising pancreatic cells with one or more binding reagents selected from the group consisting of DNER, DISP2, SEZ6L2, LRP11 and SLC30A8 binding reagent and separating the cells that binds the DNER, DISP2, SEZ6L2, LRP11 and/or SLC30A8 binding reagent in a fraction of DNER, DISP2, SEZ6L2, LRP11 and/or SLC30A8 positive cells from cells that do not bind the DNER, DISP2, SEZ6L2, LRP11 and/or SLC30A8 binding reagent.
4. A method of obtaining a culture of cells comprising cells selected from the group consisting of endocrine pre-progenitor cells, endocrine progenitor cells, early endocrine cells, and/or fully differentiated endocrine cells, the method comprising: contacting a cell population comprising pancreatic cells with a DNER binding reagent and separating the cells that binds the DNER binding reagent in a fraction of DNER positive cells from cells that do not bind the DNER binding reagent.
5. A method of obtaining a culture of cells comprising cells selected from the group consisting of endocrine pre-progenitor cells, endocrine progenitor cells, early endocrine cells, and/or fully differentiated endocrine cells, the method comprising: obtaining cells purified according to the method of embodiment 3 or 4 and then subsequently culturing the obtained cells under conditions which facilitate differentiation of the pancreatic cells into cells selected from the group consisting of endocrine pre-progenitor cells, endocrine progenitor cells, early endocrine cells, and/or fully differentiated endocrine cells.
6. A method of obtaining a culture of cells comprising cells selected from the group consisting of endocrine pre-progenitor cells, endocrine progenitor cells, early endocrine cells, and/or fully differentiated endocrine cells, the method comprising: obtaining cells purified according to the method of embodiment 3 or 4 and then subsequently culturing the obtained cells under conditions which facilitate differentiation of the cells into pancreatic cells comprising cells selected from the group consisting of endocrine pre-progenitor cells, endocrine progenitor cells, early endocrine cells, and/or fully differentiated endocrine cells.
7. A method of expanding the number of cells comprising cells selected from the group consisting of endocrine pre-progenitor cells, endocrine progenitor cells, early endocrine cells, and/or fully differentiated endocrine cells, the method comprising: obtaining cells purified according to embodiment 3 or 4 and then subsequently culturing the obtained cells under conditions which facilitate expansion of the cell type(s) obtained.
8. A method of expanding the number of cells comprising cells selected from the group consisting of endocrine pre-progenitor cells, endocrine progenitor cells, early endocrine cells, and/or fully differentiated endocrine cells, the method comprising: obtaining cells purified and expanded according to embodiment 7 and then subsequently culturing the obtained cells under conditions which facilitates differentiation of the pancreatic cells into cells selected from the group consisting of endocrine pre-progenitor cells, endocrine progenitor cells, early endocrine cells, and/or fully differentiated endocrine cells.
9. A method of expanding the number of cells comprising cells selected from the group consisting of endocrine pre-progenitor cells, endocrine progenitor cells, early endocrine cells, and/or fully differentiated endocrine cells, the method comprising: obtaining cells purified and expanded according to embodiment 7 and then subsequently culturing the obtained cells under conditions which facilitates differentiation of the cells into pancreatic cells selected from the group consisting of endocrine pre-progenitor cells, endocrine progenitor cells, early endocrine cells, and/or fully differentiated endocrine cells.
10. A method of providing pancreatic endocrine function to a mammal deficient in its production of at least one pancreatic hormone wherein cells are obtained by the method according to any one of embodiments 1-9, the method further comprising the steps of: implanting into the mammal the obtained cells in an amount sufficient to produce a measurable amount of at least one pancreatic hormone in the mammal.
11. The method according to embodiment 10, wherein the amount of pancreatic hormone is determined no earlier than the day after the transplantation or after in vivo maturation, such as at least 1, 2, 3 or 4 weeks after transplantation.
12. The method according to embodiment 10 or 11, wherein said at least one pancreatic hormone is insulin.
13. The method according to any of embodiments 10-12, wherein the mammal is a human being.
14. The method according to any one of the preceding embodiments, wherein said at least one pancreatic hormone is selected from the group consisting of insulin, glucagon, somatostatin, pancreatic polypeptide, and ghrelin.
15. A method of quantifying DNER, DISP2, SEZ6L2, LRP11 and/or SLC30A8 positive cells comprising pancreatic cells by a) contacting the cells with one or more binding reagents selected from the group consisting of DNER, DISP2, SEZ6L2, LRP11 and SLC30A8 binding reagent; and b) determining the quantity of cells that exhibit DNER, DISP2, SEZ6L2, LRP11 and/or SLC30A8 as a cell surface marker (DNER, DISP2, SEZ6L2, LRP11 and/or SLC30A8 positive cells).
16. A method of quantifying DNER positive cells comprising pancreatic cells by a) contacting the cells with a DNER binding reagent; and b) determining the quantity of cells that exhibit DNER as a cell surface marker (DNER positive cells).

17. A method for the optimisation of an in vitro protocol, wherein the number of DNER, DISP2, SEZ6L2, LRP11 and/or SLC30A8 expressing cells (DNER, DISP2, SEZ6L2, LRP11 and/or SLC30A8 positive cells) is periodically monitored.

18. A method for the optimisation of an in vitro protocol, wherein the number of DNER expressing cells (DNER positive cells) is periodically monitored.

19. The method according to any one of the preceding embodiments, wherein one or more additional binding reagents are used in combination with one or more binding reagents selected from the group consisting of DNER, DISP2, SEZ6L2, LRP11 and SLC30A8 binding reagent either simultaneously or sequentially.

20. The method according to any one of the preceding embodiments, wherein one or more additional binding reagents are used in combination with the DNER, DISP2, SEZ6L2, LRP11 and/or SLC30A8 binding reagent either simultaneously or sequentially.

21. The method according to any one of the preceding embodiments, wherein one or more additional binding reagents are used in combination with the DNER binding reagent either simultaneously or sequentially.

22. The method according to any of embodiments 20 or 21, wherein an additional binding reagent is selected from the group consisting of DDR1, prominin 1 (also known as CD133), and CD49f binding reagents.

23. The method according to any of embodiments 20 or 21, wherein the additional binding reagent is a DDR1 binding reagent.

24. The method according to any one of the preceding embodiments, wherein the DNER, DISP2, SEZ6L2, LRP11 and/or SLC30A8 positive cells are differentiated further into insulin producing cells, optionally together with cells differentiated further into cells selected from the group consisting of glucagon, somatostatin, pancreatic polypeptide, and/or ghrelin producing cells.

25. The method according to any one of the preceding embodiments, wherein the DNER positive cells are differentiated further into insulin producing cells, optionally together with cells differentiated further into cells selected from the group consisting of glucagon, somatostatin, pancreatic polypeptide, and/or ghrelin producing cells.

26. The method according to any one of the embodiments 1-25, wherein the cell population comprising pancreatic cells is obtained from a pancreas.

27. The method according to any one of the embodiments 1-25, wherein the cell population comprising pancreatic cells is obtained from a somatic cell population.

28. The method according to embodiment 27, wherein the somatic cell population has been induced to de-differentiate into pluripotent cells such as ES like-cells.

29. The method according to any one of the embodiments 1-25, wherein the cell population comprising pancreatic cells is obtained from pluripotent cells such as ES cells.

30. The method according to any one of the preceding embodiments, wherein the cell population comprising pancreatic cells is of vertebrate origin.

31. The method according to any one of the preceding embodiments, wherein the cell population comprising pancreatic cells is of mammalian origin.

32. The method according to any one of the preceding embodiments, wherein the cell population comprising pancreatic cells is of human origin.

33. The method according to any one of the preceding embodiments, wherein the cell population comprising pancreatic cells is of mouse origin.

34. The method according to any one of the preceding embodiments, wherein the cell population comprising pancreatic cells is of rat origin.

35. The method according to any one of the preceding embodiments, wherein the cell population comprising pancreatic cells is of chicken origin.

36. The method according to any of embodiments 30-35, wherein the cell population has been differentiated to the pancreatic endocrine lineage.

37. The method according to embodiment 36, wherein differentiation of the cells comprises culturing the cells in a medium comprising one or more differentiation factor(s).

38. The method according to any one of the preceding embodiments, wherein the cell population comprising pancreatic cells is a beta cell-positive fraction.

39. The method according to any one of the preceding embodiments, wherein the cell population comprising pancreatic cells is a ptprn/IA2-positive fraction.

40. The method according to any one of the preceding embodiments, wherein the cell population comprising pancreatic cells is an Abcc8/Sur1-positive fraction.

41. The method according to any one of the preceding embodiments, wherein the cell population comprising pancreatic cells is a Slc30a8/ZnT-8-positive fraction.

42. The method according to any one of the preceding embodiments, wherein the culture of pancreatic endocrine cells obtained by the method according to any of the embodiments above or herein is further separated in a beta cell-positive fraction.

43. The method according to any one of the preceding embodiments, wherein the culture of pancreatic endocrine cells obtained by the method according to any of the embodiments above or herein is further separated in a ptprn/IA2-positive fraction.

44. The method according to any one of the preceding embodiments, wherein the culture of pancreatic endocrine cells obtained by the method according to any of the embodiments above or herein is further separated in an Abcc8/Sur1-positive fraction.

45. The method according to any one of the preceding embodiments, wherein the culture of pancreatic endocrine cells obtained by the method according to any of the embodiments above or herein is further separated in a Slc30a8/ZnT-8-positive fraction.

46. The method according to any one of the preceding embodiments, wherein the DNER binding reagent is an antibody that specifically binds to the DNER protein.

47. The method according to any one of the preceding embodiments, wherein the Disp2 binding reagent is an antibody that specifically binds to the Disp2 protein.

48. The method according to any one of the preceding embodiments, wherein the Sez6l2 binding reagent is an antibody that specifically binds to the Sez6l2 protein.

49. The method according to any one of the preceding embodiments, wherein the Lrp11 binding reagent is an antibody that specifically binds to the Lrp11 protein.

50. The method according to any one of the preceding embodiments, wherein the Slc30a8 binding reagent is an antibody that specifically binds to the Slc30a8 protein.

51. The method according to any one of the preceding embodiments, wherein the DDR1 binding reagent is an antibody that specifically binds to the DDR1 protein.

52. The method according to any one of the preceding embodiments, wherein the step of separating or monitoring is done by fluorescence activated cell sorting.

53. The method according to any one of the preceding embodiments, wherein the step of separating or monitoring is done by magnetic activated cell sorting.
54. The method according to any one of the preceding embodiments, wherein the step of separating is done by panning.
55. The method according to any one of the preceding embodiments, wherein the cells are endocrine pre-progenitor cells.
56. The method according to any one of the preceding embodiments, wherein a Disp2 binding reagent is used in stead of the DNER binding reagent.
57. The method according to any one of the preceding embodiments, wherein a Sez6l2 binding reagent is used in stead of the DNER binding reagent.
58. The method according to any one of the preceding embodiments, wherein an Lrp11 binding reagent is used in stead of the DNER binding reagent.
59. The method according to any one of the preceding embodiments, wherein a Slc30a8 binding reagent is used in stead of the DNER binding reagent.
60. The method according to any one of the preceding embodiments, wherein a Disp2 binding reagent is used in combination with a DDR1 binding reagent in stead of the DNER binding reagent.
61. The method according to any one of the preceding embodiments, wherein a Sez6l2 binding reagent is used in combination with a DDR1 binding reagent in stead of the DNER binding reagent.
62. The method according to any one of the preceding embodiments, wherein an Lrp11 binding reagent is used in combination with a DDR1 binding reagent in stead of the DNER binding reagent.
63. The method according to any one of the preceding embodiments, wherein a Slc30a8 binding reagent is used in combination with a DDR1 binding reagent in stead of the DNER binding reagent.
64. An isolated cell selected from the group consisting of endocrine pre-progenitor cells, endocrine progenitor cells, early endocrine cells and fully differentiated endocrine cells obtained by a method as defined in any of the embodiments 1-63.
65. The isolated cell according to embodiment 64, wherein said isolated cell is an endocrine pre-progenitor cell.
66. The isolated cell according to embodiment 64, wherein said isolated cell is a fully differentiated endocrine cell.
67. A composition comprising isolated cells selected from one or more cells from the group consisting of endocrine pre-progenitor cells, endocrine progenitor cells, early endocrine cells and fully differentiated endocrine cells obtained by a method as defined in any of the embodiments 1-63.
68. Use of a binding reagent selected from the group consisting of DNER, DISP2, SEZ6L2, LRP11 and/or SLC30A8 binding reagent to identify or select cells that express DNER, DISP2, SEZ6L2, LRP11 and/or SLC30A8 protein as a cell surface marker.
69. Use of a DNER binding reagent to identify or select cells that express DNER protein as a cell surface marker.
70. Use of DNER, DISP2, SEZ6L2, LRP11 and/or SLC30A8 protein as a cell surface marker to obtain a culture of pancreatic endocrine cells.
71. Use of DNER protein as a cell surface marker to obtain a culture of pancreatic endocrine cells.
72. Use according to embodiment 70 or 71, wherein one or more further cell surface markers are used simultaneously or sequentially to obtain a culture of pancreatic endocrine cells.
73. Use according to embodiment 72, wherein a further cell surface marker is selected from the group consisting of DDR1 protein, prominin 1 (also known as CD133), and CD49f.
74. Use according to embodiment 72, wherein a further cell surface marker is DDR1 protein.
75. Use according to any of embodiments 68-74, wherein a Disp2 binding reagent is used in stead of the DNER binding reagent.
76. Use according to any of embodiments 68-74, wherein a Sez6l2 binding reagent is used in stead of the DNER binding reagent.
77. Use according to any of embodiments 68-74, wherein an Lrp11 binding reagent is used in stead of the DNER binding reagent.
78. Use according to any of embodiments 68-74, wherein a Slc30a8 binding reagent is used in stead of the DNER binding reagent.
79. Use according to any of embodiments 68-74, wherein a Disp2 binding reagent is used in combination with a DDR1 binding reagent in stead of the DNER binding reagent.
80. Use according to any of embodiments 68-74, wherein a Sez6l2 binding reagent is used in combination with a DDR1 binding reagent in stead of the DNER binding reagent.
81. Use according to any of embodiments 68-74, wherein an Lrp11 binding reagent is used in combination with a DDR1 binding reagent in stead of the DNER binding reagent.
82. Use according to any of embodiments 68-74, wherein a Slc30a8 binding reagent is used in combination with a DDR1 binding reagent in stead of the DNER binding reagent.

The invention claimed is:

1. A method of identifying cells that have the potential to differentiate into pancreatic cells, the method comprising contacting a cell population comprising cells selected from the group consisting of endocrine pre-progenitor cells, endocrine progenitor cells, early endocrine cells, and/or fully differentiated endocrine cells with a DNER binding reagent wherein the cells that bind to the DNER reagent (DNER-positive cells) have the potential to differentiate into pancreatic cells.

2. A method of obtaining a culture of cells according to claim 1, the method further comprising: separating the cells that bind the DNER binding reagent from cells that do not bind the DNER binding reagent wherein the cells that bind to the DNER reagent (DNER-positive cells) have the potential to differentiate into pancreatic cells.

3. A method of obtaining a culture of pancreatic cells, the method comprising: obtaining cells that bind the DNER reagent (DNER-positive cells) according to the method of claim 2 and then subsequently culturing the DNER-positive cells under conditions which facilitate differentiation of the DNER-positive cells into pancreatic cells.

4. A method of expanding the number of cells in a cell population that have the potential to differentiate into pancreatic cells, the method comprising: obtaining cells that bind the DNER reagent (DNER-positive cells) according to claim 2 and then subsequently culturing the obtained cells under conditions which facilitate expansion of the DNER-positive cell type(s) obtained.

5. A method of expanding the number of pancreatic cells in a cell population, the method comprising: obtaining cells expanded according to claim 4 and then subsequently culturing the obtained cells under conditions which facilitates differentiation of the cells into pancreatic cells.

6. A method of providing pancreatic endocrine function to a mammal deficient in its production of at least one pancreatic hormone, the method comprising the steps of: implanting into the mammal the cells obtained by the method according to claim 3 in an amount sufficient to produce a measurable amount of at least one pancreatic hormone in the mammal.

7. A method of quantifying DNER positive pancreatic cells by a) contacting the cells with a DNER binding reagent; and b) determining the quantity of cells that bind the DNER reagent (DNER positive cells).

8. The method according to claim 1, wherein one or more additional binding reagents are used in combination with the DNER binding reagent either simultaneously or sequentially.

9. The method according to claim 8, wherein an additional binding reagent is selected from the group consisting of DDR1, prominin 1 (also known as CD133), CD49f, DISP2, SEZ6L2, LRP11 and SLC30A8 binding reagents.

10. The method according to claim 1, wherein the DNER positive cells are differentiated further into insulin producing cells, optionally together with cells differentiated further into cells selected from the group consisting of glucagon, somatostatin, pancreatic polypeptide, and/or ghrelin producing cells.

11. An isolated cell obtained by a method according to claim 1.

12. A composition comprising cells obtained by a method according to claim 1.

* * * * *

UNITED STATES PATENT AND TRADEMARK OFFICE
CERTIFICATE OF CORRECTION

PATENT NO. : 8,399,251 B2  
APPLICATION NO. : 12/934373  
DATED : March 19, 2013  
INVENTOR(S) : Hald et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 159 days.

Signed and Sealed this  
Twentieth Day of August, 2013

Teresa Stanek Rea  
*Acting Director of the United States Patent and Trademark Office*

SEQUENCE LISTING

```
<160> NUMBER OF SEQ ID NOS: 7

<210> SEQ ID NO 1
<211> LENGTH: 737
<212> TYPE: PRT
<213> ORGANISM: Homo sapiens

<400> SEQUENCE: 1

Met Gln Pro Arg Arg Ala Gln Ala Pro Gly Ala Gln Leu Leu Pro Ala
1               5                   10                  15

Leu Ala Leu Leu Leu Leu Leu Leu Gly Ala Gly Pro Arg Gly Ser Ser
            20                  25                  30
```

```
Leu Ala Asn Pro Val Pro Ala Ala Pro Leu Ser Ala Pro Gly Pro Cys
            35                  40                  45

Ala Ala Gln Pro Cys Arg Asn Gly Gly Val Cys Thr Ser Arg Pro Glu
 50                  55                  60

Pro Asp Pro Gln His Pro Ala Pro Ala Gly Pro Gly Tyr Ser Cys
 65                  70                  75                  80

Thr Cys Pro Ala Gly Ile Ser Gly Ala Asn Cys Gln Leu Val Ala Asp
                    85                  90                  95

Pro Cys Ala Ser Asn Pro Cys His His Gly Asn Cys Ser Ser Ser Ser
                100                 105                 110

Ser Ser Ser Ser Asp Gly Tyr Leu Cys Ile Cys Asn Glu Gly Tyr Glu
            115                 120                 125

Gly Pro Asn Cys Glu Gln Ala Leu Pro Ser Leu Pro Ala Thr Gly Trp
        130                 135                 140

Thr Glu Ser Met Ala Pro Arg Gln Leu Gln Pro Val Pro Ala Thr Gln
145                 150                 155                 160

Glu Pro Asp Lys Ile Leu Pro Arg Ser Gln Ala Thr Val Thr Leu Pro
                165                 170                 175

Thr Trp Gln Pro Lys Thr Gly Gln Lys Val Val Glu Met Lys Trp Asp
                180                 185                 190

Gln Val Glu Val Ile Pro Asp Ile Ala Cys Gly Asn Ala Ser Ser Asn
            195                 200                 205

Ser Ser Ala Gly Gly Arg Leu Val Ser Phe Glu Val Pro Gln Asn Thr
        210                 215                 220

Ser Val Lys Ile Arg Gln Asp Ala Thr Ala Ser Leu Ile Leu Leu Trp
225                 230                 235                 240

Lys Val Thr Ala Thr Gly Phe Gln Gln Cys Ser Leu Ile Asp Gly Arg
                245                 250                 255

Ser Val Thr Pro Leu Gln Ala Ser Gly Gly Leu Val Leu Leu Glu Glu
                260                 265                 270

Met Leu Ala Leu Gly Asn Asn His Phe Ile Gly Phe Val Asn Asp Ser
        275                 280                 285

Val Thr Lys Ser Ile Val Ala Leu Arg Leu Thr Leu Val Val Lys Val
        290                 295                 300

Ser Thr Cys Val Pro Gly Glu Ser His Ala Asn Asp Leu Glu Cys Ser
305                 310                 315                 320

Gly Lys Gly Lys Cys Thr Thr Lys Pro Ser Glu Ala Thr Phe Ser Cys
                325                 330                 335

Thr Cys Glu Glu Gln Tyr Val Gly Thr Phe Cys Glu Glu Tyr Asp Ala
                340                 345                 350

Cys Gln Arg Lys Pro Cys Gln Asn Asn Ala Ser Cys Ile Asp Ala Asn
            355                 360                 365

Glu Lys Gln Asp Gly Ser Asn Phe Thr Cys Val Cys Leu Pro Gly Tyr
        370                 375                 380

Thr Gly Glu Leu Cys Gln Ser Lys Ile Asp Tyr Cys Ile Leu Asp Pro
385                 390                 395                 400

Cys Arg Asn Gly Ala Thr Cys Ile Ser Ser Leu Ser Gly Phe Thr Cys
                405                 410                 415

Gln Cys Pro Glu Gly Tyr Phe Ser Ala Cys Glu Glu Lys Val Asp
                420                 425                 430

Pro Cys Ala Ser Ser Pro Cys Gln Asn Asn Gly Thr Cys Tyr Val Asp
            435                 440                 445

Gly Val His Phe Thr Cys Asn Cys Ser Pro Gly Phe Thr Gly Pro Thr
```

```
                450                 455                 460
Cys Ala Gln Leu Ile Asp Phe Cys Ala Leu Ser Pro Cys Ala His Gly
465                 470                 475                 480

Thr Cys Arg Ser Val Gly Thr Ser Tyr Lys Cys Leu Cys Asp Pro Gly
                485                 490                 495

Tyr His Gly Leu Tyr Cys Glu Glu Tyr Asn Glu Cys Leu Ser Ala
                500                 505                 510

Pro Cys Leu Asn Ala Ala Thr Cys Arg Asp Leu Val Asn Gly Tyr Glu
                515                 520                 525

Cys Val Cys Leu Ala Glu Tyr Lys Gly Thr His Cys Glu Leu Tyr Lys
530                 535                 540

Asp Pro Cys Ala Asn Val Ser Cys Leu Asn Gly Ala Thr Cys Asp Ser
545                 550                 555                 560

Asp Gly Leu Asn Gly Thr Cys Ile Cys Ala Pro Gly Phe Thr Gly Glu
                565                 570                 575

Glu Cys Asp Ile Asp Ile Asn Glu Cys Asp Ser Asn Pro Cys His His
                580                 585                 590

Gly Gly Ser Cys Leu Asp Gln Pro Asn Gly Tyr Asn Cys His Cys Pro
                595                 600                 605

His Gly Trp Val Gly Ala Asn Cys Glu Ile His Leu Gln Trp Lys Ser
610                 615                 620

Gly His Met Ala Glu Ser Leu Thr Asn Met Pro Arg His Ser Leu Tyr
625                 630                 635                 640

Ile Ile Ile Gly Ala Leu Cys Val Ala Phe Ile Leu Met Leu Ile Ile
                645                 650                 655

Leu Ile Val Gly Ile Cys Arg Ile Ser Arg Ile Glu Tyr Gln Gly Ser
                660                 665                 670

Ser Arg Pro Ala Tyr Glu Glu Phe Tyr Asn Cys Arg Ser Ile Asp Ser
                675                 680                 685

Glu Phe Ser Asn Ala Ile Ala Ser Ile Arg His Ala Arg Phe Gly Lys
                690                 695                 700

Lys Ser Arg Pro Ala Met Tyr Asp Val Ser Pro Ile Ala Tyr Glu Asp
705                 710                 715                 720

Tyr Ser Pro Asp Asp Lys Pro Leu Val Thr Leu Ile Lys Thr Lys Asp
                725                 730                 735

Leu

<210> SEQ ID NO 2
<211> LENGTH: 737
<212> TYPE: PRT
<213> ORGANISM: Mus musculus

<400> SEQUENCE: 2

Met Pro Pro Arg Arg Ala Gln Ala Pro Gly Ala Pro Leu Leu Pro Val
1               5                   10                  15

Leu Ala Leu Leu Pro Leu Leu Leu Gly Ala Gly Pro Gln Ser Gly Cys
                20                  25                  30

Leu Ala Ser Pro Val Ser Ala Ala Pro Leu Pro Ala Pro Gly Pro Cys
            35                  40                  45

Ala Ser Gln Pro Cys Arg Asn Gly Gly Val Cys Thr Pro Arg Ser Val
            50                  55                  60

Thr Asp Gln Glu His Pro Ala Ala Asp Ala Glu Pro Arg Tyr Ser Cys
65                  70                  75                  80

Thr Cys Pro Ala Gly Val Ser Gly Thr Tyr Cys Gln Phe Val Ala Asp
                85                  90                  95
```

-continued

```
Pro Cys Ala Ser Asn Pro Cys His His Gly Asn Cys Ser Ser Ser Ser
            100                 105                 110

Ser Ser Ser Ser Asp Ser Tyr Leu Cys Ile Cys Asn Asp Gly Tyr Glu
            115                 120                 125

Gly Leu Asn Cys Glu Gln Pro Leu Pro Ser Ile Pro Thr Ser Gly Trp
        130                 135                 140

Thr Glu Ser Thr Ala Pro Arg Gln Leu Gln Pro Val Pro Ala Thr Gln
145                 150                 155                 160

Glu Pro Asp Ile Ile Leu Pro Arg Ser Gln Ala Thr Val Thr Leu Pro
                165                 170                 175

Thr Trp Gln Pro Lys Thr Gly Gln Lys Val Val Glu Met Lys Trp Asp
                180                 185                 190

Gln Val Glu Val Val Pro Asp Val Ala Cys Gly Asn Ala Ser Ser Asn
        195                 200                 205

Asn Ser Ala Gly Gly Arg Leu Val Ser Phe Glu Val Pro Gln Asn Thr
    210                 215                 220

Ser Val Lys Ile Arg Gln Asp Ala Asn Ser Leu Leu Ile Leu Leu Trp
225                 230                 235                 240

Lys Val Thr Ala Thr Gly Phe Gln Gln Cys Ser Leu Ile Asp Gly Arg
                245                 250                 255

Ser Val Thr Pro Leu Gln Ala Pro Gly Gly Leu Val Leu Glu Glu
                260                 265                 270

Met Leu Ala Leu Gly Pro Asn His Phe Ile Gly Phe Val Asn Asp Ser
        275                 280                 285

Val Ala Lys Ser Ile Val Ala Leu Arg Leu Thr Leu Val Val Lys Ala
    290                 295                 300

Ser Asn Cys Val Pro Gly Asp Ser His Ser Asn Asp Leu Glu Cys Ser
305                 310                 315                 320

Gly Lys Gly Lys Cys Ala Thr Lys Pro Ser Glu Ala Thr Phe Ser Cys
                325                 330                 335

Thr Cys Gln Asp Gln Tyr Ile Gly Thr Phe Cys Glu Glu Phe Asp Ala
        340                 345                 350

Cys Gln Arg Lys Pro Cys Gln Asn Glu Ala Ser Cys Ile Asp Ala Asn
    355                 360                 365

Glu Lys Gln Asp Gly Ser Asn Phe Thr Cys Leu Cys Leu Pro Gly Tyr
    370                 375                 380

Thr Gly Glu Leu Cys Gln Ser Lys Ile Asp Tyr Cys Val Leu Asp Pro
385                 390                 395                 400

Cys Arg Asn Gly Ala Thr Cys Val Ser Ser Leu Ser Gly Phe Thr Cys
                405                 410                 415

Gln Cys Leu Glu Gly Tyr Phe Gly Ser Ala Cys Glu Glu Lys Val Asp
        420                 425                 430

Pro Cys Met Ser Ser Pro Cys Gln Asn Asn Gly Thr Cys Tyr Val Asp
    435                 440                 445

Gly Val His Phe Thr Cys Ser Cys Ser Pro Gly Phe Thr Gly Pro Thr
    450                 455                 460

Cys Ala Gln Leu Val Asp Phe Cys Ala Leu Ser Pro Cys Ala His Gly
465                 470                 475                 480

Met Cys Arg Ser Val Gly Thr Ser Tyr Lys Cys Leu Cys Asp Pro Gly
                485                 490                 495

Tyr His Gly Leu Tyr Cys Glu Glu Tyr Asn Glu Cys Leu Ser Ala
        500                 505                 510

Pro Cys Leu Asn Ala Ala Thr Cys Arg Asp Leu Ile Asn Gly Tyr Glu
```

```
                515                 520                 525
Cys Val Cys Leu Ala Glu Tyr Lys Gly Thr His Cys Glu Leu Tyr Lys
    530                 535                 540

Asp Pro Cys Ala Asn Ile Ser Cys Leu Asn Gly Gly Thr Cys Asp Ser
545                 550                 555                 560

Glu Gly Leu Asn Gly Thr Cys Ile Cys Ala Pro Gly Phe Thr Gly Glu
                565                 570                 575

Glu Cys Asp Ile Asp Ile Asn Glu Cys Asp Ser Asn Pro Cys His His
                580                 585                 590

Ala Gly Thr Cys Leu Asp Gln Pro Asn Gly Tyr Thr Cys His Cys Pro
                595                 600                 605

His Gly Trp Val Gly Ala Asn Cys Glu Ile His Leu Gln Trp Lys Ser
    610                 615                 620

Gly His Met Ala Glu Ser Leu Thr Asn Met Pro Arg His Ser Leu Tyr
625                 630                 635                 640

Ile Ile Ile Gly Ala Leu Cys Val Ala Phe Ile Leu Met Leu Ile Ile
                645                 650                 655

Leu Ile Val Gly Ile Cys Arg Ile Ser Arg Ile Glu Tyr Gln Gly Ser
                660                 665                 670

Ser Arg Pro Ala Tyr Glu Glu Phe Tyr Asn Cys Arg Ser Ile Asp Ser
                675                 680                 685

Glu Phe Ser Asn Ala Ile Ala Ser Ile Arg His Ala Arg Phe Gly Lys
                690                 695                 700

Lys Ser Arg Pro Ala Met Tyr Asp Val Thr Pro Ile Ala Tyr Glu Asp
705                 710                 715                 720

Tyr Ser Pro Asp Asp Lys Pro Leu Val Thr Leu Ile Lys Thr Lys Asp
                725                 730                 735

Leu

<210> SEQ ID NO 3
<211> LENGTH: 913
<212> TYPE: PRT
<213> ORGANISM: Homo sapiens

<400> SEQUENCE: 3

Met Gly Pro Glu Ala Leu Ser Ser Leu Leu Leu Leu Leu Leu Val Ala
1               5                   10                  15

Ser Gly Asp Ala Asp Met Lys Gly His Phe Asp Pro Ala Lys Cys Arg
                20                  25                  30

Tyr Ala Leu Gly Met Gln Asp Arg Thr Ile Pro Asp Ser Asp Ile Ser
            35                  40                  45

Ala Ser Ser Ser Trp Ser Asp Ser Thr Ala Ala Arg His Ser Arg Leu
        50                  55                  60

Glu Ser Ser Asp Gly Asp Gly Ala Trp Cys Pro Ala Gly Ser Val Phe
65                  70                  75                  80

Pro Lys Glu Glu Glu Tyr Leu Gln Val Asp Leu Gln Arg Leu His Leu
                85                  90                  95

Val Ala Leu Val Gly Thr Gln Gly Arg His Ala Gly Gly Leu Gly Lys
            100                 105                 110

Glu Phe Ser Arg Ser Tyr Arg Leu Arg Tyr Ser Arg Asp Gly Arg Arg
        115                 120                 125

Trp Met Gly Trp Lys Asp Arg Trp Gly Gln Glu Val Ile Ser Gly Asn
    130                 135                 140

Glu Asp Pro Glu Gly Val Val Leu Lys Asp Leu Gly Pro Pro Met Val
145                 150                 155                 160
```

-continued

```
Ala Arg Leu Val Arg Phe Tyr Pro Arg Ala Asp Arg Val Met Ser Val
            165                 170                 175

Cys Leu Arg Val Glu Leu Tyr Gly Cys Leu Trp Arg Asp Gly Leu Leu
            180                 185                 190

Ser Tyr Thr Ala Pro Val Gly Gln Thr Met Tyr Leu Ser Glu Ala Val
            195                 200                 205

Tyr Leu Asn Asp Ser Thr Tyr Asp Gly His Thr Val Gly Gly Leu Gln
            210                 215                 220

Tyr Gly Gly Leu Gly Gln Leu Ala Asp Gly Val Val Gly Leu Asp Asp
225                 230                 235                 240

Phe Arg Lys Ser Gln Glu Leu Arg Val Trp Pro Gly Tyr Asp Tyr Val
                245                 250                 255

Gly Trp Ser Asn His Ser Phe Ser Gly Tyr Val Glu Met Glu Phe
            260                 265                 270

Glu Phe Asp Arg Leu Arg Ala Phe Gln Ala Met Gln Val His Cys Asn
            275                 280                 285

Asn Met His Thr Leu Gly Ala Arg Leu Pro Gly Gly Val Glu Cys Arg
            290                 295                 300

Phe Arg Arg Gly Pro Ala Met Ala Trp Glu Gly Glu Pro Met Arg His
305                 310                 315                 320

Asn Leu Gly Gly Asn Leu Gly Asp Pro Arg Ala Arg Ala Val Ser Val
                325                 330                 335

Pro Leu Gly Gly Arg Val Ala Arg Phe Leu Gln Cys Arg Phe Leu Phe
            340                 345                 350

Ala Gly Pro Trp Leu Leu Phe Ser Glu Ile Ser Phe Ile Ser Asp Val
            355                 360                 365

Val Asn Asn Ser Ser Pro Ala Leu Gly Gly Thr Phe Pro Pro Ala Pro
            370                 375                 380

Trp Trp Pro Pro Gly Pro Pro Thr Asn Phe Ser Ser Leu Glu Leu
385                 390                 395                 400

Glu Pro Arg Gly Gln Gln Pro Val Ala Lys Ala Glu Gly Ser Pro Thr
                405                 410                 415

Ala Ile Leu Ile Gly Cys Leu Val Ala Ile Ile Leu Leu Leu Leu Leu
            420                 425                 430

Ile Ile Ala Leu Met Leu Trp Arg Leu His Trp Arg Arg Leu Leu Ser
            435                 440                 445

Lys Ala Glu Arg Arg Val Leu Glu Glu Glu Leu Thr Val His Leu Ser
450                 455                 460

Val Pro Gly Asp Thr Ile Leu Ile Asn Asn Arg Pro Gly Pro Arg Glu
465                 470                 475                 480

Pro Pro Pro Tyr Gln Glu Pro Arg Pro Arg Gly Asn Pro Pro His Ser
                485                 490                 495

Ala Pro Cys Val Pro Asn Gly Ser Ala Leu Leu Leu Ser Asn Pro Ala
            500                 505                 510

Tyr Arg Leu Leu Leu Ala Thr Tyr Ala Arg Pro Pro Arg Gly Pro Gly
            515                 520                 525

Pro Pro Thr Pro Ala Trp Ala Lys Pro Thr Asn Thr Gln Ala Tyr Ser
            530                 535                 540

Gly Asp Tyr Met Glu Pro Glu Lys Pro Gly Ala Pro Leu Leu Pro Pro
545                 550                 555                 560

Pro Pro Gln Asn Ser Val Pro His Tyr Ala Glu Ala Asp Ile Val Thr
                565                 570                 575

Leu Gln Gly Val Thr Gly Gly Asn Thr Tyr Ala Val Pro Ala Leu Pro
```

```
                    580             585             590
Pro Gly Ala Val Gly Asp Gly Pro Arg Val Asp Phe Pro Arg Ser
            595                 600             605

Arg Leu Arg Phe Lys Glu Lys Leu Gly Glu Gly Gln Phe Gly Glu Val
            610                 615             620

His Leu Cys Glu Val Asp Ser Pro Gln Asp Leu Val Ser Leu Asp Phe
625                 630             635                 640

Pro Leu Asn Val Arg Lys Gly His Pro Leu Leu Val Ala Val Lys Ile
            645                 650             655

Leu Arg Pro Asp Ala Thr Lys Asn Ala Arg Asn Asp Phe Leu Lys Glu
            660                 665             670

Val Lys Ile Met Ser Arg Leu Lys Asp Pro Asn Ile Ile Arg Leu Leu
            675                 680             685

Gly Val Cys Val Gln Asp Asp Pro Leu Cys Met Ile Thr Asp Tyr Met
            690                 695             700

Glu Asn Gly Asp Leu Asn Gln Phe Leu Ser Ala His Gln Leu Glu Asp
705                 710             715                 720

Lys Ala Ala Glu Gly Ala Pro Gly Asp Gly Gln Ala Ala Gln Gly Pro
            725                 730             735

Thr Ile Ser Tyr Pro Met Leu Leu His Val Ala Ala Gln Ile Ala Ser
            740                 745             750

Gly Met Arg Tyr Leu Ala Thr Leu Asn Phe Val His Arg Asp Leu Ala
            755                 760             765

Thr Arg Asn Cys Leu Val Gly Glu Asn Phe Thr Ile Lys Ile Ala Asp
            770                 775             780

Phe Gly Met Ser Arg Asn Leu Tyr Ala Gly Asp Tyr Tyr Arg Val Gln
785                 790             795                 800

Gly Arg Ala Val Leu Pro Ile Arg Trp Met Ala Trp Glu Cys Ile Leu
            805                 810             815

Met Gly Lys Phe Thr Thr Ala Ser Asp Val Trp Ala Phe Gly Val Thr
            820                 825             830

Leu Trp Glu Val Leu Met Leu Cys Arg Ala Gln Pro Phe Gly Gln Leu
            835                 840             845

Thr Asp Glu Gln Val Ile Glu Asn Ala Gly Glu Phe Phe Arg Asp Gln
850                 855             860

Gly Arg Gln Val Tyr Leu Ser Arg Pro Pro Ala Cys Pro Gln Gly Leu
865                 870             875                 880

Tyr Glu Leu Met Leu Arg Cys Trp Ser Arg Glu Ser Glu Gln Arg Pro
            885                 890             895

Pro Phe Ser Gln Leu His Arg Phe Leu Ala Glu Asp Ala Leu Asn Thr
            900                 905             910

Val

<210> SEQ ID NO 4
<211> LENGTH: 876
<212> TYPE: PRT
<213> ORGANISM: Homo sapiens

<400> SEQUENCE: 4

Met Gly Pro Glu Ala Leu Ser Ser Leu Leu Leu Leu Leu Leu Val Ala
1               5                   10                  15

Ser Gly Asp Ala Asp Met Lys Gly His Phe Asp Pro Ala Lys Cys Arg
            20                  25                  30

Tyr Ala Leu Gly Met Gln Asp Arg Thr Ile Pro Asp Ser Asp Ile Ser
            35                  40                  45
```

```
Ala Ser Ser Ser Trp Ser Asp Ser Thr Ala Arg His Ser Arg Leu
    50                  55                  60

Glu Ser Ser Asp Gly Asp Gly Ala Trp Cys Pro Ala Gly Ser Val Phe
 65                  70                  75                  80

Pro Lys Glu Glu Glu Tyr Leu Gln Val Asp Leu Gln Arg Leu His Leu
                85                  90                  95

Val Ala Leu Val Gly Thr Gln Gly Arg His Ala Gly Leu Gly Lys
            100                 105                 110

Glu Phe Ser Arg Ser Tyr Arg Leu Arg Tyr Ser Arg Asp Gly Arg Arg
            115                 120                 125

Trp Met Gly Trp Lys Asp Arg Trp Gly Gln Glu Val Ile Ser Gly Asn
        130                 135                 140

Glu Asp Pro Glu Gly Val Val Leu Lys Asp Leu Gly Pro Pro Met Val
145                 150                 155                 160

Ala Arg Leu Val Arg Phe Tyr Pro Arg Ala Asp Arg Val Met Ser Val
                165                 170                 175

Cys Leu Arg Val Glu Leu Tyr Gly Cys Leu Trp Arg Asp Gly Leu Leu
            180                 185                 190

Ser Tyr Thr Ala Pro Val Gly Gln Thr Met Tyr Leu Ser Glu Ala Val
    195                 200                 205

Tyr Leu Asn Asp Ser Thr Tyr Asp Gly His Thr Val Gly Gly Leu Gln
210                 215                 220

Tyr Gly Gly Leu Gly Gln Leu Ala Asp Gly Val Val Gly Leu Asp Asp
225                 230                 235                 240

Phe Arg Lys Ser Gln Glu Leu Arg Val Trp Pro Gly Tyr Asp Tyr Val
                245                 250                 255

Gly Trp Ser Asn His Ser Phe Ser Gly Tyr Val Glu Met Glu Phe
            260                 265                 270

Glu Phe Asp Arg Leu Arg Ala Phe Gln Ala Met Gln Val His Cys Asn
            275                 280                 285

Asn Met His Thr Leu Gly Ala Arg Leu Pro Gly Gly Val Glu Cys Arg
290                 295                 300

Phe Arg Arg Gly Pro Ala Met Ala Trp Glu Gly Glu Pro Met Arg His
305                 310                 315                 320

Asn Leu Gly Gly Asn Leu Gly Asp Pro Arg Ala Arg Ala Val Ser Val
                325                 330                 335

Pro Leu Gly Gly Arg Val Ala Arg Phe Leu Gln Cys Arg Phe Leu Phe
            340                 345                 350

Ala Gly Pro Trp Leu Leu Phe Ser Glu Ile Ser Phe Ile Ser Asp Val
        355                 360                 365

Val Asn Asn Ser Ser Pro Ala Leu Gly Gly Thr Phe Pro Pro Ala Pro
370                 375                 380

Trp Trp Pro Pro Gly Pro Pro Thr Asn Phe Ser Ser Leu Glu Leu
385                 390                 395                 400

Glu Pro Arg Gly Gln Gln Pro Val Ala Lys Ala Glu Gly Ser Pro Thr
                405                 410                 415

Ala Ile Leu Ile Gly Cys Leu Val Ala Ile Ile Leu Leu Leu Leu Leu
            420                 425                 430

Ile Ile Ala Leu Met Leu Trp Arg Leu His Trp Arg Arg Leu Leu Ser
        435                 440                 445

Lys Ala Glu Arg Arg Val Leu Glu Glu Glu Leu Thr Val His Leu Ser
450                 455                 460

Val Pro Gly Asp Thr Ile Leu Ile Asn Asn Arg Pro Gly Pro Arg Glu
```

```
            465                 470                 475                 480
    Pro Pro Pro Tyr Gln Glu Pro Arg Pro Arg Gly Asn Pro Pro His Ser
                        485                 490                 495

Ala Pro Cys Val Pro Asn Gly Ser Ala Tyr Ser Gly Asp Tyr Met Glu
                500                 505                 510

Pro Glu Lys Pro Gly Ala Pro Leu Leu Pro Pro Pro Gln Asn Ser
            515                 520                 525

Val Pro His Tyr Ala Glu Ala Asp Ile Val Thr Leu Gln Gly Val Thr
        530                 535                 540

Gly Gly Asn Thr Tyr Ala Val Pro Ala Leu Pro Pro Gly Ala Val Gly
    545                 550                 555                 560

Asp Gly Pro Pro Arg Val Asp Phe Pro Arg Ser Arg Leu Arg Phe Lys
                    565                 570                 575

Glu Lys Leu Gly Glu Gly Gln Phe Gly Glu Val His Leu Cys Glu Val
                580                 585                 590

Asp Ser Pro Gln Asp Leu Val Ser Leu Asp Phe Pro Leu Asn Val Arg
                595                 600                 605

Lys Gly His Pro Leu Leu Val Ala Val Lys Ile Leu Arg Pro Asp Ala
                610                 615                 620

Thr Lys Asn Ala Arg Asn Asp Phe Leu Lys Glu Val Lys Ile Met Ser
    625                 630                 635                 640

Arg Leu Lys Asp Pro Asn Ile Ile Arg Leu Leu Gly Val Cys Val Gln
                    645                 650                 655

Asp Asp Pro Leu Cys Met Ile Thr Asp Tyr Met Glu Asn Gly Asp Leu
                    660                 665                 670

Asn Gln Phe Leu Ser Ala His Gln Leu Glu Asp Lys Ala Ala Glu Gly
                675                 680                 685

Ala Pro Gly Asp Gly Gln Ala Ala Gln Gly Pro Thr Ile Ser Tyr Pro
            690                 695                 700

Met Leu Leu His Val Ala Ala Gln Ile Ala Ser Gly Met Arg Tyr Leu
    705                 710                 715                 720

Ala Thr Leu Asn Phe Val His Arg Asp Leu Ala Thr Arg Asn Cys Leu
                    725                 730                 735

Val Gly Glu Asn Phe Thr Ile Lys Ile Ala Asp Phe Gly Met Ser Arg
                    740                 745                 750

Asn Leu Tyr Ala Gly Asp Tyr Tyr Arg Val Gln Gly Arg Ala Val Leu
                755                 760                 765

Pro Ile Arg Trp Met Ala Trp Glu Cys Ile Leu Met Gly Lys Phe Thr
            770                 775                 780

Thr Ala Ser Asp Val Trp Ala Phe Gly Val Thr Leu Trp Glu Val Leu
    785                 790                 795                 800

Met Leu Cys Arg Ala Gln Pro Phe Gly Gln Leu Thr Asp Glu Gln Val
                    805                 810                 815

Ile Glu Asn Ala Gly Glu Phe Phe Arg Asp Gln Gly Arg Gln Val Tyr
                    820                 825                 830

Leu Ser Arg Pro Pro Ala Cys Pro Gln Gly Leu Tyr Glu Leu Met Leu
                835                 840                 845

Arg Cys Trp Ser Arg Glu Ser Glu Gln Arg Pro Pro Phe Ser Gln Leu
            850                 855                 860

His Arg Phe Leu Ala Glu Asp Ala Leu Asn Thr Val
    865                 870                 875

<210> SEQ ID NO 5
<211> LENGTH: 919
```

<212> TYPE: PRT
<213> ORGANISM: Homo sapiens

<400> SEQUENCE: 5

```
Met Gly Pro Glu Ala Leu Ser Ser Leu Leu Leu Leu Leu Val Ala
1               5                   10                  15

Ser Gly Asp Ala Asp Met Lys Gly His Phe Asp Pro Ala Lys Cys Arg
            20                  25                  30

Tyr Ala Leu Gly Met Gln Asp Arg Thr Ile Pro Asp Ser Asp Ile Ser
            35                  40                  45

Ala Ser Ser Ser Trp Ser Asp Ser Thr Ala Ala Arg His Ser Arg Leu
        50                  55                  60

Glu Ser Ser Asp Gly Asp Gly Ala Trp Cys Pro Ala Gly Ser Val Phe
65                  70                  75                  80

Pro Lys Glu Glu Glu Tyr Leu Gln Val Asp Leu Gln Arg Leu His Leu
                85                  90                  95

Val Ala Leu Val Gly Thr Gln Gly Arg His Ala Gly Gly Leu Gly Lys
            100                 105                 110

Glu Phe Ser Arg Ser Tyr Arg Leu Arg Tyr Ser Arg Asp Gly Arg Arg
            115                 120                 125

Trp Met Gly Trp Lys Asp Arg Trp Gly Gln Glu Val Ile Ser Gly Asn
130                 135                 140

Glu Asp Pro Glu Gly Val Val Leu Lys Asp Leu Gly Pro Pro Met Val
145                 150                 155                 160

Ala Arg Leu Val Arg Phe Tyr Pro Arg Ala Asp Arg Val Met Ser Val
                165                 170                 175

Cys Leu Arg Val Glu Leu Tyr Gly Cys Leu Trp Arg Asp Gly Leu Leu
            180                 185                 190

Ser Tyr Thr Ala Pro Val Gly Gln Thr Met Tyr Leu Ser Glu Ala Val
        195                 200                 205

Tyr Leu Asn Asp Ser Thr Tyr Asp Gly His Thr Val Gly Gly Leu Gln
210                 215                 220

Tyr Gly Gly Leu Gly Gln Leu Ala Asp Gly Val Val Gly Leu Asp Asp
225                 230                 235                 240

Phe Arg Lys Ser Gln Glu Leu Arg Val Trp Pro Gly Tyr Asp Tyr Val
                245                 250                 255

Gly Trp Ser Asn His Ser Phe Ser Ser Gly Tyr Val Glu Met Glu Phe
            260                 265                 270

Glu Phe Asp Arg Leu Arg Ala Phe Gln Ala Met Gln Val His Cys Asn
        275                 280                 285

Asn Met His Thr Leu Gly Ala Arg Leu Pro Gly Gly Val Glu Cys Arg
290                 295                 300

Phe Arg Arg Gly Pro Ala Met Ala Trp Glu Gly Glu Pro Met Arg His
305                 310                 315                 320

Asn Leu Gly Gly Asn Leu Gly Asp Pro Arg Ala Arg Ala Val Ser Val
                325                 330                 335

Pro Leu Gly Gly Arg Val Ala Arg Phe Leu Gln Cys Arg Phe Leu Phe
            340                 345                 350

Ala Gly Pro Trp Leu Leu Phe Ser Glu Ile Ser Phe Ile Ser Asp Val
        355                 360                 365

Val Asn Asn Ser Ser Pro Ala Leu Gly Gly Thr Phe Pro Pro Ala Pro
370                 375                 380

Trp Trp Pro Pro Gly Pro Pro Thr Asn Phe Ser Ser Leu Glu Leu
385                 390                 395                 400
```

-continued

```
Glu Pro Arg Gly Gln Gln Pro Val Ala Lys Ala Glu Gly Ser Pro Thr
                405                 410                 415
Ala Ile Leu Ile Gly Cys Leu Val Ala Ile Ile Leu Leu Leu Leu Leu
            420                 425                 430
Ile Ile Ala Leu Met Leu Trp Arg Leu His Trp Arg Arg Leu Leu Ser
        435                 440                 445
Lys Ala Glu Arg Arg Val Leu Glu Glu Glu Leu Thr Val His Leu Ser
    450                 455                 460
Val Pro Gly Asp Thr Ile Leu Ile Asn Asn Arg Pro Gly Pro Arg Glu
465                 470                 475                 480
Pro Pro Pro Tyr Gln Glu Pro Arg Pro Arg Gly Asn Pro Pro His Ser
                485                 490                 495
Ala Pro Cys Val Pro Asn Gly Ser Ala Leu Leu Leu Ser Asn Pro Ala
            500                 505                 510
Tyr Arg Leu Leu Leu Ala Thr Tyr Ala Arg Pro Pro Arg Gly Pro Gly
        515                 520                 525
Pro Pro Thr Pro Ala Trp Ala Lys Pro Thr Asn Thr Gln Ala Tyr Ser
    530                 535                 540
Gly Asp Tyr Met Glu Pro Glu Lys Pro Gly Ala Pro Leu Leu Pro Pro
545                 550                 555                 560
Pro Pro Gln Asn Ser Val Pro His Tyr Ala Glu Ala Asp Ile Val Thr
                565                 570                 575
Leu Gln Gly Val Thr Gly Gly Asn Thr Tyr Ala Val Pro Ala Leu Pro
            580                 585                 590
Pro Gly Ala Val Gly Asp Gly Pro Pro Arg Val Asp Phe Pro Arg Ser
        595                 600                 605
Arg Leu Arg Phe Lys Glu Lys Leu Gly Glu Gly Gln Phe Gly Glu Val
    610                 615                 620
His Leu Cys Glu Val Asp Ser Pro Gln Asp Leu Val Ser Leu Asp Phe
625                 630                 635                 640
Pro Leu Asn Val Arg Lys Gly His Pro Leu Leu Val Ala Val Lys Ile
                645                 650                 655
Leu Arg Pro Asp Ala Thr Lys Asn Ala Ser Phe Ser Leu Phe Ser Arg
            660                 665                 670
Asn Asp Phe Leu Lys Glu Val Lys Ile Met Ser Arg Leu Lys Asp Pro
        675                 680                 685
Asn Ile Ile Arg Leu Leu Gly Val Cys Val Gln Asp Asp Pro Leu Cys
    690                 695                 700
Met Ile Thr Asp Tyr Met Glu Asn Gly Asp Leu Asn Gln Phe Leu Ser
705                 710                 715                 720
Ala His Gln Leu Glu Asp Lys Ala Ala Glu Gly Ala Pro Gly Asp Gly
                725                 730                 735
Gln Ala Ala Gln Gly Pro Thr Ile Ser Tyr Pro Met Leu Leu His Val
            740                 745                 750
Ala Ala Gln Ile Ala Ser Gly Met Arg Tyr Leu Ala Thr Leu Asn Phe
        755                 760                 765
Val His Arg Asp Leu Ala Thr Arg Asn Cys Leu Val Gly Glu Asn Phe
    770                 775                 780
Thr Ile Lys Ile Ala Asp Phe Gly Met Ser Arg Asn Leu Tyr Ala Gly
785                 790                 795                 800
Asp Tyr Tyr Arg Val Gln Gly Arg Ala Val Leu Pro Ile Arg Trp Met
                805                 810                 815
Ala Trp Glu Cys Ile Leu Met Gly Lys Phe Thr Thr Ala Ser Asp Val
            820                 825                 830
```

-continued

Trp Ala Phe Gly Val Thr Leu Trp Glu Val Leu Met Leu Cys Arg Ala
    835                 840                 845

Gln Pro Phe Gly Gln Leu Thr Asp Glu Gln Val Ile Glu Asn Ala Gly
    850                 855                 860

Glu Phe Phe Arg Asp Gln Gly Arg Gln Val Tyr Leu Ser Arg Pro Pro
865                 870                 875                 880

Ala Cys Pro Gln Gly Leu Tyr Glu Leu Met Leu Arg Cys Trp Ser Arg
            885                 890                 895

Glu Ser Glu Gln Arg Pro Pro Phe Ser Gln Leu His Arg Phe Leu Ala
            900                 905                 910

Glu Asp Ala Leu Asn Thr Val
            915

<210> SEQ ID NO 6
<211> LENGTH: 911
<212> TYPE: PRT
<213> ORGANISM: Mus musculus

<400> SEQUENCE: 6

Met Gly Thr Gly Thr Leu Ser Ser Leu Leu Leu Leu Leu Leu Leu Val
1               5                   10                  15

Thr Ile Gly Asp Ala Asp Met Lys Gly His Phe Asp Pro Ala Lys Cys
            20                  25                  30

Arg Tyr Ala Leu Gly Met Gln Asp Arg Thr Ile Pro Asp Ser Asp Ile
        35                  40                  45

Ser Val Ser Ser Ser Trp Ser Asp Ser Thr Ala Ala Arg His Ser Arg
    50                  55                  60

Leu Glu Ser Ser Asp Gly Asp Gly Ala Trp Cys Pro Ala Gly Pro Val
65                  70                  75                  80

Phe Pro Lys Glu Glu Glu Tyr Leu Gln Val Asp Leu Arg Arg Leu His
                85                  90                  95

Leu Val Ala Leu Val Gly Thr Gln Gly Arg His Ala Gly Gly Leu Gly
            100                 105                 110

Lys Glu Phe Ser Arg Ser Tyr Arg Leu Arg Tyr Ser Arg Asp Gly Arg
        115                 120                 125

Arg Trp Met Asp Trp Lys Asp Arg Trp Gly Gln Glu Val Ile Ser Gly
    130                 135                 140

Asn Glu Asp Pro Gly Gly Val Val Leu Lys Asp Leu Gly Pro Pro Met
145                 150                 155                 160

Val Ala Arg Leu Val Arg Phe Tyr Pro Arg Ala Asp Arg Val Met Ser
                165                 170                 175

Val Cys Leu Arg Val Glu Leu Tyr Gly Cys Leu Trp Arg Asp Gly Leu
            180                 185                 190

Leu Ser Tyr Thr Ala Pro Val Gly Gln Thr Met Gln Leu Ser Glu Val
        195                 200                 205

Met Val His Leu Asn Asp Ser Thr Tyr Asp Gly Tyr Thr Ala Gly Gly
    210                 215                 220

Leu Gln Tyr Gly Gly Leu Gly Gln Leu Ala Asp Gly Val Val Gly Leu
225                 230                 235                 240

Asp Asp Phe Arg Gln Ser Gln Glu Leu Arg Val Trp Pro Gly Tyr Asp
                245                 250                 255

Tyr Val Gly Trp Ser Asn Gln Ser Phe Pro Thr Gly Tyr Val Glu Met
            260                 265                 270

Glu Phe Glu Phe Asp Arg Leu Arg Thr Phe Gln Thr Met Gln Val His
        275                 280                 285

```
Cys Asn Asn Met His Thr Leu Gly Ala Arg Leu Pro Gly Gly Val Glu
    290                 295                 300

Cys Arg Phe Lys Arg Gly Pro Ala Met Ala Trp Glu Gly Glu Pro Val
305                 310                 315                 320

Arg His Ala Leu Gly Gly Ser Leu Gly Asp Pro Arg Ala Arg Ala Ile
                    325                 330                 335

Ser Val Pro Leu Gly Gly His Val Gly Arg Phe Leu Gln Cys Arg Phe
                340                 345                 350

Leu Phe Ala Gly Pro Trp Leu Leu Phe Ser Glu Ile Ser Phe Ile Ser
            355                 360                 365

Asp Val Val Asn Asp Ser Ser Asp Thr Phe Pro Pro Ala Pro Trp Trp
        370                 375                 380

Pro Pro Gly Pro Pro Thr Asn Phe Ser Ser Leu Glu Leu Glu Pro
385                 390                 395                 400

Arg Gly Gln Gln Pro Val Ala Lys Ala Glu Gly Ser Pro Thr Ala Ile
                    405                 410                 415

Leu Ile Gly Cys Leu Val Ala Ile Ile Leu Leu Leu Leu Ile Ile
                420                 425                 430

Ala Leu Met Leu Trp Arg Leu His Trp Arg Arg Leu Leu Ser Lys Ala
            435                 440                 445

Glu Arg Arg Val Leu Glu Glu Glu Leu Thr Val His Leu Ser Val Pro
450                 455                 460

Gly Asp Thr Ile Leu Ile Asn Asn Arg Pro Gly Pro Arg Glu Pro Pro
465                 470                 475                 480

Pro Tyr Gln Glu Pro Arg Pro Arg Gly Thr Pro Pro His Ser Ala Pro
                    485                 490                 495

Cys Val Pro Asn Gly Ser Ala Leu Leu Leu Ser Asn Pro Ala Tyr Arg
                500                 505                 510

Leu Leu Leu Ala Thr Tyr Ala Arg Pro Pro Arg Gly Pro Gly Pro Pro
            515                 520                 525

Thr Pro Ala Trp Ala Lys Pro Thr Asn Thr Gln Ala Cys Ser Gly Asp
        530                 535                 540

Tyr Met Glu Pro Glu Lys Pro Gly Ala Pro Leu Leu Pro Pro Pro Pro
545                 550                 555                 560

Gln Asn Ser Val Pro His Tyr Ala Glu Ala Asp Ile Val Thr Leu Gln
                    565                 570                 575

Gly Val Thr Gly Gly Asn Thr Tyr Ala Val Pro Ala Leu Pro Pro Gly
                580                 585                 590

Ala Val Gly Asp Gly Pro Pro Arg Val Asp Phe Pro Arg Ser Arg Leu
            595                 600                 605

Arg Phe Lys Glu Lys Leu Gly Glu Gly Gln Phe Gly Glu Val His Leu
        610                 615                 620

Cys Glu Val Glu Asp Pro Gln Asp Leu Val Ser Ser Asp Phe Pro Ile
625                 630                 635                 640

Ser Val His Lys Gly His Pro Leu Leu Val Ala Val Lys Ile Leu Arg
                    645                 650                 655

Pro Asp Ala Thr Lys Asn Ala Arg Asn Asp Phe Leu Lys Glu Val Lys
                660                 665                 670

Ile Met Ser Arg Leu Lys Asp Pro Asn Ile Ile Arg Leu Leu Gly Val
            675                 680                 685

Cys Val Gln Asp Asp Pro Leu Cys Met Ile Thr Asp Tyr Met Glu Asn
        690                 695                 700

Gly Asp Leu Asn Gln Phe Leu Ser Ala Arg Gln Leu Glu Asn Lys Ala
```

```
                705                 710                 715                 720
Thr Gln Gly Leu Ser Gly Asp Thr Glu Ser Asp Gln Gly Pro Thr Ile
                    725                 730                 735
Ser Tyr Pro Met Leu Leu His Val Gly Ala Gln Ile Ala Ser Gly Met
                740                 745                 750
Arg Tyr Leu Ala Thr Leu Asn Phe Val His Arg Asp Leu Ala Thr Arg
                755                 760                 765
Asn Cys Leu Val Gly Glu Asn Phe Thr Ile Lys Ile Ala Asp Phe Gly
            770                 775                 780
Met Ser Arg Asn Leu Tyr Ala Gly Asp Tyr Tyr Arg Val Gln Gly Arg
785                 790                 795                 800
Ala Val Leu Pro Ile Arg Trp Met Ala Trp Glu Cys Ile Leu Met Gly
                805                 810                 815
Lys Phe Thr Thr Ala Ser Asp Val Trp Ala Phe Gly Val Thr Leu Trp
                820                 825                 830
Glu Val Leu Met Leu Cys Arg Ser Gln Pro Phe Gly Gln Leu Thr Asp
                835                 840                 845
Glu Gln Val Ile Glu Asn Ala Gly Glu Phe Phe Arg Asp Gln Gly Arg
            850                 855                 860
Gln Val Tyr Leu Ser Arg Pro Pro Ala Cys Pro Gln Thr Leu Tyr Glu
865                 870                 875                 880
Leu Met Leu Arg Cys Trp Ser Arg Glu Pro Glu Gln Arg Pro Pro Phe
                885                 890                 895
Ala Gln Leu His Arg Phe Leu Ala Asp Asp Ala Leu Asn Thr Val
                900                 905                 910

<210> SEQ ID NO 7
<211> LENGTH: 874
<212> TYPE: PRT
<213> ORGANISM: Mus musculus

<400> SEQUENCE: 7

Met Gly Thr Gly Thr Leu Ser Ser Leu Leu Leu Leu Leu Leu Leu Val
1               5                   10                  15
Thr Ile Gly Asp Ala Asp Met Lys Gly His Phe Asp Pro Ala Lys Cys
                20                  25                  30
Arg Tyr Ala Leu Gly Met Gln Asp Arg Thr Ile Pro Asp Ser Asp Ile
                35                  40                  45
Ser Val Ser Ser Ser Trp Ser Asp Ser Thr Ala Ala Arg His Ser Arg
            50                  55                  60
Leu Glu Ser Ser Asp Gly Asp Gly Ala Trp Cys Pro Ala Gly Pro Val
65                  70                  75                  80
Phe Pro Lys Glu Glu Tyr Leu Gln Val Asp Leu Arg Arg Leu His
                85                  90                  95
Leu Val Ala Leu Val Gly Thr Gln Gly Arg His Ala Gly Gly Leu Gly
                100                 105                 110
Lys Glu Phe Ser Arg Ser Tyr Arg Leu Arg Tyr Ser Arg Asp Gly Arg
                115                 120                 125
Arg Trp Met Asp Trp Lys Asp Arg Trp Gly Gln Glu Val Ile Ser Gly
            130                 135                 140
Asn Glu Asp Pro Gly Gly Val Val Leu Lys Asp Leu Gly Pro Pro Met
145                 150                 155                 160
Val Ala Arg Leu Val Arg Phe Tyr Pro Arg Ala Asp Arg Val Met Ser
                165                 170                 175
Val Cys Leu Arg Val Glu Leu Tyr Gly Cys Leu Trp Arg Asp Gly Leu
```

-continued

```
                180                 185                 190
Leu Ser Tyr Thr Ala Pro Val Gly Gln Thr Met Gln Leu Ser Glu Val
            195                 200                 205

Met Val His Leu Asn Asp Ser Thr Tyr Asp Gly Tyr Thr Ala Gly Gly
210                 215                 220

Leu Gln Tyr Gly Gly Leu Gly Gln Leu Ala Asp Gly Val Val Gly Leu
225                 230                 235                 240

Asp Asp Phe Arg Gln Ser Gln Glu Leu Arg Val Trp Pro Gly Tyr Asp
                245                 250                 255

Tyr Val Gly Trp Ser Asn Gln Ser Phe Pro Thr Gly Tyr Val Glu Met
            260                 265                 270

Glu Phe Glu Phe Asp Arg Leu Arg Thr Phe Gln Thr Met Gln Val His
            275                 280                 285

Cys Asn Asn Met His Thr Leu Gly Ala Arg Leu Pro Gly Gly Val Glu
290                 295                 300

Cys Arg Phe Lys Arg Gly Pro Ala Met Ala Trp Glu Gly Glu Pro Val
305                 310                 315                 320

Arg His Ala Leu Gly Gly Ser Leu Gly Asp Pro Arg Ala Arg Ala Ile
                325                 330                 335

Ser Val Pro Leu Gly Gly His Val Gly Arg Phe Leu Gln Cys Arg Phe
            340                 345                 350

Leu Phe Ala Gly Pro Trp Leu Leu Phe Ser Glu Ile Ser Phe Ile Ser
            355                 360                 365

Asp Val Val Asn Asp Ser Ser Asp Thr Phe Pro Pro Ala Pro Trp Trp
            370                 375                 380

Pro Pro Gly Pro Pro Thr Asn Phe Ser Ser Leu Glu Leu Glu Pro
385                 390                 395                 400

Arg Gly Gln Gln Pro Val Ala Lys Ala Glu Gly Ser Pro Thr Ala Ile
                405                 410                 415

Leu Ile Gly Cys Leu Val Ala Ile Ile Leu Leu Leu Leu Ile Ile
            420                 425                 430

Ala Leu Met Leu Trp Arg Leu His Trp Arg Arg Leu Leu Ser Lys Ala
            435                 440                 445

Glu Arg Arg Val Leu Glu Glu Glu Leu Thr Val His Leu Ser Val Pro
450                 455                 460

Gly Asp Thr Ile Leu Ile Asn Asn Arg Pro Gly Pro Arg Glu Pro Pro
465                 470                 475                 480

Pro Tyr Gln Glu Pro Arg Pro Arg Gly Thr Pro Pro His Ser Ala Pro
                485                 490                 495

Cys Val Pro Asn Gly Ser Ala Cys Ser Gly Asp Tyr Met Glu Pro Glu
            500                 505                 510

Lys Pro Gly Ala Pro Leu Leu Pro Pro Pro Gln Asn Ser Val Pro
            515                 520                 525

His Tyr Ala Glu Ala Asp Ile Val Thr Leu Gln Gly Val Thr Gly Gly
            530                 535                 540

Asn Thr Tyr Ala Val Pro Ala Leu Pro Pro Gly Ala Val Gly Asp Gly
545                 550                 555                 560

Pro Pro Arg Val Asp Phe Pro Arg Ser Arg Leu Arg Phe Lys Glu Lys
                565                 570                 575

Leu Gly Glu Gly Gln Phe Gly Glu Val His Leu Cys Glu Val Glu Asp
            580                 585                 590

Pro Gln Asp Leu Val Ser Ser Asp Phe Pro Ile Ser Val His Lys Gly
            595                 600                 605
```

-continued

```
His Pro Leu Leu Val Ala Val Lys Ile Leu Arg Pro Asp Ala Thr Lys
            610             615                 620

Asn Ala Arg Asn Asp Phe Leu Lys Glu Val Lys Ile Met Ser Arg Leu
625                 630                 635                 640

Lys Asp Pro Asn Ile Ile Arg Leu Leu Gly Val Cys Val Gln Asp Asp
                645                 650                 655

Pro Leu Cys Met Ile Thr Asp Tyr Met Glu Asn Gly Asp Leu Asn Gln
            660                 665                 670

Phe Leu Ser Ala Arg Gln Leu Glu Asn Lys Ala Thr Gln Gly Leu Ser
            675                 680                 685

Gly Asp Thr Glu Ser Asp Gln Gly Pro Thr Ile Ser Tyr Pro Met Leu
            690                 695                 700

Leu His Val Gly Ala Gln Ile Ala Ser Gly Met Arg Tyr Leu Ala Thr
705                 710                 715                 720

Leu Asn Phe Val His Arg Asp Leu Ala Thr Arg Asn Cys Leu Val Gly
                725                 730                 735

Glu Asn Phe Thr Ile Lys Ile Ala Asp Phe Gly Met Ser Arg Asn Leu
            740                 745                 750

Tyr Ala Gly Asp Tyr Tyr Arg Val Gln Gly Arg Ala Val Leu Pro Ile
            755                 760                 765

Arg Trp Met Ala Trp Glu Cys Ile Leu Met Gly Lys Phe Thr Thr Ala
    770                 775                 780

Ser Asp Val Trp Ala Phe Gly Val Thr Leu Trp Glu Val Leu Met Leu
785                 790                 795                 800

Cys Arg Ser Gln Pro Phe Gly Gln Leu Thr Asp Glu Gln Val Ile Glu
                805                 810                 815

Asn Ala Gly Glu Phe Phe Arg Asp Gln Gly Arg Gln Val Tyr Leu Ser
                820                 825                 830

Arg Pro Pro Ala Cys Pro Gln Thr Leu Tyr Glu Leu Met Leu Arg Cys
            835                 840                 845

Trp Ser Arg Glu Pro Glu Gln Arg Pro Pro Phe Ala Gln Leu His Arg
    850                 855                 860

Phe Leu Ala Asp Asp Ala Leu Asn Thr Val
865                 870
```